(12) United States Patent
Hayslip et al.

(10) Patent No.: US 11,285,159 B2
(45) Date of Patent: Mar. 29, 2022

(54) DOSING REGIMENS FOR USE IN TREATING MYELOFIBROSIS AND MPN-RELATED DISORDERS WITH NAVITOCLAX

(71) Applicants: AbbVie Inc., North Chicago, IL (US); AbbVie Deutschland GmbH & Co. KG, Wiesbaden (DE)

(72) Inventors: John Hayslip, Lexington, KY (US); Leanne M. Holes, Bothell, WA (US); Sven Mensing, Ludwigshafen (DE); Silpa Nuthalapati, Vernon Hills, IL (US)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 17/089,415

(22) Filed: Nov. 4, 2020

(65) Prior Publication Data

US 2021/0128573 A1  May 6, 2021

Related U.S. Application Data

(60) Provisional application No. 62/930,951, filed on Nov. 5, 2019, provisional application No. 62/984,518, filed on Mar. 3, 2020.

(51) Int. Cl.
*A61K 31/5377* (2006.01)
*A61K 31/52* (2006.01)
*A61P 35/00* (2006.01)

(52) U.S. Cl.
CPC .......... *A61K 31/5377* (2013.01); *A61K 31/52* (2013.01); *A61P 35/00* (2018.01)

(58) Field of Classification Search
CPC ...... A61P 35/00; A61K 31/52; A61K 31/5377
See application file for complete search history.

(56) References Cited

U.S. PATENT DOCUMENTS

| | | | |
|---|---|---|---|
| 7,390,799 B2 | 6/2008 | Bruncko et al. |
| 7,709,467 B2 | 5/2010 | Bruncko et al. |
| 7,842,681 B2 | 11/2010 | Elmore et al. |
| 7,906,505 B2 | 3/2011 | Bruncko et al. |
| 8,168,784 B2 | 5/2012 | Franczyk, II et al. |
| 8,323,649 B2 | 12/2012 | Garcia-Martinez et al. |
| 8,362,013 B2 | 1/2013 | Borchardt et al. |
| 8,362,014 B2 | 1/2013 | Zhang et al. |
| 8,513,243 B2 | 8/2013 | Zhang et al. |
| 8,624,027 B2 | 1/2014 | Shah et al. |
| 8,748,108 B2 | 6/2014 | Mckeegan et al. |
| 8,927,009 B2 | 1/2015 | Tong et al. |
| 8,992,920 B2 | 3/2015 | Smith |
| 9,085,615 B2 | 7/2015 | Garcia-Martinez et al. |
| 9,187,560 B2 | 11/2015 | Smith et al. |
| 9,212,223 B2 | 12/2015 | Smith |
| 9,265,825 B2 | 2/2016 | Smith |
| 9,446,064 B2 | 9/2016 | Klaus et al. |
| 9,468,676 B2 | 10/2016 | Smith |
| 9,481,725 B2 | 11/2016 | Dutzar et al. |
| 9,642,796 B2 | 5/2017 | Packhaeuser et al. |
| 9,717,793 B2 | 8/2017 | Smith |
| 9,724,410 B2 | 8/2017 | Smith et al. |
| 9,732,150 B2 | 8/2017 | Garcia-Martinez et al. |
| 9,775,921 B2 | 10/2017 | Garcia-Martinez et al. |
| 9,821,057 B2 | 11/2017 | Smith et al. |
| 9,849,128 B2 | 12/2017 | Laberge et al. |
| 9,855,266 B2 | 1/2018 | Laberge et al. |
| 9,879,074 B2 | 1/2018 | Garcia-Martinez et al. |
| 9,980,962 B2 | 5/2018 | Laberge et al. |
| 9,993,472 B2 | 6/2018 | Laberge et al. |
| 9,994,635 B2 | 6/2018 | Smith |
| 10,010,546 B2 | 7/2018 | Laberge et al. |
| 10,053,506 B2 | 8/2018 | Smith et al. |
| 10,093,732 B2 | 10/2018 | Smith |
| 10,100,108 B2 | 10/2018 | Dutzar et al. |
| 10,117,955 B2 | 11/2018 | Garcia-Martinez et al. |
| 10,130,628 B2 | 11/2018 | David et al. |
| 10,213,426 B2 | 2/2019 | Laberge et al. |
| 10,258,618 B2 | 4/2019 | Laberge et al. |
| 10,328,058 B2 | 6/2019 | Baker et al. |
| 10,328,073 B2 | 6/2019 | Laberge et al. |
| 10,391,169 B2 | 8/2019 | Garcia-Martinez et al. |
| 10,413,542 B2 | 9/2019 | Laberge et al. |
| 10,478,432 B2 | 11/2019 | Laberge et al. |
| 10,478,433 B2 | 11/2019 | Laberge et al. |
| 10,517,866 B2 | 12/2019 | Laberge et al. |
| 10,525,074 B2 | 1/2020 | Klaus et al. |
| 10,640,560 B2 | 5/2020 | Smith et al. |
| 10,668,078 B2 | 6/2020 | Whitsett et al. |

(Continued)

FOREIGN PATENT DOCUMENTS

WO  WO-2007040650 A2  4/2007
WO  WO-2008030836 A2  3/2008

(Continued)

OTHER PUBLICATIONS

US 8,992,904 B2, 03/2015, Smith (withdrawn)
US 9,957,322 B2, 05/2018, Smith (withdrawn)
Bankar, et al., Investigational non-JAK inhibitors for chronic phase myelofibrosis, Expert Opinion on Investigational Drugs, 29:5, 461-474, DOI: 10.1080/13543784.2020.1751121 (2020) (Year: 2020).*
Ackier S., et al., "ABT-263 and Rapamycin act Cooperatively to Kill Lymphoma Cells in Vitro and in Vivo," Molecular Cancer Therapeutics, 2008, vol. 7 (10), pp. 3265-3274.
Bertino E.M., et al., "Phase IB study of osimertinib in combination with navitoclax in EGFR-mutant NSCLC following resistance to initial EGFR therapy (ETCTN 9903)," Clinical Cancer Research, 2021, vol. 21 (6), pp. 1604-1611, Published Online First Dec. 29, 2020.

(Continued)

*Primary Examiner* — Erich A Leeser

(57) ABSTRACT

The invention described herein relates to methods for treating a human subject with myelofibrosis or an MPN-related disorder, comprising administering navitoclax to the subject optionally in combination with ruxolitinib.

42 Claims, 8 Drawing Sheets

(56) References Cited

U.S. PATENT DOCUMENTS

| | | |
|---|---|---|
| 10,787,511 B2 | 9/2020 | Smith |
| 10,799,508 B2 | 10/2020 | Beeharry et al. |
| 10,875,917 B2 | 12/2020 | Smith |
| 2007/0027135 A1 | 2/2007 | Bruncko et al. |
| 2008/0026906 A1 | 1/2008 | Jeon |
| 2008/0076779 A1 | 3/2008 | Elmore et al. |
| 2008/0160545 A1 | 7/2008 | McKeegan et al. |
| 2008/0182845 A1 | 7/2008 | Bardwell et al. |
| 2008/0193943 A1 | 8/2008 | Murray |
| 2008/0199873 A1 | 8/2008 | Anderson et al. |
| 2008/0233567 A1 | 9/2008 | Murray |
| 2008/0287419 A1 | 11/2008 | Bruncko et al. |
| 2009/0149461 A1 | 6/2009 | Krivoshik |
| 2009/0176785 A1 | 7/2009 | Bardwell et al. |
| 2009/0318689 A1 | 12/2009 | Franczyk, II et al. |
| 2010/0028889 A1 | 2/2010 | Anderson et al. |
| 2010/0087436 A1 | 4/2010 | Bardwell et al. |
| 2010/0129357 A1 | 5/2010 | Garcia-Martinez et al. |
| 2010/0227838 A1 | 9/2010 | Shah et al. |
| 2010/0249133 A1 | 9/2010 | Bruncko et al. |
| 2010/0278921 A1 | 11/2010 | Fischer et al. |
| 2010/0280031 A1 | 11/2010 | David et al. |
| 2010/0297194 A1 | 11/2010 | Catron et al. |
| 2010/0305125 A1 | 12/2010 | Borchardt et al. |
| 2010/0310648 A1 | 12/2010 | Packhaeuser et al. |
| 2010/0311751 A1 | 12/2010 | Schmitt et al. |
| 2010/0323020 A1 | 12/2010 | Gokhale et al. |
| 2011/0071151 A1 | 3/2011 | Zhang et al. |
| 2011/0159085 A1 | 6/2011 | Tong et al. |
| 2011/0294811 A1 | 12/2011 | Zhang et al. |
| 2012/0121594 A1 | 5/2012 | Smith |
| 2012/0135429 A1 | 5/2012 | McKEEGAN et al. |
| 2012/0178632 A1 | 7/2012 | Mckeegan et al. |
| 2012/0288504 A1 | 11/2012 | Smith |
| 2012/0294852 A1 | 11/2012 | Smith |
| 2013/0028860 A1 | 1/2013 | Smith et al. |
| 2013/0034554 A1 | 2/2013 | Garcia-Martinez et al. |
| 2013/0101598 A1 | 4/2013 | Smith |
| 2013/0183264 A1 | 7/2013 | Smith |
| 2013/0183293 A1 | 7/2013 | Smith et al. |
| 2013/0224201 A1 | 8/2013 | Garcia-Martinez et al. |
| 2013/0324533 A1 | 12/2013 | Ruan et al. |
| 2014/0271459 A1 | 9/2014 | Dutzar et al. |
| 2014/0271464 A1 | 9/2014 | Garcia-Martinez et al. |
| 2014/0323421 A1 | 10/2014 | Klaus et al. |
| 2014/0377258 A1 | 12/2014 | Stern et al. |
| 2015/0182490 A1 | 7/2015 | Brown et al. |
| 2015/0273058 A1 | 10/2015 | Smith et al. |
| 2015/0274822 A1 | 10/2015 | Smith |
| 2015/0283142 A1 | 10/2015 | Stern et al. |
| 2015/0313906 A1 | 11/2015 | Creasy et al. |
| 2015/0337036 A1 | 11/2015 | Garcia-Martinez et al. |
| 2016/0101109 A1 | 4/2016 | Bardwell et al. |
| 2016/0102145 A1 | 4/2016 | Smith et al. |
| 2016/0113932 A1 | 4/2016 | Stern et al. |
| 2016/0115228 A1 | 4/2016 | Smith |
| 2016/0175316 A1 | 6/2016 | Bardwell et al. |
| 2016/0339019 A1 | 11/2016 | Laberge et al. |
| 2016/0355585 A1 | 12/2016 | Smith |
| 2017/0080010 A1 | 3/2017 | Klaus et al. |
| 2017/0107280 A1 | 4/2017 | Dutzar et al. |
| 2017/0115307 A1 | 4/2017 | Garcia-Martinez et al. |
| 2017/0189426 A1 | 7/2017 | Packhaeuser et al. |
| 2017/0196857 A1 | 7/2017 | Laberge et al. |
| 2017/0196858 A1 | 7/2017 | Laberge et al. |
| 2017/0198253 A1 | 7/2017 | Laberge et al. |
| 2017/0202782 A1 | 7/2017 | Pierce et al. |
| 2017/0209435 A1 | 7/2017 | Laberge et al. |
| 2017/0224680 A2 | 8/2017 | Laberge et al. |
| 2017/0326136 A1 | 11/2017 | David et al. |
| 2017/0348307 A1 | 12/2017 | Laberge et al. |
| 2017/0360795 A1 | 12/2017 | Stern et al. |
| 2017/0368036 A1 | 12/2017 | Hattersley et al. |
| 2018/0015093 A1 | 1/2018 | Stern et al. |
| 2018/0092999 A1 | 4/2018 | Garcia-Martinez et al. |
| 2018/0104222 A1 | 4/2018 | Childs et al. |
| 2018/0117038 A1 | 5/2018 | Laberge et al. |
| 2018/0117149 A1 | 5/2018 | Smith et al. |
| 2018/0201668 A1 | 7/2018 | Garcia-Martinez et al. |
| 2018/0221376 A1 | 8/2018 | Beeharry et al. |
| 2018/0235956 A1 | 8/2018 | Laberge et al. |
| 2018/0235957 A1 | 8/2018 | Laberge et al. |
| 2018/0250296 A1 | 9/2018 | Laberge et al. |
| 2018/0256568 A1 | 9/2018 | Laberge et al. |
| 2018/0303828 A1 | 10/2018 | Laberge et al. |
| 2019/0010225 A1 | 1/2019 | Smith |
| 2019/0022090 A1 | 1/2019 | Laberge et al. |
| 2019/0083521 A1 | 3/2019 | Klaus et al. |
| 2019/0083665 A1 | 3/2019 | Garcia-Martinez et al. |
| 2019/0085066 A1 | 3/2019 | Dutzar et al. |
| 2019/0085070 A1 | 3/2019 | Smith et al. |
| 2019/0134053 A1 | 5/2019 | Whitsett et al. |
| 2019/0169288 A1 | 6/2019 | Smith |
| 2019/0183948 A1 | 6/2019 | Yan et al. |
| 2019/0269675 A1 | 9/2019 | Chinta et al. |
| 2019/0269704 A1 | 9/2019 | Packhaeuser et al. |
| 2019/0343832 A1 | 11/2019 | Laberge et al. |
| 2020/0030323 A1 | 1/2020 | Laberge et al. |
| 2020/0054061 A1 | 2/2020 | Dischler |
| 2020/0061075 A1 | 2/2020 | Telci et al. |
| 2020/0108140 A1 | 4/2020 | Garcia-Martinez et al. |
| 2020/0171008 A1 | 6/2020 | Hattersley et al. |
| 2020/0246275 A1 | 8/2020 | Pierce et al. |
| 2020/0281925 A1 | 9/2020 | Ferretti et al. |
| 2020/0354446 A1 | 11/2020 | Smith et al. |
| 2021/0093649 A1 | 4/2021 | Packhaeuser et al. |

FOREIGN PATENT DOCUMENTS

| | | |
|---|---|---|
| WO | WO-2008064116 A2 | 5/2008 |
| WO | WO-2008070663 A2 | 6/2008 |
| WO | WO-2008082643 A2 | 7/2008 |
| WO | WO-2008082673 A2 | 7/2008 |
| WO | WO-2009064938 A1 | 5/2009 |
| WO | WO-2009073835 A1 | 6/2009 |
| WO | WO-2009155386 A1 | 12/2009 |
| WO | WO-2010065072 A1 | 6/2010 |
| WO | WO-2010065077 A2 | 6/2010 |
| WO | WO-2010065078 A1 | 6/2010 |
| WO | WO-2010065079 A2 | 6/2010 |
| WO | WO-2010127190 A1 | 11/2010 |
| WO | WO-2010127191 A1 | 11/2010 |
| WO | WO-2010127192 A1 | 11/2010 |
| WO | WO-2010127198 A1 | 11/2010 |
| WO | WO-2010143074 A2 | 12/2010 |
| WO | WO-2010144464 A2 | 12/2010 |
| WO | WO-2010147899 A1 | 12/2010 |
| WO | WO-2011034934 A1 | 3/2011 |
| WO | WO-2011066369 A2 | 6/2011 |
| WO | WO-2011066371 A2 | 6/2011 |
| WO | WO-2011066374 A2 | 6/2011 |
| WO | WO-2011066378 A2 | 6/2011 |
| WO | WO-2011079127 A1 | 6/2011 |
| WO | WO-2012082074 A1 | 6/2012 |
| WO | WO-2014004376 A2 | 1/2014 |
| WO | WO-2014071109 A1 | 5/2014 |
| WO | WO-2014100080 A1 | 6/2014 |
| WO | WO-2014153001 A1 | 9/2014 |
| WO | WO-2014153117 A2 | 9/2014 |
| WO | WO-2014153166 A2 | 9/2014 |
| WO | WO-2014194254 A1 | 12/2014 |
| WO | WO-2015095834 A2 | 6/2015 |
| WO | WO-2015116740 A1 | 8/2015 |
| WO | WO-2015157120 A1 | 10/2015 |
| WO | WO-2016043874 A2 | 3/2016 |
| WO | WO-2017223115 A1 | 12/2017 |
| WO | WO-2018022973 A1 | 2/2018 |
| WO | WO-2018033128 A1 | 2/2018 |
| WO | WO-2018178925 A1 | 10/2018 |
| WO | WO-2019054966 A2 | 3/2019 |
| WO | WO-2019178433 A1 | 9/2019 |
| WO | WO-2020061216 A1 | 3/2020 |
| WO | WO-2020092117 A2 | 5/2020 |
| WO | WO-2020128892 A1 | 6/2020 |

(56) References Cited

FOREIGN PATENT DOCUMENTS

| WO | WO-2020128894 A1 | 6/2020 |
|---|---|---|
| WO | WO-2020128898 A1 | 6/2020 |
| WO | WO-2020132184 A1 | 6/2020 |
| WO | WO-2020252218 A1 | 12/2020 |

OTHER PUBLICATIONS

Bose P., et al., "New Concepts of Treatment for Patients with Myelofibrosis," Current Treatment Options in Oncology, Jan. 2019, vol. 20 (1), pp. 1-25.
Brown J., et al., "Ongoing phase 1 studies of ABT-263; Pharmacokinetics, safety and antitumoractivity in patients with relapsed chronic lymphocytic leukemia (CLL)/small lymphocytic lymphoma (SLL)," Annals of Oncology, Sep. 2008, vol. 19 (Suppl.8), page viii229. Oxford University Press.
Chand H. S., et al., "A Small Molecule BCL-2 Inhibitor Switches IL-13 to a Cell Death Inducer for Allergen-Induced Metaplastic Mucous Cells," American Journal of Respiratory and Critical Care Medicine, 2014, Meeting Abstracts 189, American Thoracic Society.
Chiu Y., et al., "Advantages of a Modified Continual Reassessment Method (CRM) for Dose-Finding Studies: Experience in Ongoing Phase I Trials with ABT-263," European Journal of Cancer Supplements, 2008, vol. 12, p. 14.
Choi J.H., et al., "Targeting Apoptosis in Acute Myeloid Leukemia: Current Status and Future Directions of BCL-2 Inhibition with Venetoclax and Beyond," Targeted Oncology, Apr. 2020, vol. 15(2), pp. 147-162.
Choo E.F., et al., "The Role of Lymphatic Transport on the Systemic Bioavailability of the BCL-2 Protein Family Inhibitors Navitoclax (ABT-263) and ABT-199," Drug Metabolism and Disposition, Feb. 2014, vol. 42 (2), pp. 207-212.
Cleary J., et al.," A Phase I Clinical Trial of Navitoclax, a Targeted High-affinity Bcl-2 Family Inhibitor, in Combination With Gemcitabine in Patients With Solid Tumors," Investigational New Drugs, Oct. 2014, vol. 32 (5) pp. 937-945.
Cleary J. M., et al., "Combination Study of Navitoclax with Gemcitabine (G) in Patients (pts) with Solid Tumors," Journal of Clinical Oncology, May 20, 2011, vol. 29 (15), p. 3067.
Clinical Trial: A Study Evaluating Tolerability and Efficacy of Navitoclax Alone or in Combination With Ruxolitinib in Participants With Myelofibrosis (REFINE), Retrieved from the Internet: [URL: https://clinicaltrials.gov/ct2/show/NCT03222609], retrieved on Jan. 25, 2021.
Davids M. S., et al., "Overcoming Stroma-Mediated Treatment Resistance in Chronic Lymphocytic Leukemia Through BCL-2 Inhibition," Leukemia & Lymphoma, Aug. 2013, vol. 54(8), pp. 1823-1825.
De Vos S., et al., "Navitoclax (ABT-263) Safety and Efficacy in Patients with Relapsed or Refractory Lymphoid Malignancies: Preliminary Phase 2 Results from a Phase 1/2a Study," Haematologica, Jun. 1, 2011, vol. 96, pp. 152-153.
Diamanti P., et al., "Combining BCL-2 Inhibitors with Parthenolide to Treat Childhood Acute Lymphoblastic Leukaemia," Blood, Decemeber3, 2015, vol. 126(23), 2531.
Duan W., et al., "Fanconi Anemia Repair Pathway Dysfunction, a Potential Therapeutic Target in Lung Cancer," Frontiers in oncology, Dec. 2014, vol. 4, Article 368. pp. 1-8.
Ede B.C., et al., "A Novel Combination Therapy for Paediatric T Cell Acute Lymphoblastic Leukaemia," Blood, Decembers, 2015, vol. 126 (23), p. 3767.
Fairbrother W.J., et al., "Discovery and Development of Venetoclax, a Selective Antagonist of BCL-2," Successful Drug Discovery, Oct. 2019, vol. 4, pp. 225-245.
Friberg L.E., et al. "Model of Chemotherapy-induced Myelosuppression with Parameter Consistency Across Drugs," Journal of Clinical Oncology, Dec. 2002, vol. 20 (24), pp. 4713-4721.
Gandhi et al., "An ongoing phase 1 study of ABT-263 in patients with relapsed small cell lung cancer and other solid tumors," Annals of Oncology, Sep. 2008, vol. 19 (S8), page viiil 16, Oxford University Press.
Gandhi L., et al., "A phase 1 study of ABT-263 in patients with relapsed small cell lung cancer (SCLC) and other solid tumors,"Journal of Thoracic Oncology, Sep. 2009, vol. 4 (9 Supp 1),AbsD5-4.
Gandhi L., et al., "Phase I Study of Navitoclax (ABT-263), A Novel Bcl-2 Family Inhibitor, In Patients with Small-Cell Lung Cancer and Other Solid Tumors," Journal of Clinical Oncology, Mar. 1, 2011, vol. 29(7), pp. 909-916.
Gao L., et al., Combined BCL-2/XL and mTOR Inhibition Promotes Apoptosis in Small Cell Lung Cancer, Cancer Research, Oct. 2014, vol. 74 (19 Suppl), Abstract 5434.
Gao L., et al., "Sensitivity of Small Cell Lung Cancer Cells with Defective Fanconi Anemia (FA) Pathway to BCL2 Inhibitors," Cancer Research, Apr. 15, 2013, vol. 73 (Suppl. 8), Abstract 4365.
Gao L., et al., "Inhibition of Pro-survival Pathways in Lung Cancer Cells With Functional Defects in the Fanconi Anemia Pathway," Cancer Research, Aug. 2015, vol. 75 (15), Abstract 559.
Garman K., et al., "High Throughput Synergy Screening Identifies Therapeutic Combinations for Merkel Cell Carcinoma," Cancer Research, Aug. 2020, vol. 80 (16 Suppl), Abstract 4034.
Harrison C.N., et al., "Results From a Phase 2 Study of Navitoclax in Combination With Ruxolitinib in Patients With Primary or Secondary Myelofibrosis," Blood, Nov. 2019, vol. 134 (Suppl. 1), p. 671.
Herting F., et al., "Enhanced Activity of Ga101, a Novel Type Ii, Glycoengineered Cd20 Antibody, in Combination with Bendamustine Or Fludarabine, and with the Bcl-2 Family Inhibitors Abt-737 Or Abt-263," Blood, 2010, vol. 116, pp. abstract3915.
Hong Y., et al., "Senolytic Drug ABT-263 Enhances Cisplatin-and Til-induced Cell Death in Vitro but Has Limited in Vivo Activity in Preclinical Models of Head and Neck Cancer," Cancer Research, Aug. 2020, vol. 80 (16 suppl), Abstract 5830.
Humerickhouse R., et al., "Remarkable Early Clinical Activity with the Bcl-2 Selective Inhibitor ABT-199: Proving the Concept," Cancer Research, suppl. Apr. 15, 2013, vol. 73 (8), Abstract SY24-02.
International Search Report and Written Opinion for the Application No. PCT/US2020/058910, dated Feb. 5, 2021,13 pages.
Jabbour E., et al., "Venetoclax and Navitoclax in Relapsed or Refractory Acute Lymphoblastic Leukemia and Lymphoblastic Lymphoma," HemaSphere, Jun. 2020, vol. 4 (S1), pp. 9-10.
Javarappa K., et al., Eltrombopag Promotes Megakaryocyte Survival and Signaling in the Presence of Specific Cytotoxic Agents, Blood, Nov. 2018, p. 3836.
Kaefer A., et al., "Mechanism-based Pharmacokinetic/pharmacodynamic Meta-analysis of Navitoclax (ABT-263) Induced Thrombocytopenia," Cancer Chemother Pharmacology, Sep. 2014, vol. 74 (3), pp. 593-602.
Kahl B., et al., "Navitoclax (ABT-263) Plus Rituximab: Interim Results of a Phase 1 Study in Patients with CD20-Positive Lymphoid Malignancies," Blood, Nov. 19, 2010, vol. 116 (21), Abstract 3943.
Ketchem C.J., et al., "The Antiarrhythmic Drug, Amiodarone, Decreases AKT Activity and Sensitizes Human Acute Myeloid Leukemia Cells to Apoptosis by ABT-263," The American Journal of the Medical Sciences, 2018, 355(5) pp. 488-496.
Khan S., et al., DT2216, a Synthetic Proteolytic Selectively Targeting Bcl-XL for Ubiquitination and Degradation in Tumor Cells but Not in Platelets, Is a Saferand More Potent Antitumor Agent Than Navitoclax, Blood, Nov. 2018, vol. 132 (Suppl 1), 2698.
Kipps T., et al., "A Phase 2 Study of the BH3 Mimetic BCL2 Inhibitor Navitoclax (Abt-263) With or Without Rituximab, in Previously Untreated B-cell Chronic Lymphocytic Leukemia," Leukemia and Lymphoma, Oct. 2015, 56(10) pp. 2826-2833.
Kipps T., et al., "Navitoclax (ABT-263) Plus Fludarabine/Cyclophosphamide/Rituximab (FCR) or Bendamustine/Rituximab (Br): A Phase 1 Study in Patients with Relapsed/Refractory Chronic Lymphocytic Leukemia (CLL)," Haematologica, Jun. 2012, vol. 97 (219).

(56) References Cited

OTHER PUBLICATIONS

Kipps T.J., et al., "Navitoclax (ABT-263) plus Fludarabine/Cyclophosphamide/Rituximab (FCR) or Bendamustine/Rituximab (Br): A phase 1 study in patients with relapsed/refractory Chronic Lymphocytic Leukemia (CLL)," Blood, Nov. 2010, vol. 116 (21), American Society of Hematology.

Kipps T.J., et al., "Navitoclax (ABT-263) plus fludarabine/cyclophosphamide/rituximab (FCR) or bendamustine/rituximab (Br): A phase 1 study in patients with relapsed/refractory chronic lymphocytic leukemia (CLL)," Blood, Nov. 2011, vol. 118 (21), American Society of Hematology.

Koubek E.J., et al., "Pharmacokinetic analysis of navitoclax in combination with sorafenib in patients with relapsed or refractory solid organ tumors," Cancer Research, Aug. 2020, vol. 80 (16), Abstract CT114.

Kour S., et al., "CDK5 Inhibitor Downregulates Mcl-1 and Sensitizes Pancreatic Cancer Cell Lines to Navitoclax," Molecular Pharmacology, 2019, vol. 96 (4) pp. 419-429.

Koyama M., et al., "Low-dose Trametinib and Bcl-xl Antagonist Have a Specific Antitumor Effect in KRAS-Mutated Colorectal Cancer Cells," International Journal of Oncology, Nov. 2020,57(5) p. 1179-1191.

Lee J. M., et al., Navitoclax and Veliparib Yield Cytotoxicity With Lower Doses than Used for Single Agents in Women's Cancers, Molecular Cancer Therapeutics, 2013, vol. 12 (11).

Lee Y., et al., "Inhibition of EGFR Pathway Promotes the Cytotoxicity of ABT-263 in Human Leukemia K562Cells by Blocking MCL1 Upregulation," Biochemical Pharmacology, 2020, 178.

Lin Q., et al., "ABT-263 induces G(1)/G(0)-phase Arrest, Apoptosis and Autophagy in Human Esophageal Cancer Cells in Vitro," Acta Pharmacologica Sinica, Dec. 2017, vol. 38 (12) pp. 1632-1641.

Liu Z., et al., "Synergistic Effects of Bcl-2 Inhibitors With AZD9291 on Overcoming the Acquired Resistance of AZD9291 in H1975 Cells," Archives of Toxicology, 2020, vol. 94 (9) pp. 3125-3136.

McKeegan E., et al., "Exploratory patient (pt) stratification markers associated with sensitivity to ABT-263 in small cell lungcancer (SCLC)," Cancer Research, Apr. 2010, vol. 70 (8), Abstract 3738.

Natalie Y.L.N., et al., "Targeting Mitochondrial Apoptosis to Overcome Treatment Resistance in Cancer," Cancers, Mar. 2020, vol. 12 (3), p. 574.

O'Connor et al., "A phase 1 study evaluating the safety, PK &efficacy of ABT-263 in subjects with refractory or relapsed lymphoid malignancies," Ann.Oncol., 2008, vol. 19, Abs101.

Patwardhan G., et al.," A Systematic Investigation of the Effect of Scheduling of Targeted Combination Therapies on Response and Dynamics of Relapse in Triple Negative Breast Cancer Cells," Cancer Research, Jul. 2017, vol. 77 (13).

Roberts A., et al., "Phase 1 Study of the Safety, Pharmacokinetics, and Antitumour Activity of the Bcl2 Inhibitor Navitoclax in Combination With Rituximab in Patients With Relapsed or Refractory Cd20+ Lymphoid Malignancies," British journal of haematology, Sep. 2015, vol. 170 (5) pp. 669-678.

Roberts A.W., et al., "Substantial Susceptibility of Chronic Lymphocytic Leukemia to BCL2 Inhibition: Results of a Phase I Study of Navitoclax in Patients with Relapsed Or Refractory Disease," Journal of Clinical Oncology, 2012, vol. 30 (5), pp. 488-496.

Roberts et al., "An Ongoing Phase 1 Study of ABT-263; Pharmacokineties, Safety and AntiTumor Activity in Patients with Relapsed or Refractory Chronic Lymphocytic Leukemia (CLL)," Blood, Nov. 2008, vol. 112 (11), pp. 1089-1090.

Roberts et al., "An ongoing phase 1/2a study of ABT-263; pharmacokinetics (PK), safety and anti-tumor activity in patients (pts) with relapsed or refractory chronic lymphocytic leukemia (CLL)," Blood, Nov. 2009, vol. 114 (22), American Society of Hematology.

Roberts W., et al., "Phase 1 study of navitoclax (ABT-263) plus rituximab in CD20-positive lymphoid malignancies," Haematologica, Jun. 2010, vol. 95 (Suppl 2), p. 371.

Rocha-Lima C., et al., "Combination Study of Navitoclax (ABT-263) with Gemcitabine (G) in Patients (PTS) with Solid Tumors," Annals of Oncology, Oct. 2010, vol. 21, pp. viii181.

Rodansky E.S., et al., "The Bcl-2 Inhibitor Abt-263 Attenuates Intestinal Fibrosis in Human Intestinal Organoids and the Mouse S. Typhimurium Model," Gastroenterology, May 2019, vol. 156 (6 Suppl 1), page S194.

Rudin C.M., et al., "A phase IIa study of ABT-263 in patients with relapsed small-cell lung cancer (SCLC)," Journal of Clinical Oncology, May 2010, vol. 28 (Suppl. 1), p. 15, American Society of Clinical Oncology.

Salem A.M., et al., "Effect of Co-administration of Ketoconazole, a Strong Cyp3a Inhibitor, on the Pharmacokinetics, Safety and Tolerability of Navitoclax, a First-in-class Oral Bcl-2 Family Inhibitor, in Cancer Patients," Anticancer Research, Apr. 2014, vol. 34(4), pp. 2001-2006.

Schoenwaelder S. M., et al., "Bcl-XI Inhibitory BH3 Mimetics Can Induce a Transient Thrombocytopathy that Undermines the Hemostatic Function of Platelets," Journal of Thrombosis and Haemostasis, Jul. 2011, vol. 9, p. 63.

Seymour F., et al., "Phase-II Study of Navitoclax (ABT-263) Safety and Efficacy in Patients with Relapsed or Refractory Chronic Lymphocytic Leukemia (CLL): Interim Results," Haematologica, Jun. 1, 2011, vol. 96, p. 227.

Seymour J., et al., "Phase 2 Study of Navitoclax (ABT-263) Safety and Efficacy in Patients with Relapsed or Refractory Chronic Lymphocytic Leukemia: Interim Results," Clinical Lymphoma, Myeloma and Leukemia, Oct. 2011, vol. 11, pp. S258.

Shanja-Grabarz X., et al., "Rationally Designed Combination of Bh3 Mimetic and Direct Bax Activation Effectively Induces Apoptosis in Anaplastic Thyroid Cancer Cells," Annals of Surgical Oncology Supplement 2020, vol. 27, pp. S58.

Shoemaker A.R., et al., "Activity of the Bcl-2 Family Inhibitor ABT-263 in a Panel of Small Cell Lung Cancer Xenograft Models," Clinical Cancer Research , 2008, vol. 14 (11), pp. 3268-3277.

Shoemaker A.R., et al., "The Bcl-2 Family Inhibitor ABT-263 Shows Significant but Reversible Thrombocytopenia in Mice," Blood, Nov. 16, 2006, vol. 108 (11), Part 1, 329A.

Song C., et al., "Bcl-2 Phosphorylation Confers Resistance on Chronic Lymphocytic Leukaemia Cells to the BH3 Mimetics ABT-737, ABT-263 and ABT-199 by Impeding Direct Binding," British Journal of Pharmacology, 2016, vol. 173 (3) pp. 471-483.

Sullivan R., et al., "First in Human, Dose Escalation Trial of the Combination of Dabrafenib, Trametinib, and Navitoclax in Patients With BRAF Mutant Solid Tumors," Molecular Cancer Therapeutics, Jan. 2018, vol. 17(1).

Suryani S., et al., "Evaluation of the Bcl-2 Inhibitor Abt-199 in Xenograft Models of Acute Lymphoblastic Leukemia by the Pediatric Preclinical Testing Program," Cancer Research, Aug. 2015, vol. 75(15).

Tan N., et al., "Navitoclax Enhances the Efficacy of Taxanes in Non-Small Cell Lung Cancer Models," Clinical Cancer Research : An Official Journal of the American Association for Cancer Research, Mar. 15, 2011, vol. 17(6), pp. 1394-1404.

Tefferi A., et al., "Revised response criteria for myelofibrosis: International Working Group-Myeloproliferative Neoplasms Research and Treatment (IWG-MRT) and European LeukemiaNet (ELN) consensus report," Blood, Aug. 22, 2013, vol. 122 (8), pp. 1395-1398.

Thiele J., et al., "European Consensus on Grading Bone Marrow Fibrosis and Assessment of Cellularity," Haematologica, Aug. 2005, vol. 90 (8), pp. 1128-1132.

Tolcher A., et al., "Safety, Efficacy, and Pharmacokinetics of Navitoclax (Abt-263) in Combination With Erlotinib in Patients With Advanced Solid Tumors," Cancer Chemotherapy and Pharmacology, Nov. 2015, vol. 76 (5) pp. 1025-1032.

Tolcher A.W., et al., "Safety, Efficacy, and Pharmacokinetics of Navitoclax (Abt-263) in Combination With Irinotecan: Results of an Open-label, Phase 1 Study," Cancer Chemotherapy and Pharmacology, Nov. 2015, vol. 76 (5) pp. 1041-1049.

Tse, C. et al., "ABT-263: A Potent and Orally Bioavailable Bcl-2 Family Inhibitor," Cancer Research, 2008, vol. 68 (9), pp. 3421-3428—Including Supplementary Data.

(56) References Cited

OTHER PUBLICATIONS

Verhaegen M. E., et al., "Targeting Merkel Cell Carcinoma Dependence on Bcl-2 Family Members Promotes Efficient Cell Death in Vitro and in Vivo," Journal of Investigative Dermatology, May 2013, vol. 1 (133), pp. S71.

Verstovsek S., et al., "A Double-Blind, Placebo-Controlled Trial of Ruxolitinib for Myelofibrosis," The New England Journal of Medicine, Mar. 2012, vol. 366 (9), pp. 799-807.

Verstovsek S., et al., "Management of Cytopenias in Patients with Myelofibrosis Treated with Ruxolitinib and Effect of Dose Modifications on Efficacy Outcomes," Onco Targets anf Therapy, Dec. 17, 2013, vol. 7, pp. 13-21.

Vogler M., et al., "Diminished Sensitivity of Chronic Lymphocytic Leukemia Cells to ABT-737 and ABT-263 Due to Albumin Binding in Blood," Clinical Cancer Research, 2010, vol. 16 (16), pp. 4217-4225.

Wang et al.," ABT-263. Bcl-2 inhibitor, apoptosis inducer, oncolytic," Drugs of the Future, Oct. 2008, vol. 33 (10), pp. 829-837.

Wang L. C., et al., "Therapeutic Inhibition of Anti-Aapoptotic BCL-2 Family Proteins in a Murine Model of Lupus Nephritis," Arthritis and Rheumatism, Oct. 2013, vol. 10(65), pp. S241.

Wierda, "Pharmacokinetics, safety and anti-tumor activity of ABT-263 in Patients with relapsed or refractory chronic lymphocytic leukemia/small lymphocytic lymphoma," Haematologica, Jun. 2009, vol. 94 (2 Suppl), p. 138.

Wilson et al., "ABT-263 activity and safety in patients with relapsed or refractory lymphoid malignancies in particular chronic lymphocytic leukemia (CLL)/small lymphocytic lymphoma (SLL)," Journal of Clinical Oncology, May 2009, vol. 27 (15 Suppl 1), 8574, American Society of Clinical Oncology.

Wilson et al., "Phase 1 Study of ABT-263, a Bcl-2 Family Inhibitor, in Relapsed or Refractory Lymphoid Malignancies," Blood, Nov. 2008, vol. 112 (11), 734.

Wilson et al., "Phase 1/2a study of ABT-263 in relapsed or refractory lymphoid malignancies," Blood, Nov. 2009, vol. 114 (22), American Society of Hematology.

Wilson et al., "Phase 1/2A study of navitoclax (ABT-263) in relapsed or refractory lymphoid malignancies," Haematologica, 2010, vol. 95 (2), pp. 116-117.

WILSON H.W., et al., "A phase 1/2a study evaluating the safety, pharmacokinetics, and efficacy of ABT-263 in subjects with refractory or relapsed lymphoid malignancies," Blood, 2007, vol. 110(11), p. 412A.

Wilson W. H., et al., "Navitoclax, A Targeted High-Affinity Inhibitor of BCL-2, in Lymphoid Malignancies: A Phase 1 Doseescalation Study of Safety, Pharmacokinetics, Pharmacodynamics, and Antitumour Activity," The Lancet Oncology, Dec. 2010, vol. 11(12), pp. 1149-1159.

Witzens-Harig M., et al., "HTLV-1-associated Adult T Cell Leukemia Is Highly Susceptible to Navitoclax Due to Enhanced Bax Expression," International Journal of Cancer, Jan. 15, 2016, vol. 138(2) pp. 507-514.

Wu Z., et al., "The BET-Bromodomain Inhibitor JQ1 Synergized ABT-263 Against Colorectal Cancer Cells Through Suppressing c-Myc-induced miR-1271-5p Expression," Biomed.Pharmacother, 2017, vol. 95 pp. 1574-1579.

Xiong H., et al., "Ethical Considerations in Evaluating Targeted Anticancer Drug Candidates in Healthy Volunteers—Safety and Risk Assessments," Cancer Research, Apr. 15, 2011, vol. 71, p. 8.

Xiong H., et al., "Exposure-response (E-R) relationship in ABT-263-induced thrombocytopenia and the effect of platelet transfusion in dogs, Molecular Cancer Therapeutics," Molecular Cancer Therapeutics, Dec. 2009, vol. 8 (12), c126, American Association for Cancer Research Inc.

Xiong H., et al., "Studying Navitoclax, a Targeted Anticancer Drug, in Healthy Volunteers Ethical Considerations and Risk/benefit Assessments and Management," Anticancer Research, Jul. 2014, vol. 34 (7), pp. 3739-3746.

Yang J., et al., "Effect of Rifampin on the Pharmacokinetics, Safety and Tolerability of Navitoclax (ABT-263), a Dual Inhibitor of Bcl-2 and Bcl-XL , in Patients with Cancer," Journal of Clinical Pharmacy and Therapeutics, Dec. 2014, vol. 39 (6), pp. 680-684.

Yang J., et al., "Evaluating the Relative Bioavailability of a New Formulation of Navitoclax (ABT-263) in Both Cancer Patients and Healthy Volunteers," Cancer Research, Apr. 15, 2011, vol. 71, p. 8.

Yokohama T., et al., "Navitoclax (Nav) and BMN 673 Yield Cytotoxicity With Lower Doses Than Used for Single Agents in High-grade Serous Ovarian Cancer (HGSOC)," Cancer Research, Aug. 2015, vol. 75 (15).

Zannetti A., et al., "18F-FLT Pet/Ct to Guide Therapy with EGFR Antagonists and Bcl-xL Inhibitors in Non-Small Cell Lung Cancer," European Journal of Nuclear Medicine and Molecular Imaging, Oct. 2011, vol. 38, pp. S150.

Zannetti A., et al., "3'-Deoxy-3'-18F-Fluorothymidine PET/CT to Guide Therapy with Epidermal Growth Factor Receptor Antagonists and Bcl-xL Inhibitors in Non-Small Cell Lung Cancer," Journal of Nuclear Medicine, Mar. 1, 2012, vol. 53(3), pp. 443-450.

Zannetti A., et al., "Combined Imaging with 18F-FLT Pet/Ct and 99m-TC-HYNIC-Annexin V Spect for Personalized Therapy with EGFR Antagonists and BCL-xL Inhibitors in Non-Small Cell Lung Cancer," European Journal of Cancer, Nov. 2012, vol. 48 (81).

Zhao X., et al., "Survivin Inhibition is Critical for Bcl-2 Family Inhibitor, ABT-263 to Induce Apoptosis in Liver Cancer Cells," FASEB Journal, Apr. 2011, Meeting Astracts 25 FASEB.

Zhao X., et al., "Survivin Inhibition Is Critical for Bcl-2 Inhibitor-Induced Apoptosis in Hepatocellular Carcinoma Cells," PLoS One, Aug. 1, 2011, vol. 6(8), pp. e21980.

Zoeller J.J., et al., "Neutralization of BCL2/XL Enhances the Cytotoxicity of TDM1 in Vivo," Cancer Research, 2016, vol. 76 (4 Suppl), Abstract nr P4-14-02.

\* cited by examiner

DOSING REGIMENS FOR USE IN TREATING MYELOFIBROSIS AND MPN-RELATED DISORDERS WITH NAVITOCLAX

CROSS-REFERENCE TO RELATED APPLICATIONS

The present Application claims priority to U.S. Provisional Patent Application Ser. No. 62/930,951, filed Nov. 5, 2019 and to U.S. Provisional Patent Application Ser. No. 62/984,518, filed Mar. 3, 2020. The disclosures of both references are hereby incorporated by reference in their entireties.

FIELD OF THE INVENTION

This invention relates to methods for treating myelofibrosis and myeloproliferative neoplasm (MPN)-related disorders in a subject comprising administering to the subject specific doses of navitoclax, optionally in combination with a therapeutically effective amount of ruxolitinib.

BACKGROUND OF THE INVENTION

Myeloproliferative neoplasms or MPNs, are a group of rare, chronic blood cancers in which a person's bone marrow does not function properly, affecting blood-cell formation. People with MPNs experience an abnormal production of these blood cells, which can cause a host of symptoms and complications. Myelofibrosis (MF) is one such MPN characterized by bone marrow megakaryocytic proliferation, reticulin and/or collagen fibrosis, and presence of mutations of the Janus kinase 2 gene (JAK-2), thrombopoietin receptor gene (MPL), or the calreticulin gene. Myelofibrosis is characterized by constitutional symptoms, splenomegaly, an increased risk of transformation to acute myeloid leukemia (AML) and a shortened life expectancy. The median age at diagnosis is in the sixth decade and 90% of patients are diagnosed after the age of 40 years.

Ruxolitinib (e.g. JAKAFI®) is approved for the treatment of patients with primary myelofibrosis in the United States and European Union. Ruxolitinib induces improvement in splenomegaly and disease-related symptoms as compared to placebo or best available alternative therapy. However, therapy with ruxolitinib does not eradicate the malignant clones, is not known to improve bone marrow fibrosis, and patients who stop ruxolitinib rapidly become symptomatic again. Some patients do not respond to ruxolitinib, whereas others develop secondary resistance. For example, in patients suffering from intermediate or high-risk primary or secondary myelofibrosis; only approximately 40% of patients achieve a spleen volume reduction of ≥35% ($SVR_{35}$) with ruxolitinib monotherapy, and $SVR_{35}$, if it occurs, is typically only observed within the first 12 weeks of the commencement of ruxolitinib monotherapy. Current therapies other than hematopoietic stem cell transplantation are not able to control all the clinical manifestations of myelofibrosis. Therefore, new treatments for myelofibrosis (MF) and MPN-related disorders such as polycythemia vera (PCV), essential thrombocytopenia (ET), and CMML (chronic myelomonocytic leukemia are needed to address the current problems with ruxolitinib therapy, particularly for patients who are not responsive to ruxolitinib monotherapy.

Navitoclax (ABT-263) is a small-molecule BCL-2 family protein inhibitor that binds with high affinity (Ki≤1 nM) to BCL-XL, BCL-2, and BCL-W. By competitively binding to these proteins, navitoclax frees pro-apoptotic family members, thus triggering cell death by apoptosis in sensitive populations. Certain cancer cells are particularly sensitive to navitoclax. For example, navitoclax displays potent mechanism-based cytotoxicity ($EC_{50}$≤1 µM) against human tumor cell lines derived from small cell lung carcinomas and lymphoid malignancies. Navitoclax exhibits potent single agent activity against 10 of 22 cell lines consisting of multiple leukemia and lymphoma types spanning both B-cell and T-cell malignancies. Navitoclax and a different BCL-2 family protein inhibitor compound, ABT-737, have also shown cell killing activity against myeloproliferative neoplasm patient samples cultured ex vivo and myeloproliferative neoplasm-derived cell lines bearing the activating JAK-2 V617F mutation, which is common in polycythemia vera and myelofibrosis.

Aberrant JAK-2-STAT3/5 signaling has been linked to over-expression of the navitoclax resistance factor MCL-1, and JAK-2 inhibitors have been shown to reduce MCL-1 expression. Conversely, BCL-XL elevation has been associated with resistance to JAK-2 inhibitors, and navitoclax has shown the ability to overcome that resistance.

BCL-XL inhibition alone, achieved using a BCL-XL selective inhibitor (WEHI-539), was shown to be sufficient for overcoming resistance. ABT-737 has also shown an ability to block the proliferation of myeloproliferative neoplasm cells in long-term colony forming assays, which serve as an indicator of malignant precursor/stem cell survival and proliferation. For example, endogenous erythroid colonies representing malignant PV clones able to grow in the absence of erythropoietin were significantly inhibited in the presence of 500 nM ABT-737 and could be further suppressed when 100-300 nM ABT-737 was combined with a JAK-2 inhibitor. The addition of navitoclax to a JAK-2 inhibitor has also demonstrated efficacy in animal models of JAK-2-mutated malignancies—for example, significantly slowing the growth of tumors in mice bearing the Eµ-TEL-JAK-2 transgene or patient-derived xenograft (PDX) mice bearing JAK-2-mutated B-ALL cells. The combination was also superior to either agent alone in prolonging the survival of mice with JAK-2-mutated tumors, in some cases effecting cures.

In view of the advantages that result from administration of a BCL-2 family inhibitor combined with a JAK-2 inhibitor, the present inventors have discovered a combination and dosing therapy that will go beyond symptom relief and offer an impact on the underlying course of disease of myelofibrosis. The present inventors have discovered, for the first time in human patients, that administration of specific doses of navitoclax with specific doses of ruxolitinib, results in a clinically meaningful reduction in spleen volume, allelic burden, total symptom score (TSS) and, importantly, bone marrow fibrosis (BMF) with a manageable safety profile, thus establishing this combination as a potential treatment option.

BRIEF SUMMARY OF THE INVENTION

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib; wherein the treatment of the human subject results in a spleen volume reduction of at least 35%. In one aspect, the treatment of the human subject results in a spleen volume reduction of at least 35% ($SVR_{35}$) by week 24.

In another embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib of at least 10 mg; wherein the treatment of the human subject results in a spleen volume reduction of at least 35% ($SVR_{35}$).

In yet another embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib of at least 10 mg; wherein the treatment of the human subject results in a spleen volume reduction of at least 35% ($SVR_{35}$); wherein the therapeutically effective amount of navitoclax is administered once a day; and wherein the therapeutically effective amount of ruxolitinib is administered twice a day. In one aspect, the therapeutically effective amount of navitoclax is 100 mg. In another aspect, the therapeutically effective amount of navitoclax is 200 mg.

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib of at least 10 mg; wherein the treatment of the human subject results in a spleen volume reduction of at least 35% ($SVR_{35}$); wherein the therapeutically effective amount of navitoclax is administered once a day; wherein the therapeutically effective amount of ruxolitinib is administered twice a day; and wherein the human subject has been treated with a JAK-2 inhibitor prior to administering the therapeutically effective amount of navitoclax. In one aspect, the therapeutically effective amount of navitoclax is 100 mg; and the therapeutically effective amount of ruxolitinib is 10 mg. In another aspect, the therapeutically effective amount of navitoclax is 200 mg; and the therapeutically effective amount of ruxolitinib is 10 mg.

In another embodiment, a method for treatment of a human subject with myelofibrosis is provided, comprising administering a therapeutically effective amount of navitoclax selected from the group consisting of 50 mg, 100 mg, 200 mg, and 300 mg; in combination with administering a therapeutically effective amount of ruxolitinib; wherein the myelofibrosis is relapsed or refractory (R/R) myelofibrosis; and wherein the treatment of the human subject results a spleen volume reduction of at least 35%. In one aspect, the therapeutically effective amount of ruxolitinib is at least 10 mg.

In yet another embodiment, a method for treatment of a human subject with myelofibrosis is provided, comprising administering a therapeutically effective amount of navitoclax selected from the group consisting of 50 mg, 100 mg, 200 mg, and 300 mg; in combination with administering a therapeutically effective amount of ruxolitinib of at least 10 mg; wherein the myelofibrosis is relapsed or refractory myelofibrosis; and wherein the treatment of the human subject results a spleen volume reduction of at least 35% ($SVR_{35}$); wherein the therapeutically effective amount of navitoclax is administered once a day; and wherein the therapeutically effective amount of ruxolitinib is administered twice a day. In one aspect, the therapeutically effective amount of navitoclax is 100 mg. In another aspect, the therapeutically effective amount of navitoclax is 200 mg.

In one embodiment, a method for treatment of a human subject with myelofibrosis is provided, comprising administering a therapeutically effective amount of navitoclax selected from the group consisting of 50 mg, 100 mg, 200 mg, and 300 mg; in combination with administering a therapeutically effective amount of ruxolitinib; wherein the myelofibrosis is relapsed or refractory myelofibrosis; wherein the treatment of the human subject results a spleen volume reduction of at least 35% ($SVR_{35}$); and wherein the human subject has received at least one dose of ruxolitinib prior to administering a therapeutically effective amount of navitoclax.

In another embodiment, a method for treatment of a human subject with myelofibrosis is provided, comprising administering a therapeutically effective amount of navitoclax selected from the group consisting of 50 mg, 100 mg, 200 mg, and 300 mg; in combination with administering a therapeutically effective amount of ruxolitinib; wherein the myelofibrosis is relapsed or refractory myelofibrosis; wherein the treatment of the human subject results a spleen volume reduction of at least 35% ($SVR_{35}$); and wherein the human subject has received a dose of at least 10 mg ruxolitinib twice a day for 12 weeks prior to administering a therapeutically effective amount of navitoclax. In one aspect, the therapeutically effective amount of navitoclax is 100 mg. In another aspect, the therapeutically effective amount of navitoclax is 200 mg.

In yet another embodiment, a method for treatment of a human subject with myelofibrosis is provided, comprising administering a therapeutically effective amount of navitoclax selected from the group consisting of 50 mg, 100 mg, 200 mg, and 300 mg; in combination with administering a therapeutically effective amount of ruxolitinib; wherein the myelofibrosis is relapsed or refractory myelofibrosis; and wherein treatment of the human subject results in an improvement in a grade of bone marrow fibrosis relative to a baseline grade of bone marrow fibrosis. In one aspect, the therapeutically effective amount of ruxolitinib is at least 10 mg.

In still another embodiment, a method for treatment of a human subject with myelofibrosis is provided, comprising administering a therapeutically effective amount of navitoclax selected from the group consisting of 50 mg, 100 mg, 200 mg, and 300 mg; in combination with administering a therapeutically effective amount of ruxolitinib of at least 10 mg; wherein the myelofibrosis is relapsed or refractory myelofibrosis; wherein treatment of the human subject results in an improvement in a grade of bone marrow fibrosis relative to a baseline grade of bone marrow fibrosis; wherein the therapeutically effective amount of navitoclax is administered once a day; and wherein the ruxolitinib dose is administered twice a day. In one aspect, the therapeutically effective amount of navitoclax is 100 mg. In another aspect, the therapeutically effective amount of navitoclax is 200 mg.

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib; wherein the human subject has failed to achieve a spleen volume reduction of at least 35% prior to being administered navitoclax; and wherein the treatment of the human subject results in a spleen volume reduction of at least 35%.

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib; wherein an initial dose of therapeutically effective amount of navitoclax is 50 mg; wherein after at least 7 days the therapeutically effective amount of navitoclax is increased to a next higher dose of the therapeutically effective amount of navitoclax; and wherein the treatment of the human subject results in a spleen volume reduction of at least 35%.

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; in combination with administering a therapeutically effective amount of ruxolitinib; wherein the human subject has received at least one dose of ruxolitinib of more than 10 mg prior to administering the therapeutically effective amount of navitoclax; wherein the dose of ruxolitinib is reduced to the therapeutically effective amount of ruxolitinib of 10 mg after administering the therapeutically effective amount of navitoclax; and wherein the treatment of the human subject results in a spleen volume reduction of at least 35%.

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject once a day a therapeutically effective amount of navitoclax selected from the group consisting of 50 mg, 100 mg, 200 mg, and 300 mg; in combination with orally administering to the human subject twice a day a therapeutically effective amount of ruxolitinib; wherein following 24 weeks of said administering navitoclax in combination with ruxolitinib, the spleen volume of the human subject is reduced by at least 35%.

In one embodiment, a method for improving bone marrow fibrosis grade in a human subject with myelofibrosis or a myeloproliferative neoplasm (MPN)-related disorder who is refractory to treatment with a JAK-2 inhibitor is provided, comprising orally administering to the human subject once a day a therapeutically effective amount of navitoclax selected from the group consisting of 50 mg, 100 mg, 200 mg, and 300 mg; in combination with orally administering to the human subject twice a day a therapeutically effective amount of ruxolitinib; wherein following 24 weeks of said administering navitoclax in combination with ruxolitinib the bone marrow fibrosis grade of the human subject s is improved by at least one grade.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to $150 \times 10^9/L$, the effective amount of navitoclax comprises 200 mg once daily, and if the human subject has a baseline platelet count of less than $150 \times 10^9/L$, the effective amount of navitoclax comprises 100 mg once daily, escalated to 200 mg once daily after 7 days or more if the human subject has a platelet count greater than or equal to $75 \times 10^9/L$, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to $150 \times 10^9/L$, the effective amount of navitoclax comprises 200 mg once daily, and if the human subject has a baseline platelet count of less than $150 \times 10^9/L$, the effective amount of navitoclax comprises 100 mg once daily, escalated to 200 mg once daily after 7 days or more if the human subject has a platelet count greater than or equal to $75 \times 10^9/L$, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; and wherein the myelofibrosis comprises relapsed/refractory (R/R), intermediate or high-risk primary or secondary myelofibrosis, post-polycythemia vera or post-essential thrombocytopenia myelofibrosis.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to $150 \times 10^9/L$, the effective amount of navitoclax comprises 200 mg once daily, and if the human subject has a baseline platelet count of less than $150 \times 10^9/L$, the effective amount of navitoclax comprises 100 mg once daily, escalated to 200 mg once daily after 7 days or more if the human subject has a platelet count greater than or equal to $75 \times 10^9/L$, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; and wherein the effective amount of navitoclax is optionally modified or interrupted due to thrombocytopenia or neutropenia.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to $150 \times 10^9/L$, the effective amount of navitoclax comprises 200 mg once daily, and if the human subject has a baseline platelet count of less than $150 \times 10^9/L$, the effective amount of navitoclax comprises 100 mg once daily, escalated to 200 mg once daily after 7 days or more if the human subject has a platelet count greater than or equal to $75 \times 10^9/L$, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; wherein the effective amount of navitoclax is optionally modified or interrupted due to thrombocytopenia or neutropenia; and wherein (i) if the subject has a platelet count between 75×10$^9$/L and greater than or equal to 50×10$^9$/L the effective amount of navitoclax is optionally reduced; (ii) if the subject has a platelet count less than 50×10$^9$/L, the navitoclax is interrupted or discontinued until platelets levels stabilize above a level greater than or equal to 50×10$^9$/L; (iii) if the subject has an absolute neutrophil count (ANC) less than 1.0 but greater than 0.5×10$^9$/L, the subject is optionally supported with G-CSF or antibiotics until ANC is greater than 1.0×10$^9$/L; and (iv) if the subject has an absolute neutrophil count (ANC) less than 0.5×10$^9$/L, the subject is optionally supported with G-CSF or antibiotics until ANC is greater than 1.0×10$^9$/L and navitoclax is interrupted or discontinued until ANC is greater than 1.0×10$^9$/L.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to 150×10$^9$/L, the effective amount of navitoclax comprises 200 mg once daily, and if the human subject has a baseline platelet count of less than 150×10$^9$/L, the effective amount of navitoclax comprises 100 mg once daily, escalated to 200 mg once daily after 7 days or more if the human subject has a platelet count greater than or equal to 75×10$^9$/L, and (ii) the effective amount of ruxolitinib comprises 10 mg twice daily; wherein the effective amount of navitoclax is optionally increased to 300 mg once daily if the human subject fails to achieve spleen reduction volume of at least 35% (SVR$_{35}$) by week 24 of treatment; and wherein the effective amount of ruxolitinib is modified or interrupted due to thrombocytopenia.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to 150×10$^9$/L, the effective amount of navitoclax comprises 200 mg once daily, and if the human subject has a baseline platelet count of less than 150×10$^9$/L, the effective amount of navitoclax comprises 100 mg once daily, escalated to 200 mg once daily after 7 days or more if the human subject has a platelet count greater than or equal to 75×10$^9$/L, and (ii) if the human subject has a baseline platelet count of greater than 200×10$^9$/L, the effective amount of ruxolitinib comprises 20 mg twice daily, if the subject has a baseline platelet count between 100×10$^9$/L and 200×10$^9$/L, the effective amount of ruxolitinib comprises 15 mg twice daily, and if the subject has a baseline platelet count between 50×10$^9$/L to less than 100×10$^9$/L, the effective amount of ruxolitinib comprises 5 mg twice daily; wherein the effective amount of navitoclax is optionally increased to 300 mg once daily if the human subject fails to achieve spleen reduction volume of at least 35% (SVR$_{35}$) by week 24 of treatment.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to 150×10$^9$/L, the effective amount of navitoclax comprises 200 mg once daily, and if the human subject has a baseline platelet count of less than 150×10$^9$/L, the effective amount of navitoclax comprises 100 mg once daily, escalated to 200 mg once daily after 7 days or more if the human subject has a platelet count greater than or equal to 75×10$^9$/L, and (ii) if the human subject has a baseline platelet count of greater than 200×10$^9$/L, the effective amount of ruxolitinib comprises 20 mg twice daily, if the subject has a baseline platelet count between 100×10$^9$/L and 200×10$^9$/L, the effective amount of ruxolitinib comprises 15 mg twice daily, and if the subject has a baseline platelet count between 50×10$^9$/L to less than 100×10$^9$/L, the effective amount of ruxolitinib comprises 5 mg twice daily; wherein the effective amount of navitoclax is optionally increased to 300 mg once daily if the human subject fails to achieve spleen reduction volume of at least 35% (SVR$_{35}$) by week 24 of treatment; and wherein the myelofibrosis comprises relapsed/refractory (R/R), intermediate or high-risk primary or secondary myelofibrosis, post-polycythemia vera or post-essential thrombocytopenia myelofibrosis.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to 150×10$^9$/L, the effective amount of navitoclax comprises 200 mg once daily, and if the human subject has a baseline platelet count of less than 150×10$^9$/L, the effective amount of navitoclax comprises 100 mg once daily, escalated to 200 mg once daily after 7 days or more if the human subject has a platelet count greater than or equal to 75×10$^9$/L, and (ii) if the human subject has a baseline platelet count of greater than 200×10$^9$/L, the effective amount of ruxolitinib comprises 20 mg twice daily, if the subject has a baseline platelet count between 100×10$^9$/L and 200×10$^9$/L, the effective amount of ruxolitinib comprises 15 mg twice daily, and if the subject has a baseline platelet count between 50×10$^9$/L to less than 100×10$^9$/L, the effective amount of ruxolitinib comprises 5 mg twice daily; wherein the effective amount of navitoclax is optionally increased to 300 mg once daily if the human subject fails to achieve spleen reduction volume of at least 35% (SVR$_{35}$) by week 24 of treatment; and wherein the effective amount of navitoclax is optionally modified or interrupted due to thrombocytopenia or neutropenia.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to 150×10$^9$/L, the effective amount of navitoclax comprises 200 mg once daily, and if the human subject has a baseline platelet count of less than 150×10$^9$/L, the effective amount of navitoclax comprises 100 mg once daily, escalated to 200 mg once daily after 7 days or more if the human subject has a platelet count greater than or equal to 75×10$^9$/L, and (ii) if the human subject has a baseline platelet count of greater than 200×10$^9$/L, the effective amount of ruxolitinib comprises 20 mg twice daily, if the subject has a baseline platelet count between 100×10$^9$/L and 200×10$^9$/L, the effective amount of ruxolitinib comprises 15 mg twice daily, and if the subject has a baseline platelet count between 50×10$^9$/L to less than 100×10$^9$/L, the effective amount of ruxolitinib comprises 5 mg twice daily; wherein the effective amount of navitoclax is optionally increased to 300 mg once daily if the human subject fails to achieve spleen reduction volume of at least 35% (SVR$_{35}$) by week 24 of treatment; wherein the effective amount of navitoclax is optionally modified or interrupted due to thrombocytopenia or neutropenia; and wherein (i) if the subject has a platelet count between $75 \times 10^9$/L and greater than or equal to $50 \times 10^9$/L the effective amount of navitoclax is optionally reduced; (ii) if the subject has a platelet count less than $50 \times 10^9$/L, the navitoclax is interrupted or discontinued until platelets levels stabilize above a level greater than or equal to $50 \times 10^9$/L; (iii) if the subject has an absolute neutrophil count (ANC) less than 1.0 but greater than $0.5 \times 10^9$/L, the subject is optionally supported with G-CSF or antibiotics until ANC is greater than $1.0 \times 10^9$/L; and (iv) if the subject has an absolute neutrophil count (ANC) less than $0.5 \times 10^9$/L, the subject is optionally supported with G-CSF or antibiotics until ANC is greater than $1.0 \times 10^9$/L and navitoclax is interrupted or discontinued until ANC is greater than $1.0 \times 10^9$/L.

In one embodiment, a method for treatment of myelofibrosis in a human subject in need thereof is provided, comprising orally administering to said subject an effective amount of navitoclax in combination with an effective amount of ruxolitinib, wherein (i) if the human subject has a baseline platelet count of greater than or equal to $150 \times 10^9$/L, the effective amount of navitoclax comprises 200 mg once daily, and if the human subject has a baseline platelet count of less than $150 \times 10^9$/L, the effective amount of navitoclax comprises 100 mg once daily, escalated to 200 mg once daily after 7 days or more if the human subject has a platelet count greater than or equal to $75 \times 10^9$/L, and (ii) if the human subject has a baseline platelet count of greater than $200 \times 10^9$/L, the effective amount of ruxolitinib comprises 20 mg twice daily, if the subject has a baseline platelet count between $100 \times 10^9$/L and $200 \times 10^9$/L, the effective amount of ruxolitinib comprises 15 mg twice daily, and if the subject has a baseline platelet count between $50 \times 10^9$/L to less than $100 \times 10^9$/L, the effective amount of ruxolitinib comprises 5 mg twice daily; wherein the effective amount of navitoclax is optionally increased to 300 mg once daily if the human subject fails to achieve spleen reduction volume of at least 35% ($SVR_{35}$) by week 24 of treatment; and wherein the effective amount of ruxolitinib is modified or interrupted due to thrombocytopenia.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150 \times 10^9$/L, the effective amount of navitoclax comprises 200 mg once daily, and if the human subject has a baseline platelet count of less than $150 \times 10^9$/L, the effective amount of navitoclax comprises 100 mg once daily, escalated to 200 mg once daily after 7 days or more if the human subject has a platelet count greater than or equal to $75 \times 10^9$/L, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150 \times 10^9$/L, the effective amount of navitoclax comprises 200 mg once daily, and if the human subject has a baseline platelet count of less than $150 \times 10^9$/L, the effective amount of navitoclax comprises 100 mg once daily, escalated to 200 mg once daily after 7 days or more if the human subject has a platelet count greater than or equal to $75 \times 10^9$/L, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; and wherein the myelofibrosis comprises relapsed/refractory (R/R), intermediate or high-risk primary or secondary myelofibrosis, post-polycythemia vera or post-essential thrombocytopenia myelofibrosis.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150 \times 10^9$/L, the effective amount of navitoclax comprises 200 mg once daily, and if the human subject has a baseline platelet count of less than $150 \times 10^9$/L, the effective amount of navitoclax comprises 100 mg once daily, escalated to 200 mg once daily after 7 days or more if the human subject has a platelet count greater than or equal to $75 \times 10^9$/L, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; and wherein the effective amount of navitoclax is optionally modified or interrupted due to thrombocytopenia or neutropenia.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150 \times 10^9$/L, the effective amount of navitoclax comprises 200 mg once daily, and if the human subject has a baseline platelet count of less than $150 \times 10^9$/L, the effective amount of navitoclax comprises 100 mg once daily, escalated to 200 mg once daily after 7 days or more if the human subject has a platelet count greater than or equal to $75 \times 10^9$/L, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; wherein the effective amount of navitoclax is optionally modified or interrupted due to thrombocytopenia or neutropenia; and wherein (i) if the subject has a platelet count between $75 \times 10^9$/L and greater than or equal to $50 \times 10^9$/L the effective amount of navitoclax is optionally reduced; (ii) if the subject has a platelet count less than $50 \times 10^9$/L, the navitoclax is interrupted or discontinued until platelets levels stabilize above a level greater than or equal to $50 \times 10^9$/L; (iii) if the subject has an absolute neutrophil count (ANC) less than 1.0 but greater than $0.5 \times 10^9$/L, the subject is optionally supported with G-CSF or antibiotics until ANC is greater than $1.0 \times 10^9$/L; and (iv) if the subject has an absolute neutrophil count (ANC) less than $0.5 \times 10^9$/L, the subject is optionally supported with G-CSF or antibiotics until ANC is greater than $1.0 \times 10^9$/L and navitoclax is interrupted or discontinued until ANC is greater than $1.0 \times 10^9$/L.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150\times10^9$/L, the effective amount of navitoclax comprises 200 mg once daily, and if the human subject has a baseline platelet count of less than $150\times10^9$/L, the effective amount of navitoclax comprises 100 mg once daily, escalated to 200 mg once daily after 7 days or more if the human subject has a platelet count greater than or equal to $75\times10^9$/L, and (ii) the effective amount of ruxolitinib comprises 10 mg twice daily; wherein the effective amount of navitoclax is optionally increased to 300 mg once daily if the human subject fails to achieve spleen reduction volume of at least 35% ($SVR_{35}$) by week 24 of treatment; and wherein the effective amount of ruxolitinib is modified or interrupted due to thrombocytopenia.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150\times10^9$/L, the effective amount of navitoclax comprises 200 mg once daily, and if the human subject has a baseline platelet count of less than $150\times10^9$/L, the effective amount of navitoclax comprises 100 mg once daily, escalated to 200 mg once daily after 7 days or more if the human subject has a platelet count greater than or equal to $75\times10^9$/L, and (ii) if the human subject has a baseline platelet count of greater than $200\times10^9$/L, the effective amount of ruxolitinib comprises 20 mg twice daily, if the subject has a baseline platelet count between $100\times10^9$/L and $200\times10^9$/L, the effective amount of ruxolitinib comprises 15 mg twice daily, and if the subject has a baseline platelet count between $50\times10^9$/L to less than $100\times10^9$/L, the effective amount of ruxolitinib comprises 5 mg twice daily; wherein the effective amount of navitoclax is optionally increased to 300 mg once daily if the human subject fails to achieve spleen reduction volume of at least 35% ($SVR_{35}$) by week 24 of treatment.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150\times10^9$/L, the effective amount of navitoclax comprises 200 mg once daily, and if the human subject has a baseline platelet count of less than $150\times10^9$/L, the effective amount of navitoclax comprises 100 mg once daily, escalated to 200 mg once daily after 7 days or more if the human subject has a platelet count greater than or equal to $75\times10^9$/L, and (ii) if the human subject has a baseline platelet count of greater than $200\times10^9$/L, the effective amount of ruxolitinib comprises 20 mg twice daily, if the subject has a baseline platelet count between $100\times10^9$/L and $200\times10^9$/L, the effective amount of ruxolitinib comprises 15 mg twice daily, and if the subject has a baseline platelet count between $50\times10^9$/L to less than $100\times10^9$/L, the effective amount of ruxolitinib comprises 5 mg twice daily; wherein the effective amount of navitoclax is optionally increased to 300 mg once daily if the human subject fails to achieve spleen reduction volume of at least 35% ($SVR_{35}$) by week 24 of treatment; and wherein the myelofibrosis comprises relapsed/refractory (R/R), intermediate or high-risk primary or secondary myelofibrosis, post-polycythemia vera or post-essential thrombocytopenia myelofibrosis.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150\times10^9$/L, the effective amount of navitoclax comprises 200 mg once daily, and if the human subject has a baseline platelet count of less than $150\times10^9$/L, the effective amount of navitoclax comprises 100 mg once daily, escalated to 200 mg once daily after 7 days or more if the human subject has a platelet count greater than or equal to $75\times10^9$/L, and (ii) if the human subject has a baseline platelet count of greater than $200\times10^9$/L, the effective amount of ruxolitinib comprises 20 mg twice daily, if the subject has a baseline platelet count between $100\times10^9$/L and $200\times10^9$/L, the effective amount of ruxolitinib comprises 15 mg twice daily, and if the subject has a baseline platelet count between $50\times10^9$/L to less than $100\times10^9$/L, the effective amount of ruxolitinib comprises 5 mg twice daily; wherein the effective amount of navitoclax is optionally increased to 300 mg once daily if the human subject fails to achieve spleen reduction volume of at least 35% ($SVR_{35}$) by week 24 of treatment; and wherein the effective amount of navitoclax is optionally modified or interrupted due to thrombocytopenia or neutropenia.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150\times10^9$/L, the effective amount of navitoclax comprises 200 mg once daily, and if the human subject has a baseline platelet count of less than $150\times10^9$/L, the effective amount of navitoclax comprises 100 mg once daily, escalated to 200 mg once daily after 7 days or more if the human subject has a platelet count greater than or equal to $75\times10^9$/L, and (ii) if the human subject has a baseline platelet count of greater than $200\times10^9$/L, the effective amount of ruxolitinib comprises 20 mg twice daily, if the subject has a baseline platelet count between $100\times10^9$/L and $200\times10^9$/L, the effective amount of ruxolitinib comprises 15 mg twice daily, and if the subject has a baseline platelet count between $50\times10^9$/L to less than $100\times10^9$/L, the effective amount of ruxolitinib comprises 5 mg twice daily; wherein the effective amount of navitoclax is optionally increased to 300 mg once daily if the human subject fails to achieve spleen reduction volume of at least 35% ($SVR_{35}$) by week 24 of treatment; wherein the effective amount of navitoclax is optionally modified or interrupted due to thrombocytopenia or neutropenia; and wherein (i) if the subject has a platelet count between $75\times10^9$/L and greater than or equal to $50\times10^9$/L the effective amount of navitoclax is optionally reduced; (ii) if the subject has a platelet count less than $50\times10^9$/L, the navitoclax is interrupted or discontinued until platelets levels stabilize above a level greater than or equal to $50\times10^9$/L; (iii) if the subject has an absolute neutrophil count (ANC) less than 1.0 but greater than $0.5\times10^9$/L, the subject is optionally supported with G-CSF or antibiotics until ANC is greater than $1.0\times10^9$/L; and (iv) if the subject has an absolute neutrophil count (ANC) less than $0.5\times10^9$/L, the subject is optionally supported with G-CSF or antibiotics until ANC is greater than $1.0×10^9$/L and navitoclax is interrupted or discontinued until ANC is greater than $1.0×10^9$/L.

In one embodiment, a method for treatment of myelofibrosis in a human subject in need thereof is provided, comprising (a) obtaining a baseline platelet count from said human subject; and (b) orally administering to said subject an effective amount of navitoclax in combination with an effective amount of ruxolitinib, wherein (i) if the human subject has a baseline platelet count of greater than or equal to $150×10^9$/L, the effective amount of navitoclax comprises 200 mg once daily, and if the human subject has a baseline platelet count of less than $150×10^9$/L, the effective amount of navitoclax comprises 100 mg once daily, escalated to 200 mg once daily after 7 days or more if the human subject has a platelet count greater than or equal to $75×10^9$/L, and (ii) if the human subject has a baseline platelet count of greater than $200×10^9$/L, the effective amount of ruxolitinib comprises 20 mg twice daily, if the subject has a baseline platelet count between $100×10^9$/L and $200×10^9$/L, the effective amount of ruxolitinib comprises 15 mg twice daily, and if the subject has a baseline platelet count between $50×10^9$/L to less than $100×10^9$/L, the effective amount of ruxolitinib comprises 5 mg twice daily; wherein the effective amount of navitoclax is optionally increased to 300 mg once daily if the human subject fails to achieve spleen reduction volume of at least 35% ($SVR_{35}$) by week 24 of treatment; and wherein the effective amount of ruxolitinib is modified or interrupted due to thrombocytopenia.

DETAILED DESCRIPTION OF THE INVENTION

Figure 1:
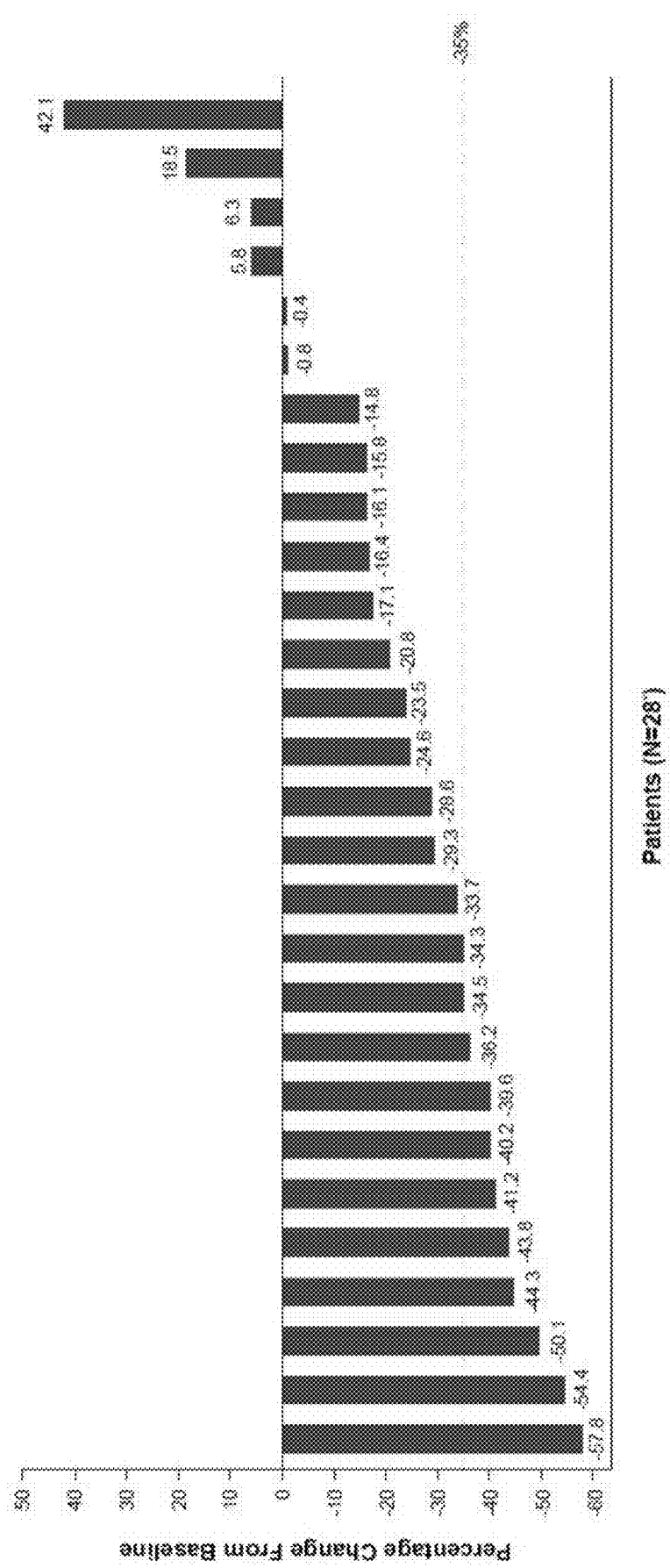
FIG. 1 is a waterfall plot describing percent change from baseline in spleen volume at week 24 as described in Example 1. As shown, 29% of patients achieved $SVR_{35}$ at week 24.

A Phase 2 clinical study was completed to evaluate the effect of the addition of navitoclax to ruxolitinib in subjects with primary or secondary myelofibrosis (Example 1 supra), and two Phase 3 clinical studies are underway, evaluating the combination of navitoclax with myelofibrosis in both JAK2 inhibitor naïve patients (Example 4) and in the relapsed or refractory (R/R) setting (Example 5). As shown in Example 1, after 24 weeks of treatment with navitoclax and ruxolitinib, 29% of subjects achieved a spleen volume reduction ≥35% ($SVR_{35}$), and 54% of subjects achieved >50% reduction of the spleen length (cm, below costal margin) as assessed by palpation. Additionally, spleen responses deepened beyond 24 weeks of treatment, and the best overall $SVR_{35}$ was further improved to 42%, with 79% of subjects achieving reductions in spleen length by palpation of >50%. Allelic frequency reductions >5% were observed in 42% of subjects, and reductions in bone marrow fibrosis of ≥1 grade were observed in 25% of subjects, suggesting this drug combination may be disease modifying.

Currently, ruxolitinib is the only targeted therapy approved and is considered the standard of care for the treatment of patients with intermediate or high-risk myelofibrosis. Ruxolitinib monotherapy has shown clinical benefit in improving splenomegaly and symptoms in subjects with intermediate or high-risk primary or secondary myelofibrosis; however, a significant unmet medical need still exists as only approximately 40% of patients achieve a spleen volume reduction of ≥35% ($SVR_{35}$) and these improvements are typically only observed within the first 12 weeks of administration if they are to occur at all (Verstovsek S, Mesa R, Gotlib J, et al. A Double-Blind, Placebo-Controlled Trial of Ruxolitinib for Myelofibrosis. N Engl J Med. 2012; 366(9): 799-807, hereby incorporated by reference in its entirety). Allogeneic transplantation is the only known curative treatment for myelofibrosis; however, that is only feasible in younger and medically fit patients and is associated with substantial morbidity and mortality. The present invention presents a new option for myelofibrosis treatment, particularly for patients who are refractory to ruxolitinib monotherapy, because a majority of patients do not achieve $SVR_{35}$ with ruxolitinib monotherapy, but 42% of patients achieve $SVR_{35}$ while receiving a combination of navitoclax with ruxolitinib even in patients who do not achieve $SVR_{35}$ with ruxolitinib monotherapy.

The present disclosure relates to methods for treatment of a human subject with myelofibrosis or an MPN-related disorder such as polycythemia vera (PCV), essential thrombocytopenia (ET), or chronic monomyelocytic leukemia (CMML), comprising administering a therapeutically effective amount of specific doses of navitoclax in combination with a therapeutically effective amount of ruxolitinib. In some embodiments, pre-dosing of ruxolitinib or another JAK2 inhibitor begins at least twelve weeks prior to administering navitoclax, followed by administration of a therapeutically effective amount of navitoclax.

Navitoclax

Navitoclax (also known as ABT-263) is a novel small-molecule BCL-2 family protein inhibitor that binds with high affinity ($K_i$≤1 nM) to BCL-XL, BCL-2, and BCL-W. Navitoclax has a CAS Registry Number of 923564-51-6; has an empirical formula of $C_{47}H_{55}ClF_3N_5O_6S_3$; a gram molecular weight of 974.61; and is described in U.S. Pat. No. 7,390,799, published Feb. 1, 2007, hereby incorporated by reference in its entirety.

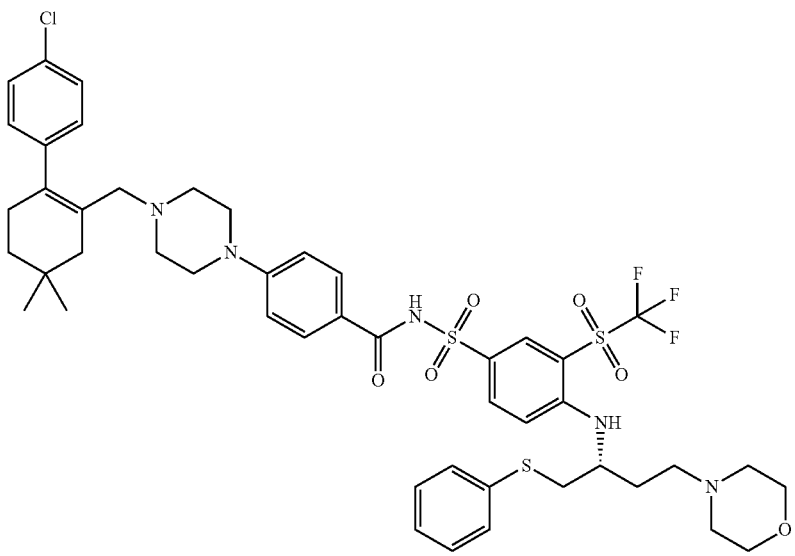 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]

Chemical Structure of Navitoclax

Use of the term "4-(4-{[2-(4-chlorophenyl)-5,5-dimethyl-1-cyclohexen-1-yl]methyl-}-piperazinyl)-N-[(4-{[(2R)-4-(4-morpholinyl)-1-(phenyl sulfanyl)-2-butanyl]amino}-3-[(trifluoromethyl)sulfonyl]phenyl)sulfonyl]benzamide" or "N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide" encompasses (unless otherwise indicated) solvates (including hydrates) and polymorphic forms of navitoclax or its salts. Pharmaceutical compositions of "4-(4-{[2-(4-chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl)sulfonyl] phenyl)sulfonyl]benzamide" or "N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenyl sulfanyl)methyl)propyl)amino)-3-((trifluoromethyl)sulfonyl)benzenesulfonamide" include all pharmaceutically acceptable compositions comprising "4-(4-{[2-(4-chlorophenyl)-5,5-dimethyl-1-cyclohexen-1-yl] methyl}-1-piperazinyl)-N-[(4-{[(2R)-4-(4-morpholinyl)-1-(phenyl sulfanyl)-2-butanyl]amino}-3-[(trifluoromethyl)sulfonyl]phenyl)sulfonyl]benzamide" or "N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide" and one or more diluents, vehicles and/or excipients.

Recommended Navitoclax Dosage Regimen for Myelofibrosis

The recommended starting dose of navitoclax for most patients with a baseline platelet count ≥150×10$^9$/L is 200 mg navitoclax once daily. For subjects with a baseline platelet count ≤150×10$^9$/L, the recommended starting dose is 100 mg navitoclax once daily. See Table 1 below. Further dose modifications based on toxicities after starting navitoclax are described in Table 2 below. Mechanism of action for navitoclax-induced thrombocytopenia can be found at Kaefer et al., Cancer Chemother Pharmacol (2014) 74:593-602, hereby incorporated by reference in its entirety. Additionally, at the discretion of the physician or prescribing agent, patients may increase dosage of navitoclax up to 300 mg once daily for subjects with suboptimal spleen response, e.g. a failure to achieve SVR$_{35}$ by week 24. Subjects should be instructed to take navitoclax tablets, preferably with a meal and water, at approximately the same time each day. Navitoclax tablets should be swallowed whole and not chewed, crushed, or broken prior to swallowing. Bioavailability and food effect of navitoclax in healthy volunteers can be found at Xiong et al., Anticancer Research 34: 3739-3746 (2014), hereby incorporated by reference in its entirety.

TABLE 1

Recommended Starting Dose for Navitoclax for Myelofibrosis

| Platelet count | Starting Dose | Escalation |
|---|---|---|
| (>150 × 10$^9$/L) | 200 mg | n/a |
| (≤150 × 10$^9$/L) | 100 mg | 200 mg (after approximately 7 or more days provided the platelet count is ≥75 × 10$^9$/L) |

TABLE 2

Recommended Navitoclax Dose Modifications for Toxicities

| Event | | Action |
|---|---|---|
| Thrombocytopenia | ≥75 × 10$^9$/L | Maintain current dose of navitoclax. Platelet count should be rechecked approximately 7 days after navitoclax dose increase. |
| | <75 × 10$^9$/L – ≥50 × 10$^9$/L | Maintain current navitoclax dose or consider dose reduction. Platelet count should be rechecked approximately every 7 days until ≥2 consecutive lab values indicate stable platelet count. |

TABLE 2-continued

Recommended Navitoclax Dose Modifications for Toxicities

| Event | | Action |
|---|---|---|
| | $<50 \times 10^9/L$ | Interrupt navitoclax. Recheck platelets every 2-3 days until recovery to ≥50 $10^9/L$. Then resume navitoclax at a lower dose. Platelet count should be rechecked approximately every 7 days until ≥2 consecutive lab values indicate stable platelet count. |
| Grade 3 neutropenia | ANC <1.0 – 0.5 × $10^9/L$ | Monitor neutrophils at least weekly until ANC >1.0 × $10^9/L$. Support with G-CSF and/or prophylaxis with antibiotics if clinically indicated. |
| Grade 4 neutropenia | ANC <0.5 × $10^9/L$ | Interrupt navitoclax. Monitor neutrophils at least weekly until ANC > 1.0 × $10^9/L$. Support with G-CSF and/or prophylaxis with antibiotics if clinically indicated. Reinitiate navitoclax at a lower dose upon recover of ANC > 1.0 × $10^9/L$. |

If a subject misses a dose of navitoclax within 8 hours of the time it is usually taken, the subject should take the missed dose as soon as possible and resume the normal daily dosing schedule. If a subject misses a dose by more than 8 hours, the subject should not take the missed dose and should resume the usual dosing schedule the next day.

If a subject vomits following dosing no additional dose should be taken that day. The next prescribed dose should be taken at the usual time.

Dose Modifications for Use with CYP3A Inhibitors/Inducers

Co-administration of navitoclax with CYP3A4 inhibitors or inducers or P-gp inhibitors should be undertaken with caution. For example, prescribing agents should consider modifying the dosage of navitoclax and/or a CYP3A4 inhibitor when co-administered with strong CYP3A4 inhibitors, or avoid co-administration with strong CYP3A4 inhibitors altogether, such as by discontinuing navitoclax for the duration of treatment with the strong CYP3A4 inhibitor. Increased dosage should be made with frequent monitoring of safety and efficacy. Co-administration of 400 mg once daily ketoconazole, a strong CYP3A, P-gp and BCRP inhibitor, in 10 subjects with cancer increased navitoclax $AUC_\infty$ by 1.55-fold, and had no impact on $C_{max}$. Co-administration of 600 mg once daily rifampin, a strong CYP3A inducer, for 4 days in 11 subjects with cancer decreased navitoclax $C_{max}$ by 16% and $AUC_\infty$ by 41%. In a combination study of navitoclax with paclitaxel alone or carboplatin/paclitaxel in subjects with solid tumors, navitoclax had negligible effect (<13% change) on $C_{max}$ and AUC of paclitaxel and its metabolite, 6-α-hydroxypaclitaxel whose formation is primarily mediated by CYP28 enzyme. Effects of navitoclax with CYP3A4 inhibitors in patients with cancer are described at Yang et al., Journal of Clinical Pharmacy and Therapeutics, 2014, 39, 680-684, hereby incorporated by reference in its entirety.

Ruxolitinib

As known in the art, ruxolitinib, a dual JAK1 and JAK2 inhibitor, has a CAS Registry Number of 1092939-17-7; has an empirical formula of $C_{17}H_{18}N_6 \cdot H_3PO_4$; and a gram molecular weight of 404.36.

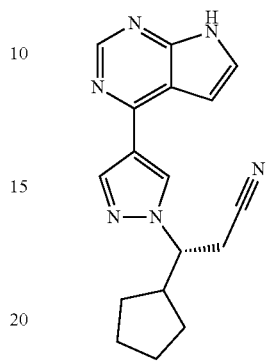

Chemical Structure of Ruxolitinib

Use of the term "(R)-3-(4-(7H-pyrrolo[2,3-d]pyrimidin-4-yl)-1H-pyrazol-1-yl)-3-cyclopentylpropanenitrile" or "(3R)-3-cyclopentyl-3-[4-(7H-pyrrolo[2,3-d]pyrimidin-4-yl)pyrazol-1-yl]propanenitrile", or "(3R)-3-cyclopentyl-3-[4-(7H-pyrrolo[2,3-d]pyrimidin-4-yl)-1H-pyrazol-1-yl]propanenitrile" encompasses (unless otherwise indicated) the free base, solvates (including hydrates), and polymorphic forms of ruxolitinib or its salts. Pharmaceutical compositions of ruxolitinib include all pharmaceutically acceptable compositions comprising ruxolitinib or ruxolitinib phosphate, and one or more diluents, vehicles and/or excipients.

One example of a pharmaceutical composition comprising ruxolitinib phosphate is JAKAFI® (Incyte). JAKAFI® tablets contains ruxolitinib phosphate equivalent to 5 mg, 10 mg, 15 mg, 20 mg and 25 mg of ruxolitinib free base together with inactive ingredients microcrystalline cellulose, lactose monohydrate, magnesium stearate, colloidal silicon dioxide, sodium starch glycolate, povidone and hydroxypropyl cellulose.

Suggested starting doses per indication are below, and doses of JAKAFI® should be individualized based on safety and efficacy.

For myelofibrosis, the FDA-approved starting dose of JAKAFI® is based on patient's baseline platelet count as follows: if baseline platelet count greater than $200 \times 10^9/L$, then 20 mg is given orally twice daily; if baseline platelet count is $100 \times 10^9/L$ to $200 \times 10^9/L$, then 15 mg given orally twice daily; and if baseline platelet count is $50 \times 10^9/L$ to less than $100 \times 10^9/L$, then 5 mg is given orally twice daily. Complete blood counts should be monitored every 2 to 4 weeks until doses are stabilized, and then monitored as clinically indicated. Dosing should be modified or interrupted for thrombocytopenia.

For polycythemia vera, the FDA-approved starting dose of JAKAFI® is 10 mg given orally twice daily.

For acute graft versus host disease, the FDA-approved starting dose of JAKAFI® is 5 mg given orally twice daily.

JAKAFI® is FDA-approved for treatment of intermediate or high-risk myelofibrosis (MF), including primary MF, post-polycythemia vera MF and post-essential thrombocythemia MF in adults. JAKAFI® is also indicated for treatment of polycythemia vera, and for treatment of polycythemia vera (PV) in adults who have had an inadequate response to or are intolerant of hydroxyurea.

The following section of the present disclosure relates to the FDA-approved dosing regimens for JAKAFI®, which is one example of a commercial formulation containing ruxolitinib. This section and its contents are not meant to be limiting in any way and are intended to supplement the Examples and the embodiments/disclosure of the inventions disclosed herein. For example, the dose/dosing regimens for JAKAFI®, including but not limited to dose/dosing regimen modifications related to, e.g., thrombocytopenia, neutropenia, hepatic and/or renal impairment disclosed below, for myelofibrosis and any MPN-related disorder, can be incorporated into any of the embodiments and regimens disclosed herein and are expressly intended to be considered within the scope of the present disclosure.

JAKAFI®—FDA Label Summary

The recommended starting dose of JAKAFI® for myelofibrosis is based on platelet count (Table 3). Before starting therapy, a complete blood count (CBC) and platelet count must be performed, and every 2 to 4 weeks until doses are stabilized, and then as clinically indicated. Doses may be titrated based on safety and efficacy.

TABLE 3 J

AKAFI ® Starting Doses for Myelofibrosis

| Platelet Count | Starting Dose |
| --- | --- |
| Greater than 200 × 10$^9$/L | 20 mg orally twice daily |
| 100 × 10$^9$/L to 200 × 10$^9$/L | 15 mg orally twice daily |
| 50 × 10$^9$/L to less than 100 × 10$^9$/L | 5 mg orally twice daily |

TABLE 4

Myelofibrosis: Maximum Restarting Doses for JAKAFI ® after Safety Interruption for Thrombocytopenia for Patients Starting Treatment with a Platelet Count of 100 × 10$^9$/L or Greater

| Current Platelet Count | Maximum Dose When Restarting JAKAFI ® Treatment[a] |
| --- | --- |
| Greater than or equal to 125 × 10$^9$/L | 20 mg twice daily |
| 100 to less than 125 × 10$^9$/L | 15 mg twice daily |
| 75 to less than 100 × 10$^9$/L | 10 mg twice daily for at least 2 weeks; if stable, may increase to 15 mg twice daily |
| 50 to less than 75 × 10$^9$/L | 5 mg twice daily for at least 2 weeks; if stable, may increase to 10 mg twice daily |
| Less than 50 × 10$^9$/L | Continue hold |

[a]Maximum doses are displayed. When restarting, begin with a dose at least 5 mg twice daily below the dose at interruption.

Following treatment interruption for ANC below 0.5×10$^9$/L, after ANC recovers to 0.75×10$^9$/L or greater, dosing can be restarted at the higher of 5 mg once daily or 5 mg twice daily below the largest dose in the week prior to the treatment interruption.

Dose reductions should be considered if the platelet counts decrease as outlined in Table 5 with the goal of avoiding dose interruptions for thrombocytopenia.

TABLE 5

Myelofibrosis: Dosing Recommendations for Thrombocytopenia for Patients Starting Treatment with a Platelet Count of 100 × 10$^9$/L or Greater

| | Dose at Time of Platelet Decline | | | | |
| --- | --- | --- | --- | --- | --- |
| Platelet Count | 25 mg twice daily New Dose | 20 mg twice daily New Dose | 15 mg twice daily New Dose | 10 mg twice daily New Dose | 5 mg twice daily New Dose |
| 100 to less than 125 × 10$^9$/L | 20 mg twice daily | 15 mg twice daily | no change | no change | no change |
| 75 to less than 100 × 10$^9$/L | 10 mg twice daily | 10 mg twice daily | 10 mg twice daily | no change | no change |
| 50 to less than 75 × 10$^9$/L | 5 mg twice daily | 5 mg twice daily | 5 mg twice daily | 5 mg twice daily | no change |
| Less than 50 × 10$^9$/L | hold | hold | hold | hold | hold |

Dose Modification Guidelines for Hematologic Toxicity for Patients with Myelofibrosis Starting Treatment with a Platelet Count of 100×10$^9$/L or Greater Treatment Interruption and Restarting Dosing Treatment should be interrupted for platelet counts less than 50×10$^9$/L or absolute neutrophil count (ANC) less than 0.5×10$^9$/L. Once platelet counts have recovered to above 50×10$^9$/L and ANC above 0.75×10$^9$/L, dosing may be restarted. Table 4 illustrates the maximum allowable dose that may be used in restarting JAKAFI® after a previous interruption.

Dose Modification Based on Insufficient Response for Patients with Myelofibrosis Starting Treatment with a Platelet Count of 100×10$^9$/L or Greater If the response is insufficient and platelet and neutrophil counts are adequate, doses may be increased in 5 mg twice daily increments to a maximum of 25 mg twice daily. Doses should not be increased during the first 4 weeks of therapy and not more frequently than every 2 weeks. Consider dose increases in patients who meet all of the following conditions: a. Failure to achieve a reduction from pretreatment baseline in either palpable spleen length of 50% or a 35% reduction in spleen volume as measured by computed tomography (CT) or magnetic resonance imaging (MRI); b. Platelet count greater than $125\times10^9$/L at 4 weeks and platelet count never below $100\times10^9$/L; c. ANC Levels greater than $0.75\times10^9$/L. Based on limited clinical data, long-term maintenance at a 5 mg twice daily dose has not shown responses and continued use at this dose should be limited to patients in whom the benefits outweigh the potential risks. Discontinue JAKAFI® if there is no spleen size reduction or symptom improvement after 6 months of therapy.

Treatment Interruption and Restarting Dosing

Treatment should be interrupted for platelet counts less than $25\times10^9$/L or ANC less than $0.5\times10^9$/L. After recovery of platelet counts above $35\times10^9$/L and ANC above $0.75\times10^9$/L, dosing may be restarted. Restart dosing at the higher of 5 mg once daily or 5 mg twice daily below the largest dose in the week prior to the decrease in platelet count below $25\times10^9$/L or ANC below $0.5\times10^9$/L that led to dose interruption.

Dose Reductions

Reduce the dose of JAKAFI® for platelet counts less than $35\times10^9$/L as described in Table 6.

TABLE 6

Myelofibrosis: Dosing Modifications for Thrombocytopenia for Patients with Starting Platelet Count of $50 \times 10^9$/L to Less Than $100 \times 10^9$/L

| Platelet Count | Dosing Recommendations |
|---|---|
| Less than $25 \times 10^9$/L | Interrupt dosing. |
| $25 \times 10^9$/L to less than $35 \times 10^9$/L and the platelet count decline is less than 20% during the prior four weeks | Decrease dose by 5 mg once daily. For patients on 5 mg once daily, maintain dose at 5 mg once daily. |
| $25 \times 10^9$/L to less than $35 \times 10^9$/L AND the platelet count decline is 20% or greater during the prior four weeks | Decrease dose by 5 mg twice daily. For patients on 5 mg twice daily, decrease the dose to 5 mg once daily. For patients on 5 mg once daily, maintain dose at 5 mg once daily. |

Dose Modifications Based on Insufficient Response for Patients with Myelofibrosis and Starting Platelet Count of $50\times10^9$/L to Less Than $100\times10^9$/L Doses should not be increased during the first 4 weeks of therapy, or more frequently than every 2 weeks. If the response is insufficient (see Dose Modification Based on Insufficient Response with Myelofibrosis Starting Treatment with a platelet count of $100\times10^9$/L or Greater), doses may be increased by increments of 5 mg daily to a maximum of 10 mg twice daily if: a) the platelet count has remained at least $40\times10^9$/L, and b) the platelet count has not fallen by more than 20% in the prior 4 weeks, and c) the ANC is more than $1\times10^9$/L, and d) the dose has not been reduced or interrupted for an adverse event or hematological toxicity in the prior 4 weeks. Continuation of treatment for more than 6 months should be limited to patients in whom the benefits outweigh the potential risks. JAKAFI® should be discontinued if there is no spleen size reduction or symptom improvement after 6 months of therapy.

Dose Modification for Bleeding

Interrupt treatment for bleeding requiring intervention regardless of current platelet count. Once the bleeding event has resolved, consider resuming treatment at the prior dose if the underlying cause of bleeding has been controlled. If the bleeding event has resolved but the underlying cause persists, consider resuming treatment with JAKAFI® at a lower dose.

Polycythemia Vera (PCV)

The recommended starting dose of JAKAFI® for polycythemia vera, an MPN-related disorder, is 10 mg twice daily. Doses may be titrated based on safety and efficacy. Dose Modification Guidelines for Patients with Polycythemia Vera A complete blood count (CBC) and platelet count must be performed before initiating therapy, every 2 to 4 weeks until doses are stabilized, and then as clinically indicated.

Dose Reductions

Dose reductions should be considered for hemoglobin and platelet count decreases as described in Table 7.

TABLE 7

Polycythemia Vera: Dose Reductions

| Hemoglobin and/or Platelet Count | Dosing Recommendations |
|---|---|
| Hemoglobin greater than or equal to 12 g/dL AND platelet count greater than or equal to $100 \times 10^9$/L | No change required |
| Hemoglobin 10 to less than 12 g/dL AND platelet count 75 to less than $100 \times 10^9$/L | Dose reductions should be considered with the goal of avoiding dose interruptions for anemia and thrombocytopenia |
| Hemoglobin 8 to less than 10 g/dL OR platelet count 50 to less than $75 \times 10^9$/L | Reduce dose by 5 mg twice daily For patients on 5 mg twice daily, decrease the dose to 5 mg once daily |
| Hemoglobin less than 8 g/dL OR platelet count less than $50 \times 10^9$/L | Interrupt dosing |

Treatment Interruption and Restarting Dosing

Treatment should be interrupted for hemoglobin less than 8 g/dL, platelet counts less than $50\times10^9$/L or ANC less than $1.0\times10^9$/L. After recovery of the hematologic parameter(s) to acceptable levels, dosing may be restarted. Table 8 illustrates the dose that may be used in restarting JAKAFI® after a previous interruption. Use the most severe category of a patient's hemoglobin, platelet count, or ANC abnormality to determine the corresponding maximum restarting dose.

TABLE 8

Polycythemia Vera: Restarting Doses for JAKAFI® after Safety Interruption for Hematologic Parameter(s)

| Hemoglobin, Platelet Count, or ANC | Maximum Restarting Dose |
|---|---|
| Hemoglobin less than 8 g/dL OR platelet count less than $50 \times 10^9$/L OR ANC less than $1 \times 10^9$/L | Continue hold |
| Hemoglobin 8 to less than 10 g/dL OR platelet count 50 to less than $75 \times 10^9$/L OR ANC 1 to less than $1.5 \times 10^9$/L | 5 mg twice daily$^a$ or no more than 5 mg twice daily less than the dose which resulted in dose interruption |

TABLE 8-continued

Polycythemia Vera: Restarting Doses for JAKAFI ® after Safety Interruption for Hematologic Parameter(s)

| Hemoglobin, Platelet Count, or ANC | Maximum Restarting Dose |
|---|---|
| Hemoglobin 10 to less than 12 g/dL OR platelet count 75 to less than 100 × 10⁹/L OR ANC 1.5 to less than 2 × 10⁹/L | 10 mg twice daily$^a$ or no more than 5 mg twice daily less than the dose which resulted in dose interruption |
| Hemoglobin greater than or equal to 12 g/dL OR platelet count greater than or equal to 100 × 10⁹/L OR ANC greater than or equal to 2 × 10⁹/L | 15 mg twice daily$^a$ or no more than 5 mg twice daily less than the dose which resulted in dose interruption |

$^a$Continue treatment for at least 2 weeks; if stable, may increase dose by 5 mg twice daily.

Patients who had required dose interruption while receiving a dose of 5 mg twice daily, may restart at a dose of 5 mg twice daily or 5 mg once daily, but not higher, once hemoglobin is greater than or equal to 10 g/dL, platelet count is greater than or equal to 75×10⁹/L, and ANC is greater than or equal to 1.5×10⁹/L.

Dose Management after Restarting Treatment

After restarting JAKAFI® following treatment interruption, doses may be titrated, but the maximum total daily dose should not exceed 5 mg less than the dose that resulted in the dose interruption. An exception to this is dose interruption following phlebotomy-associated anemia, in which case the maximal total daily dose allowed after restarting JAKAFI® would not be limited.

Dose Modifications Based on Insufficient Response for Patients with Polycythemia Vera If the response is insufficient and platelet, hemoglobin, and neutrophil counts are adequate, doses may be increased in 5 mg twice daily increments to a maximum of 25 mg twice daily. Doses should not be increased during the first 4 weeks of therapy and not more frequently than every two weeks.

Consider dose increases in patients who meet all of the following conditions:

1. Inadequate efficacy as demonstrated by one or more of the following:
   a. Continued need for phlebotomy
   b. WBC greater than the upper limit of normal range
   c. Platelet count greater than the upper limit of normal range
   d. Palpable spleen that is reduced by less than 25% from Baseline
2. Platelet count greater than or equal to 140×10⁹/L
3. Hemoglobin greater than or equal to 12 g/dL
4. ANC greater than or equal to 1.5×10⁹/L Dose Modifications for Concomitant Use with Strong CYP3A4 Inhibitors or Fluconazole JAKAFI® dosage can be modified when co-administered with strong CYP3A4 inhibitors and fluconazole doses of less than or equal to 200 mg according to Table 10. Additional dose modifications should be made with frequent monitoring of safety and efficacy. The use of fluconazole doses of greater than 200 mg daily with JAKAFI® should be avoided.

TABLE 10

Dose Modifications for Concomitant Use with Strong CYP3A4 Inhibitors or Fluconazole

| For patients co-administered strong CYP3A4 inhibitors or fluconazole doses of less than or equal to 200 mg | Recommended Dose Modification |
|---|---|
| Starting dose for patients with MF with a platelet count: | |
| Greater than or equal to 100 × 10⁹/L | 10 mg twice daily |
| 50 × 10⁹/L to less than 100 × 10⁹/L | 5 mg once daily |
| Starting dose for patients with PV: | 5 mg once daily |
| If on stable dose for patients with MF or PV: | |
| Greater than or equal to 10 mg twice daily | Decrease dose by 50% (round up to the closest available tablet strength) |
| 5 mg twice daily | 5 mg once daily |
| 5 mg once daily | Avoid strong CYP3A4 inhibitor or fluconazole treatment or interrupt JAKAFI® treatment for the duration of strong CYP3A4 inhibitor or fluconazole use |

$^a$With coadministration of itraconazole, monitor blood counts more frequently for toxicity and adjust the dose of JAKAFI® if necessary.

Dose Modifications for Renal or Hepatic Impairment Renal Impairment

Patients with Moderate or Severe Renal Impairment

JAKAFI® dosage for patients with moderate or severe renal impairment can be modified according to Table 11. Patients with End Stage Renal Disease on Dialysis Modify the JAKAFI® dosage for patients with end stage renal disease (ESRD) on dialysis according to Table 12. Make additional dose modifications with frequent monitoring of safety and efficacy. Use of JAKAFI® in patients with ESRD (CLcr less than 15 mL/min) not requiring dialysis should be avoided.

TABLE 11

Dose Modifications for Renal Impairment

| Renal Impairment Status | Platelet Count | Recommended Starting Dosage |
|---|---|---|
| Patients with MF | | |
| Moderate (CLcr 30 to 59 mL/min) or Severe (CLcr 15 to 29 mL/min) | Greater than 150 × 10⁹/L | No dose modification needed |
| | 100 to 150 × 10⁹/L | 10 mg twice daily |

TABLE 11-continued

Dose Modifications for Renal Impairment

| Renal Impairment Status | Platelet Count | Recommended Starting Dosage |
|---|---|---|
| | 50 to less than 100 × 10$^9$/L | 5 mg daily |
| | Less than 50 × 10$^9$/L | Avoid use |
| ESRD (CLcr less than 15 mL/min) on dialysis | 100 to 200 × 10$^9$/L | 15 mg once after dialysis session |
| | Greater than 200 × 10$^9$/L | 20 mg once after dialysis session |
| Patients with PV | | |
| Moderate (CLcr 30 to 59 mL/min) or Severe (CLcr 15 to 29 mL/min) | Any | 5 mg twice daily |
| ESRD (CLcr less than 15 mL/min) on dialysis | Any | 10 mg once after dialysis session |

ESRD = end stage renal disease, and CLcr = creatinine clearance

Hepatic Impairment

JAKAFI® dosage can be modified for patients with hepatic impairment according to Table 12.

TABLE 12

Dose Modifications for Hepatic Impairment

| Hepatic Impairment Status | Platelet Count | Platelet Count |
|---|---|---|
| Patients with MF Mild, Moderate, or Severe (ChildPugh Class A, B, C) | Greater than 150 × 10$^9$/L | No dose modification needed |
| | 100 × 10$^9$/L to 150 × 10$^9$/L | 10 mg twice daily |
| | 50 to less than 100 × 10$^9$/L | 5 mg daily |
| | Less than 50 × 10$^9$/L | Avoid use |
| Patients with PV Mild, Moderate, or Severe (ChildPugh Class A, B, C) | Any | 5 mg twice daily |

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the treatment of the human subject optionally results in a spleen volume reduction of at least 35%. In one aspect, the therapeutically effective amount of ruxolitinib is at least 10 mg. In another aspect, the therapeutically effective amount of ruxolitinib is 10 mg. It is to be understood that various combinations of a therapeutically effective amount of navitoclax in combination with a therapeutically effective amount of ruxolitinib are contemplated. In some embodiments, the MPN-related disorder comprises polycythemia vera (PCV), essential thrombocytopenia (ET), or chronic myelomonocytic leukemia (CMML).

For example, in the method for treatment of a human subject with myelofibrosis or a myeloproliferative neoplasm (MPN)-related disorder comprising administering a therapeutically effective amount of navitoclax; in combination with administering a therapeutically effective amount of ruxolitinib; wherein treatment of the human subject optionally results in a spleen volume reduction of at least 35%, the therapeutically effective amount of navitoclax may be 50 mg and the therapeutically effective amount of ruxolitinib may be 10 mg; or the therapeutically effective amount of navitoclax may be 100 mg and the therapeutically effective amount of ruxolitinib may be 10 mg; or the therapeutically effective amount of navitoclax may be 200 mg and the therapeutically effective amount of ruxolitinib may be 10 mg; or the therapeutically effective amount of navitoclax may be 300 mg and the therapeutically effective amount of ruxolitinib may be 10 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the treatment of the human subject optionally results in a spleen volume reduction of at least 35%; wherein the therapeutically effective amount of navitoclax is administered once a day; and wherein the therapeutically effective amount of ruxolitinib is administered twice a day. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the treatment of the human subject optionally results in a spleen volume reduction of at least 35% by week 24. In one aspect, the spleen volume reduction may be measure by MRI. In one aspect, the therapeutically effective amount of ruxolitinib is at least 10 mg. In another aspect, the therapeutically effective amount of ruxolitinib is 10 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the treatment of the human subject optionally results in a spleen volume reduction of at least 35% by week 24; wherein the therapeutically effective amount of navitoclax is administered once a day; and wherein the therapeutically effective amount of ruxolitinib is administered twice a day. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the treatment of the human subject optionally results in a spleen volume reduction of at least 35%; wherein the therapeutically effective amount of navitoclax is administered once a day; wherein the therapeutically effective amount of ruxolitinib is administered twice a day; and wherein the human subject has been treated with a JAK-2 inhibitor prior to administering the therapeutically effective amount of navitoclax. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In yet another aspect, the therapeutically effective amount of navitoclax is 200 mg and the therapeutically effective amount of ruxolitinib is 10 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the treatment of the human subject optionally results in a spleen volume reduction of at least 35%; wherein the therapeutically effective amount of navitoclax is administered once a day; wherein the therapeutically effective amount of ruxolitinib is administered twice a day; wherein the human subject has been treated with a JAK2 inhibitor prior to administering the therapeutically effective amount of navitoclax; and wherein the JAK2 inhibitor is ruxolitinib. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK2 inhibitor is provided, comprising orally administering to the human subject with myelofibrosis or a myeloproliferative neoplasm (MPN)-related disorder once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with orally administering to the human subject with myelofibrosis or a myeloproliferative neoplasm (MPN)-related disorder twice a day a therapeutically effective amount of ruxolitinib of 10 mg twice a day; wherein following 24 weeks of said administering navitoclax in combination with ruxolitinib, the spleen volume of the human subject with myelofibrosis or a myeloproliferative neoplasm (MPN)-related disorder is optionally reduced by at least 35%. In one aspect, the therapeutically effective amount of ruxolitinib is selected from the group consisting of 5 mg, 10 mg, 15 mg, 20 mg, 25 mg, 30 mg, 40 mg and 50 mg. In another aspect, the therapeutically effective amount of ruxolitinib is selected from the group consisting of 10 mg, 15 mg, 20 mg, 25 mg, 30 mg, 40 mg and 50 mg. In another aspect, the therapeutically effective amount of ruxolitinib is 5 mg. In one aspect, the therapeutically effective amount of ruxolitinib is at least 10 mg. In another aspect, the therapeutically effective amount of ruxolitinib is 10 mg. In another aspect, the therapeutically effective amount of ruxolitinib is 5 mg. In yet another aspect, the therapeutically effective amount of ruxolitinib is 15 mg. In yet another aspect, the therapeutically effective amount of ruxolitinib is 20 mg. In another aspect, the therapeutically effective amount of ruxolitinib is 25 mg. In still another aspect, the therapeutically effective amount of ruxolitinib is 30 mg. In another aspect, the therapeutically effective amount of ruxolitinib is 40 mg. In yet another aspect, the therapeutically effective amount of ruxolitinib is 50 mg. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK2 inhibitor is provided, comprising orally administering to the human subject with myelofibrosis or a myeloproliferative neoplasm (MPN)-related disorder once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with orally administering to the human subject with myelofibrosis or a myeloproliferative neoplasm (MPN)-related disorder twice a day a therapeutically effective amount of ruxolitinib of 10 mg twice a day; wherein following 24 weeks of said administering navitoclax in combination with ruxolitinib, the spleen volume of the human subject with myelofibrosis or a myeloproliferative neoplasm (MPN)-related disorder is optionally reduced by at least 35%. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder once a day a therapeutically effective amount of navitoclax of 50 mg; in combination with orally administering to the human subject with myelofibrosis or a myeloproliferative neoplasm (MPN)-related disorder twice a day a therapeutically effective amount of ruxolitinib of 10 mg twice a day; wherein after at least 7 days, the therapeutically effective amount of navitoclax is increased from 50 mg to 100 mg; wherein following 24 weeks of said administering navitoclax in combination with ruxolitinib, the spleen volume of the human subject with myelofibrosis or a myeloproliferative neoplasm (MPN)-related disorder is optionally reduced by at least 35%. In one aspect, the human subject has a platelet count of at least 75×10$^9$/L prior to increasing the therapeutically effective amount of navitoclax. In another aspect, after at least 7 days at 100 mg of navitoclax, the therapeutically effective amount of navitoclax is increased from 100 mg to 200 mg. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder once a day a therapeutically effective amount of navitoclax is 100 mg; in combination with orally administering to the human subject with myelofibrosis or a myeloproliferative neoplasm (MPN)-related disorder twice a day a therapeutically effective amount of ruxolitinib of 10 mg twice a day; wherein after at least 7 days, the therapeutically effective amount of navitoclax is increased to 200 mg; wherein following 24 weeks of said administering navitoclax in combination with ruxolitinib, the spleen volume of the human subject with myelofibrosis or a myeloproliferative neoplasm (MPN)-related disorder is optionally reduced by at least 35%. In one aspect, the human subject has a platelet count of at least 75×10$^9$/L prior to increasing the therapeutically effective amount of navitoclax. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder once a day a therapeutically effective amount of navitoclax is 200 mg; in combination with orally administering to the human subject with myelofibrosis or a myeloproliferative neoplasm (MPN)-related disorder twice a day a therapeutically effective amount of ruxolitinib of 10 mg twice a day; wherein the human subject has a platelet count of at least 150×10$^9$/L prior to administering navitoclax a first time; wherein following 24 weeks of said administering navitoclax in combination with ruxolitinib, the spleen volume of the human subject with myelofibrosis is optionally reduced by at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; and wherein the treatment of the human subject optionally results in a spleen volume reduction of at least 35%. In one aspect, the therapeutically effective amount of ruxolitinib is at least 10 mg. In another aspect, the therapeutically effective amount of ruxolitinib is selected from the group consisting of 5 mg, 10 mg, 15 mg, 20 mg, 25 mg, 30 mg, 40 mg and 50 mg. In yet another aspect, the therapeutically effective amount of ruxolitinib is selected from the group consisting of 10 mg, 15 mg, 20 mg, 25 mg, 30 mg, 40 mg and 50 mg. In one aspect, the therapeutically effective amount of ruxolitinib is 10 mg. In another aspect, the therapeutically effective amount of ruxolitinib is 5 mg. In another aspect, the therapeutically effective amount of ruxolitinib is 15 mg. In yet another aspect, the therapeutically effective amount of ruxolitinib is 20 mg. In another aspect, the therapeutically effective amount of ruxolitinib is 25 mg. In still another aspect, the therapeutically effective amount of ruxolitinib is 30 mg. In another aspect, the therapeutically effective amount of ruxolitinib is 40 mg. In yet another aspect, the therapeutically effective amount of ruxolitinib is 50 mg. It is to be understood that various combinations of a therapeutically effective amount of navitoclax in combination with a therapeutically effective amount of ruxolitinib are contemplated.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the myelofibrosis is relapsed or refractory myelofibrosis; wherein the treatment of the human subject optionally results in a spleen volume reduction of at least 35%; wherein the therapeutically effective amount of navitoclax is administered once a day; and wherein the therapeutically effective amount of ruxolitinib is administered twice a day. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In still another aspect, the therapeutically effective amount of navitoclax is 200 mg and the therapeutically effective amount of ruxolitinib is 10 mg.

In one embodiment, a method for treatment of a human subject with myelofibrosis is provided, comprising administering a therapeutically effective amount of navitoclax selected from the group consisting 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; wherein the human subject has received at least one dose of ruxolitinib prior to administering a therapeutically effective amount of navitoclax; and wherein the treatment of the human subject optionally results in a spleen volume reduction of at least 35%. In one aspect, the human subject has received at least one dose at least 10 mg of ruxolitinib prior to administering a therapeutically effective amount of navitoclax. In another aspect, the human subject has received at least one dose of 10 mg of ruxolitinib prior to administering a therapeutically effective amount of navitoclax.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 200 mg, 225 mg, 250 mg, 275 mg, and 300 mg in combination with administering a therapeutically effective amount of ruxolitinib; wherein the human subject has received at least one dose of ruxolitinib prior to administering the therapeutically effective amount of navitoclax; and wherein the treatment of the human subject optionally results in a spleen volume reduction of at least 35%. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In another embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the human subject has received at least one dose of ruxolitinib of at least 10 mg prior to administering the therapeutically effective amount of navitoclax; and wherein the treatment of the human subject optionally results in a spleen volume reduction of at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the human subject has received at least one dose of ruxolitinib prior to administering the therapeutically effective amount of navitoclax; wherein the dose of ruxolitinib is more than 10 mg, wherein the dose of ruxolitinib is reduced to the therapeutically effective amount of ruxolitinib of 10 mg prior to administering the therapeutically effective amount of navitoclax; and wherein the treatment of the human subject optionally results in a spleen volume reduction of at least 35%. In one aspect, the therapeutically effective amount of ruxolitinib of 10 mg is administered twice a day. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the human subject has received at least one dose of ruxolitinib prior to administering the therapeutically effective amount of navitoclax; wherein the dose of ruxolitinib is more than 10 mg, wherein the dose of ruxolitinib is reduced to the therapeutically effective amount of ruxolitinib of 10 mg after administering the therapeutically effective amount of navitoclax; and wherein the treatment of the human subject optionally results in a spleen volume reduction of at least 35%. In one aspect, the therapeutically effective amount of ruxolitinib of 10 mg is administered twice a day. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the myelofibrosis is relapsed or refractory myelofibrosis; wherein the human subject has received a dose of at least 10 mg ruxolitinib twice a day for 12 weeks prior to administering a therapeutically effective amount of navitoclax; and wherein the treatment of the human subject optionally results in a spleen volume reduction of at least 35%. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In yet another aspect, the therapeutically effective amount of navitoclax is 200 mg and the therapeutically effective amount of ruxolitinib is 10 mg.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the human subject has failed to achieve a spleen volume reduction of at least 35% prior to being administered navitoclax; and wherein the treatment of the human subject optionally results in a spleen volume reduction of at least 35%. In one aspect, the therapeutically effective amount of ruxolitinib is at least 10 mg. In another aspect, the therapeutically effective amount of ruxolitinib is selected from the group consisting of 5 mg, 10 mg, 15 mg, 20 mg, 25 mg, 30 mg, 40 mg and 50 mg. In yet another aspect, the therapeutically effective amount of ruxolitinib is selected from the group consisting of 10 mg, 15 mg, 20 mg, 25 mg, 30 mg, 40 mg and 50 mg. In one aspect, the therapeutically effective amount of ruxolitinib is 10 mg. In another aspect, the therapeutically effective amount of ruxolitinib is 5 mg. In another aspect, the therapeutically effective amount of ruxolitinib is 15 mg. In yet another aspect, the therapeutically effective amount of ruxolitinib is 20 mg. In another aspect, the therapeutically effective amount of ruxolitinib is 25 mg. In still another aspect, the therapeutically effective amount of ruxolitinib is 30 mg. In another aspect, the therapeutically effective amount of ruxolitinib is 40 mg. In yet another aspect, the therapeutically effective amount of ruxolitinib is 50 mg. It is to be understood that various combinations of a therapeutically effective amount of navitoclax in combination with a therapeutically effective amount of ruxolitinib are contemplated. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the human subject has failed to achieve a spleen volume reduction of at least 35% prior to being administered navitoclax; wherein the treatment of the human subject optionally results in a spleen volume reduction of at least 35%; wherein the therapeutically effective amount of navitoclax is administered once a day; and wherein the therapeutically effective amount of ruxolitinib is administered twice a day. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In still another aspect, the therapeutically effective amount of navitoclax is 200 mg and the therapeutically effective amount of ruxolitinib is 10 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the human subject has failed to achieve a spleen volume reduction of at least 35% prior to being administered navitoclax; wherein the human subject has received at least one dose of ruxolitinib prior to administering a therapeutically effective amount of navitoclax; and wherein the treatment of the human subject optionally results in a spleen volume reduction of at least 35%. In one aspect, the human subject has received at least one dose at least 10 mg of ruxolitinib prior to administering a therapeutically effective amount of navitoclax. In another aspect, the human subject has received at least one dose of 10 mg of ruxolitinib prior to administering a therapeutically effective amount of navitoclax. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the human subject has failed to achieve a spleen volume reduction of at least 35% prior to being administered navitoclax; wherein the human subject has received a dose of at least 10 mg ruxolitinib twice a day for 12 weeks prior to administering a therapeutically effective amount of navitoclax; and wherein the treatment of the human subject optionally results in a spleen volume reduction of at least 35%. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In yet another aspect, the therapeutically effective amount of navitoclax is 200 mg and the therapeutically effective amount of ruxolitinib is 10 mg. In some embodiments, the MPN-related disorder comprises polycythemia vera (PCV), essential thrombocytopenia (ET), or chronic myelomonocytic leukemia (CMML).

In one embodiment, a method for improving bone marrow fibrosis grade in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder who once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with orally administering to the human subject with myelofibrosis or a myeloproliferative neoplasm (MPN)-related disorder who twice a day a therapeutically effective amount of ruxolitinib; wherein following 24 weeks of said administering navitoclax in combination with ruxolitinib the bone marrow fibrosis grade of the human subject with myelofibrosis or a myeloproliferative neoplasm (MPN)-related disorder who is improved by at least one grade. In one aspect, the grade of the bone marrow fibrosis is measured according to the European Consensus grading system. In one aspect, the bone marrow fibrosis grade is improved to MF-2. In one aspect, the bone marrow fibrosis grade is improved to MF-1. In one aspect, the bone marrow fibrosis grade is improved to MF-0. In one aspect, the baseline grade of bone marrow fibrosis is ≥1. In some embodiments, the MPN-related disorder comprises polycythemia vera (PCV), essential thrombocytopenia (ET), or chronic myelomonocytic leukemia (CMML).

In one embodiment, a method for improving bone marrow fibrosis grade in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder who once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with orally administering to the human subject with myelofibrosis or a myeloproliferative neoplasm (MPN)-related disorder who twice a day a therapeutically effective amount of ruxolitinib of at least 10 mg; wherein following 24 weeks of said administering navitoclax in combination with ruxolitinib the bone marrow fibrosis grade of the human subject with myelofibrosis or a myeloproliferative neoplasm (MPN)-related disorder who is improved by at least one grade. In one aspect, the therapeutically effective amount of navitoclax is 100 mg. In one aspect, the therapeutically effective amount of navitoclax is 200 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; and wherein the treatment of the human subject results in an improvement in a grade of bone marrow fibrosis relative to a baseline grade of bone marrow fibrosis.

In one embodiment, a method for treatment of a human subject with is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; wherein the treatment of the human subject results in an improvement in a grade of bone marrow fibrosis relative to a baseline grade of bone marrow fibrosis; and wherein the improvement in the grade of the bone marrow fibrosis is measured according to the European consensus grading system.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; and wherein the treatment of the human subject results in an improvement in a grade of bone marrow fibrosis relative to a baseline grade of bone marrow fibrosis of ≥1. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In yet another aspect, the therapeutically effective amount of navitoclax is 200 mg and the therapeutically effective amount of ruxolitinib is 10 mg.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; wherein the treatment of the human subject results in an improvement in a grade of bone marrow fibrosis relative to a baseline grade of bone marrow fibrosis of ≥1; wherein the therapeutically effective amount of navitoclax is administered once a day; and wherein the therapeutically effective amount of ruxolitinib is administered twice a day. In one aspect, the therapeutically effective amount of navitoclax is 100 mg. In another aspect, the therapeutically effective amount of navitoclax is 100 mg and the therapeutically effective amount of ruxolitinib is 10 mg. In yet another aspect, the therapeutically effective amount of navitoclax is 200 mg. In yet another aspect, the therapeutically effective amount of navitoclax is 200 mg and the therapeutically effective amount of ruxolitinib is 10 mg.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein an initial dose of therapeutically effective amount of navitoclax is 50 mg; and wherein the treatment of the human subject results in a spleen volume reduction of at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein an initial dose of therapeutically effective amount of navitoclax is 50 mg; wherein after at least 7 days the therapeutically effective amount of navitoclax is increased to a next higher dose of the therapeutically effective amount of navitoclax; and wherein the treatment of the human subject results in a spleen volume reduction of at least 35%. In one aspect, a maximum dose of navitoclax is 200 mg. In one aspect, a maximum dose of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of ruxolitinib to the human subject, the improvement comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with said ruxolitinib, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 10 mg of ruxolitinib to the human subject, the improvement comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with said ruxolitinib, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 20 mg of ruxolitinib to the human subject, the improvement comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with said ruxolitinib, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 10 mg of ruxolitinib to the human subject twice daily, the improvement comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with said ruxolitinib, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 20 mg of ruxolitinib to the human subject twice daily, the improvement comprising administering a therapeutically effective amount of navitoclax selected from the group consisting of 50 mg, 100 mg, 200 mg, and 300 mg; in combination with said ruxolitinib, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering a therapeutically effective amount of ruxolitinib to the human subject, the improvement comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with said ruxolitinib, wherein the treatment of the human subject results in a spleen volume reduction of at least 35%, wherein the MPN-related disorder is selected from the group consisting of polycythemia vera (PCV), essential thrombocytopenia (ET), and chronic monomyelocytic leukemia (CMML), wherein the therapeutically effective amount of navitoclax is administered once a day; and wherein the therapeutically effective amount of ruxolitinib is administered twice a day.

In one embodiment, a method for treatment of a human subject with myelofibrosis or a myeloproliferative neoplasm (MPN)-related disorder is provided, comprising administering a therapeutically effective amount of ruxolitinib to the human subject, the improvement comprising administering 100 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering a therapeutically effective amount of ruxolitinib to the human subject, the improvement comprising administering 200 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering a therapeutically effective amount of ruxolitinib to the human subject, the improvement comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with said ruxolitinib, wherein the treatment of the human subject results in a spleen volume reduction of at least 35%, wherein the MPN-related disorder is selected from the group consisting of polycythemia vera (PCV), essential thrombocytopenia (ET), and chronic monomyelocytic leukemia (CMML), wherein the human subject has been treated with a JAK-2 inhibitor prior to administering the therapeutically effective amount of navitoclax.

In one embodiment, a method for treatment of a human subject with myelofibrosis or a myeloproliferative neoplasm (MPN)-related disorder is provided, comprising administering 10 mg of ruxolitinib to the human subject, the improvement comprising administering 100 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 20 mg of ruxolitinib to the human subject, the improvement comprising administering 100 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 10 mg of ruxolitinib to the human subject, the improvement comprising administering 100 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 20 mg of ruxolitinib to the human subject, the improvement comprising administering 100 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 10 mg of ruxolitinib to the human subject, the improvement comprising administering 200 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering 20 mg of ruxolitinib to the human subject, the improvement comprising administering 200 mg of navitoclax to the human subject, wherein the treatment of the human subject results in a spleen volume reduction of at least 35%, and wherein the MPN-related disorder is selected from the group consisting of polycythemia vera (PCV), essential thrombocytopenia (ET), and chronic monomyelocytic leukemia (CMML).

In one embodiment, a method for treatment of a human subject with myelofibrosis or a myeloproliferative neoplasm (MPN)-related disorder is provided, comprising administering a therapeutically effective amount of ruxolitinib to the human subject, the improvement comprising administering a therapeutically effective amount of navitoclax selected from the group consisting of 50 mg, 100 mg, 200 mg, and 300 mg; in combination with said ruxolitinib, wherein the treatment of the human subject results in a spleen volume reduction of at least 35%, wherein the MPN-related disorder is selected from the group consisting of polycythemia vera (PCV), essential thrombocytopenia (ET), and chronic monomyelocytic leukemia (CMML), wherein the treatment of the human subject results in a spleen volume reduction of at least 35% by week 24.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the treatment of the human subject optionally results in a spleen volume reduction of at least 35%. In some embodiments, the MPN-related disorder comprises polycythemia vera (PCV), essential thrombocytopenia (ET), or chronic myelomonocytic leukemia (CMML).

For example, in the method for treatment of a human subject with myelofibrosis or a myeloproliferative neoplasm (MPN)-related disorder comprising administering a therapeutically effective amount of navitoclax; wherein treatment of the human subject optionally results in a spleen volume reduction of at least 35%, the therapeutically effective amount of navitoclax may be 50 mg or the therapeutically effective amount of navitoclax may be 100 mg; or the therapeutically effective amount of navitoclax may be 200 mg; or the therapeutically effective amount of navitoclax may be 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; wherein the treatment of the human subject optionally results in a spleen volume reduction of at least 35%; wherein the therapeutically effective amount of navitoclax is administered once a day; In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 50 mg, 100 mg, 200 mg, and 300 mg; wherein the treatment of the human subject optionally results in a spleen volume reduction of at least 35% by week 24. In one aspect, the spleen volume reduction may be measure by MRI. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the treatment of the human subject optionally results in a spleen volume reduction of at least 35% by week 24; wherein the therapeutically effective amount of navitoclax is administered once a day. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the treatment of the human subject optionally results in a spleen volume reduction of at least 35%; wherein the therapeutically effective amount of navitoclax is administered once a day; and wherein the human subject has been treated with a JAK-2 inhibitor prior to administering the therapeutically effective amount of navitoclax. In one aspect, the therapeutically effective amount of navitoclax is 100 mg. In another aspect, the therapeutically effective amount of navitoclax is 100 mg. In yet another aspect, the therapeutically effective amount of navitoclax is 150 mg. In yet another aspect, the therapeutically effective amount of navitoclax is 200 mg. In yet another aspect, the therapeutically effective amount of navitoclax is 250 mg. In yet another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib of at least 10 mg; wherein the treatment of the human subject optionally results in a spleen volume reduction of at least 35%; wherein the therapeutically effective amount of navitoclax is administered once a day; wherein the therapeutically effective amount of ruxolitinib is administered twice a day; wherein the human subject has been treated with a JAK2 inhibitor prior to administering the therapeutically effective amount of navitoclax; and wherein the JAK2 inhibitor is ruxolitinib. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK2 inhibitor is provided, comprising orally administering to the human subject with myelofibrosis or a myeloproliferative neoplasm (MPN)-related disorder once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein following 24 weeks of said administering navitoclax in combination with ruxolitinib, the spleen volume of the human subject with myelofibrosis or a myeloproliferative neoplasm (MPN)-related disorder is optionally reduced by at least 35%. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK2 inhibitor is provided, comprising orally administering to the human subject with myelofibrosis or a myeloproliferative neoplasm (MPN)-related disorder once a day a therapeutically effective amount of navitoclax selected from the group consisting of 50 mg, 100 mg, 200 mg, and 300 mg; wherein following 24 weeks of said administering navitoclax in combination with ruxolitinib, the spleen volume of the human subject with myelofibrosis or a myeloproliferative neoplasm (MPN)-related disorder is optionally reduced by at least 35%. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder once a day a therapeutically effective amount of navitoclax of 50 mg; wherein after at least 7 days, the therapeutically effective amount of navitoclax is increased from 50 mg to 100 mg; wherein following 24 weeks of said administering navitoclax, the spleen volume of the human subject with myelofibrosis or a myeloproliferative neoplasm (MPN)-related disorder is optionally reduced by at least 35%. In one aspect, the human subject has a platelet count of at least $75 \times 10^9$/L prior to increasing the therapeutically effective amount of navitoclax. In another aspect, after at least 7 days at 100 mg of navitoclax, the therapeutically effective amount of navitoclax is increased from 100 mg to 200 mg. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder once a day a therapeutically effective amount of navitoclax is 100 mg; wherein after at least 7 days, the therapeutically effective amount of navitoclax is increased to 200 mg; wherein following 24 weeks of said administering navitoclax, the spleen volume of the human subject with myelofibrosis or a myeloproliferative neoplasm (MPN)-related disorder is optionally reduced by at least 35%. In one aspect, the human subject has a platelet count of at least $75 \times 10^9$/L prior to increasing the therapeutically effective amount of navitoclax. In some embodiments, the MPN-related disorder comprises polycythemia vera (PCV), essential thrombocytopenia (ET), or chronic myelomonocytic leukemia (CMML).

In one embodiment, a method for significantly reducing spleen volume in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder once a day a therapeutically effective amount of navitoclax is 200 mg; wherein the human subject has a platelet count of at least $150 \times 10^9$/L prior to administering navitoclax a first time; wherein following 24 weeks of said administering navitoclax, the spleen volume of the human subject with myelofibrosis is optionally reduced by at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the myelofibrosis is relapsed or refractory myelofibrosis; and wherein the treatment of the human subject optionally results in a spleen volume reduction of at least 35%.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the treatment of the human subject optionally results in a spleen volume reduction of at least 35%; wherein the therapeutically effective amount of navitoclax is administered once a day. In one aspect, the therapeutically effective amount of navitoclax is 100 mg. In yet another aspect, the therapeutically effective amount of navitoclax is 200 mg.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the myelofibrosis is relapsed or refractory myelofibrosis; wherein the human subject has received at least one dose of ruxolitinib prior to administering a therapeutically effective amount of navitoclax; and wherein the treatment of the human subject optionally results in a spleen volume reduction of at least 35%. In one aspect, the human subject has received at least one dose at least 10 mg of ruxolitinib prior to administering a therapeutically effective amount of navitoclax. In another aspect, the human subject has received at least one dose of 20 mg of ruxolitinib prior to administering a therapeutically effective amount of navitoclax.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has received at least one dose of a JAK2 inhibitor prior to administering the therapeutically effective amount of navitoclax; and wherein the treatment of the human subject optionally results in a spleen volume reduction of at least 35%. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has received at least one dose of ruxolitinib prior to administering the therapeutically effective amount of navitoclax; and wherein the treatment of the human subject optionally results in a spleen volume reduction of at least 35%. In one aspect, the therapeutically effective amount of navitoclax is 50 mg. In another aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In another embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has received at least one dose of ruxolitinib of at least 10 mg prior to administering the therapeutically effective amount of navitoclax; and wherein the treatment of the human subject optionally results in a spleen volume reduction of at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has received at least one dose of ruxolitinib prior to administering the therapeutically effective amount of navitoclax; wherein the dose of ruxolitinib is more than 10 mg, wherein the dose of ruxolitinib is reduced to the therapeutically effective amount of ruxolitinib of 10 mg prior to administering the therapeutically effective amount of navitoclax; and wherein the treatment of the human subject optionally results in a spleen volume reduction of at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has received at least one dose of ruxolitinib prior to administering the therapeutically effective amount of navitoclax; and wherein the treatment of the human subject optionally results in a spleen volume reduction of at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the myelofibrosis is relapsed or refractory myelofibrosis; wherein the human subject has received a dose of at least 10 mg ruxolitinib twice a day for 12 weeks prior to administering a therapeutically effective amount of navitoclax; and wherein the treatment of the human subject optionally results in a spleen volume reduction of at least 35%. In one aspect, the therapeutically effective amount of navitoclax is 100 mg. In yet another aspect, the therapeutically effective amount of navitoclax is 200 mg. In yet another aspect, the therapeutically effective amount of navitoclax is 300 mg.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has failed to achieve a spleen volume reduction of at least 35% prior to being administered navitoclax; and wherein the treatment of the human subject optionally results in a spleen volume reduction of at least 35%. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has failed to achieve a spleen volume reduction of at least 35% prior to being administered navitoclax; wherein the treatment of the human subject optionally results in a spleen volume reduction of at least 35%; wherein the therapeutically effective amount of navitoclax is administered once a day. In one aspect, the therapeutically effective amount of navitoclax is 100 mg. In yet another aspect, the therapeutically effective amount of navitoclax is 200 mg. In still another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has failed to achieve a spleen volume reduction of at least 35% prior to being administered navitoclax; wherein the human subject has received at least one dose of ruxolitinib prior to administering a therapeutically effective amount of navitoclax; and wherein the treatment of the human subject optionally results in a spleen volume reduction of at least 35%. In one aspect, the human subject has received at least one dose at least 10 mg of ruxolitinib prior to administering a therapeutically effective amount of navitoclax. In another aspect, the human subject has received at least one dose of 10 mg of ruxolitinib prior to administering a therapeutically effective amount of navitoclax. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the human subject has failed to achieve a spleen volume reduction of at least 35% prior to being administered navitoclax; wherein the human subject has received a dose of at least 10 mg ruxolitinib twice a day for 12 weeks prior to administering a therapeutically effective amount of navitoclax; and wherein the treatment of the human subject optionally results in a spleen volume reduction of at least 35%. In one aspect, the therapeutically effective amount of navitoclax is 100 mg. In yet another aspect, the therapeutically effective amount of navitoclax is 200 mg. In yet another aspect, the therapeutically effective amount of navitoclax is 300 mg. In some embodiments, the MPN-related disorder comprises polycythemia vera (PCV), essential thrombocytopenia (ET), or chronic myelomonocytic leukemia (CMML).

In one embodiment, a method for improving bone marrow fibrosis grade in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder who once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein following 24 weeks of said administering navitoclax the bone marrow fibrosis grade of the human subject with myelofibrosis or a myeloproliferative neoplasm (MPN)-related disorder who is improved by at least one grade. In one aspect, the grade of the bone marrow fibrosis is measured according to the European Consensus grading system. In one aspect, the bone marrow fibrosis grade is improved to MF-2. In one aspect, the bone marrow fibrosis grade is improved to MF-1. In one aspect, the bone marrow fibrosis grade is improved to MF-0. In one aspect, the baseline grade of bone marrow fibrosis is ≥1. In some embodiments, the MPN-related disorder comprises polycythemia vera (PCV), essential thrombocytopenia (ET), or chronic myelomonocytic leukemia (CMML).

In one embodiment, a method for improving bone marrow fibrosis grade in a human subject with myelofibrosis or a myeloproliferative neoplasm (MPN)-related disorder who is refractory to treatment with a JAK-2 inhibitor is provided, comprising orally administering to the human subject with myelofibrosis or a myeloproliferative neoplasm (MPN)-related disorder who once a day a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein following 24 weeks of said administering navitoclax the bone marrow fibrosis grade of the human subject with myelofibrosis or a myeloproliferative neoplasm (MPN)-related disorder who is improved by at least one grade. In one aspect, the therapeutically effective amount of navitoclax is 100 mg. In one aspect, the therapeutically effective amount of navitoclax is 200 mg. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with primary myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with myelofibrosis or a myeloproliferative neoplasm (MPN)-related disorder is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with relapsed or refractory myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with polycythemia vera (PCV) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with essential thrombocytopenia (ET) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with chronic myelomonocytic leukemia (CMML) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject with relapsed or refractory myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject with polycythemia vera (PCV) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject with essential thrombocytopenia (ET) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject with chronic myelomonocytic leukemia (CMML) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject with myelofibrosis is provided, comprising administering a therapeutically effective amount of navitoclax selected from the group consisting of 5 mg once daily, 10 mg once daily, 15 mg once daily, 20 mg once daily, and 25 mg once daily.

In one embodiment, a method for treatment of a human subject with relapsed or refractory myelofibrosis is provided, comprising administering a therapeutically effective amount of navitoclax selected from the group consisting 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg once daily, 10 mg once daily, 15 mg once daily, 20 mg once daily, and 25 mg once daily.

In one embodiment, a method for treatment of a human subject with polycythemia vera (PCV) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg once daily, 10 mg once daily, 15 mg once daily, 20 mg once daily, and 25 mg once daily.

In one embodiment, a method for treatment of a human subject with essential thrombocytopenia (ET) is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg once daily, 10 mg once daily, 15 mg once daily, 20 mg once daily, and 25 mg once daily.

In one embodiment, a method for treatment of a human subject with chronic myelomonocytic leukemia (CMML) is provided, comprising administering a therapeutically effective amount of navitoclax selected from the group consisting 25 mg, 50 mg, 75 mg, 100 mg, 125 mg, 150 mg, 175 mg, 200 mg, 225 mg, 250 mg, 275 mg, and 300 mg and administering a therapeutically effective amount of ruxolitinib selected from the group consisting of 5 mg once daily, 10 mg once daily, 15 mg once daily, 20 mg once daily, and 25 mg once daily.

In one embodiment, a method for treatment of a human subject with is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the myelofibrosis is relapsed or refractory myelofibrosis; wherein the treatment of the human subject results in an improvement in a grade of bone marrow fibrosis relative to a baseline grade of bone marrow fibrosis; and wherein the improvement in the grade of the bone marrow fibrosis is measured according to the European consensus grading system.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; wherein the myelofibrosis is relapsed or refractory myelofibrosis; and wherein the treatment of the human subject results in an improvement in a grade of bone marrow fibrosis relative to a baseline grade of bone marrow fibrosis of ≥1. In one aspect, the therapeutically effective amount of navitoclax is 100 mg. In yet another aspect, the therapeutically effective amount of navitoclax is 200 mg.

In one embodiment, a method for treatment of a human subject with myelofibrosis is provided, comprising administering a therapeutically effective amount of navitoclax selected from the group consisting of 25 mg, 50 mg, 75 mg, 100 mg, 125 mg, 150 mg, 175 mg, 200 mg, 225 mg, 250 mg, 275 mg, and 300 mg; in combination with administering a therapeutically effective amount of ruxolitinib; wherein the myelofibrosis is relapsed or refractory myelofibrosis; wherein the treatment of the human subject results in an improvement in a grade of bone marrow fibrosis relative to a baseline grade of bone marrow fibrosis of ≥1; wherein the therapeutically effective amount of navitoclax is administered once a day.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein if the human subject has a platelet count of ≤150×10$^9$/L the effective amount of navitoclax comprises 100 mg, optionally increased to 200 mg navitoclax after ≥7 days if the human subject has a platelet count ≥75×10$^9$/L. In one aspect, the method for treatment is for first line treatment of myelofibrosis. In another aspect, the human subject has not previously received treatment with a JAK-2 inhibitor. In one aspect, a maximum dose of navitoclax is 300 mg. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein if the human subject has a platelet count of >150×10$^9$/L, the effective amount of navitoclax comprises 200 mg. In one aspect, the method for treatment is for first line treatment of myelofibrosis. In another aspect, the human subject has not previously received treatment with a JAK-2 inhibitor. In one aspect, a maximum dose of navitoclax comprises 300 mg. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 20 mg; wherein if the human subject has a platelet count of ≤150×10$^9$/L the effective amount of navitoclax comprises 100 mg, optionally increased to 200 mg navitoclax after ≥7 days if the human subject has a platelet count ≥75×10$^9$/L. In one aspect, the method for treatment is for first line treatment of myelofibrosis.

In another aspect, the human subject has not previously received treatment with a JAK-2 inhibitor. In one aspect, a maximum dose of navitoclax comprises 300 mg. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 20 mg; wherein if the human subject has a platelet count of >150×10$^9$/L, the effective amount of navitoclax comprises 200 mg. In one aspect, the method for treatment is for first line treatment of myelofibrosis. In another aspect, the human subject has not previously received treatment with a JAK-2 inhibitor. In one aspect, a maximum dose of navitoclax comprises 300 mg. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 20 mg; wherein (a) if the human subject has a platelet count of >150×10$^9$/L, the effective amount of navitoclax comprises 200 mg, (b) if the human subject has a platelet count of ≤150×10$^9$/L the effective amount of navitoclax comprises 100 mg, optionally increased to 200 mg navitoclax after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg. In one aspect, the method for treatment is for first line treatment of myelofibrosis. In another aspect, the human subject has not previously received treatment with a JAK-2 inhibitor. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the method for treatment is for first line treatment of myelofibrosis. In another aspect, the human subject has not previously received treatment with a JAK-2 inhibitor. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the method for treatment is for first line treatment of myelofibrosis. In another aspect, the human subject has not previously received treatment with a JAK-2 inhibitor. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for first line treatment of a human subject with myelofibrosis is provided, comprising administering a therapeutically effective of amount of navitoclax in combination with 10 mg of ruxolitinib twice daily to the human subject; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the human subject has not previously received treatment with a JAK-2 inhibitor. In another aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis who has not previously received therapy with a JAK-2 inhibitor is provided, comprising administering a therapeutically effective of amount of navitoclax in combination with 10 mg of ruxolitinib twice daily to the human subject; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for first line treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the human subject has not previously received treatment with a JAK-2 inhibitor. In another aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis who has not previously received therapy with a JAK-2 inhibitor is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein the effective amount of navitoclax in (a) or (b) may be increased to 300 mg administered once daily. In one aspect, the method for treatment is for first line treatment of myelofibrosis. In another aspect, the human subject has not previously received treatment with a JAK-2 inhibitor. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein after 24 weeks the effective amount of navitoclax in (a) or (b) may be increased to 300 mg administered once daily. In one aspect, the method for treatment is for first line treatment of myelofibrosis. In another aspect, the human subject has not previously received treatment with a JAK-2 inhibitor. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for first line treatment of a human subject with myelofibrosis is provided, comprising administering a therapeutically effective of amount of navitoclax in combination with 10 mg of ruxolitinib twice daily to the human subject; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein the effective amount of navitoclax in (a) or (b) may be increased to 300 mg administered once daily. In one aspect, the human subject has not previously received treatment with a JAK-2 inhibitor. In another aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis who has not previously received therapy with a JAK-2 inhibitor is provided, comprising administering a therapeutically effective of amount of navitoclax in combination with 10 mg of ruxolitinib twice daily to the human subject; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein the effective amount of navitoclax in (a) or (b) may be increased to 300 mg administered once daily. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$)

after week 24. In yet another aspect, the spleen reduction volume of at least 35% ($SVR_{35}$) is measured according to magnetic resonance imaging (MRI) or computed tomography (CT) scan, per International Working Group (IWG) criteria.

In one embodiment, a method for treatment of a human subject with myelofibrosis who has not previously received therapy with a JAK-2 inhibitor is provided, comprising administering a therapeutically effective of amount of navitoclax in combination with 10 mg of ruxolitinib twice daily to the human subject; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein after 24 weeks the effective amount of navitoclax in (a) or (b) may be increased to 300 mg administered once daily. In one aspect, the human subject achieves a spleen reduction volume of at least 35% ($SVR_{35}$). In another aspect, the human subject achieves a spleen reduction volume of at least 35% ($SVR_{35}$) by week 24. In yet another aspect, the human subject achieves a spleen reduction volume of at least 35% ($SVR_{35}$) after week 24. In yet another aspect, the spleen reduction volume of at least 35% ($SVR_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, and (b) if the human subject has a platelet count of ≤150×10$^9$/L the effective amount of navitoclax comprises 100 mg administered once daily, optionally increased to 200 mg administered once daily. In one aspect, the myelofibrosis is relapsed or refractory. In one aspect, the human subject achieves a spleen reduction volume of at least 35% ($SVR_{35}$). In another aspect, the human subject achieves a spleen reduction volume of at least 35% ($SVR_{35}$) by week 24. In yet another aspect, the human subject achieves a spleen reduction volume of at least 35% ($SVR_{35}$) after week 24. In yet another aspect, the spleen reduction volume of at least 35% ($SVR_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the myelofibrosis is relapsed or refractory. In one aspect, the human subject achieves a spleen reduction volume of at least 35% ($SVR_{35}$). In another aspect, the human subject achieves a spleen reduction volume of at least 35% ($SVR_{35}$) by week 24. In yet another aspect, the human subject achieves a spleen reduction volume of at least 35% ($SVR_{35}$) after week 24. In yet another aspect, the spleen reduction volume of at least 35% ($SVR_{35}$) is measured according to magnetic resonance imaging (MRI) or computed tomography (CT) scan, per International Working Group (IWG) criteria.

In one embodiment, a method for treatment of a human subject with relapsed or refractory myelofibrosis is provided, comprising administering a therapeutically effective of amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, (b) if the human subject has a platelet count of ≤150×10$^9$/L the effective amount of navitoclax comprises 100 mg administered once daily, optionally increased to 200 mg navitoclax administered once daily after ≥7 days if the human subject has a platelet count ≥75×10$^9$/L; and wherein if after 24 weeks the patient fails to achieve a spleen reduction volume (SVR) of at least 10%, the effective amount of navitoclax in (a) or (b) may be increased to 300 mg administered once daily. In one aspect, the human subject achieves a spleen reduction volume of at least 35% ($SVR_{35}$). In another aspect, the human subject achieves a spleen reduction volume of at least 35% ($SVR_{35}$) by week 24. In yet another aspect, the human subject achieves a spleen reduction volume of at least 35% ($SVR_{35}$) after week 24. In yet another aspect, the spleen reduction volume of at least 35% ($SVR_{35}$) is measured according to magnetic resonance imaging (MRI) or computed tomography (CT) scan, per International Working Group (IWG) criteria.

In one embodiment, a method for treatment of a human subject with relapsed or refractory myelofibrosis is provided, comprising administering a therapeutically effective amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, and (b) if the human subject has a platelet count of ≤150×10$^9$/L the effective amount of navitoclax comprises 100 mg administered once daily, optionally increased to 200 mg administered once daily. In one aspect, the human subject achieves a spleen reduction volume of at least 35% ($SVR_{35}$). In another aspect, the human subject achieves a spleen reduction volume of at least 35% ($SVR_{35}$) by week 24. In yet another aspect, the human subject achieves a spleen reduction volume of at least 35% ($SVR_{35}$) after week 24. In yet another aspect, the spleen reduction volume of at least 35% ($SVR_{35}$) is measured according to magnetic resonance imaging (MRI) or computed tomography (CT) scan, per International Working Group (IWG) criteria.

In one embodiment, a method for treatment of a human subject with relapsed or refractory myelofibrosis is provided, comprising administering a therapeutically effective amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, and (b) if the human subject has a platelet count of ≤150×10$^9$/L the effective amount of navitoclax comprises 100 mg administered once daily, optionally increased to 200 mg administered once daily. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with relapsed or refractory myelofibrosis is provided, comprising administering a therapeutically effective amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, and (b) if the human subject has a platelet count of ≤150×10$^9$/L the effective amount of navitoclax comprises 100 mg administered once daily, optionally increased to 200 mg administered once daily. In one aspect, the effective amount of navitoclax is optionally increased to 300 mg administered once daily. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with relapsed or refractory myelofibrosis is provided, comprising administering a therapeutically effective amount of navitoclax in combination with a therapeutically effective amount of ruxolitinib to the human subject; wherein the effective amount of ruxolitinib comprises 10 mg administered twice daily; wherein (a) if the human subject has a platelet count of >150×10$^9$/L, the effective amount of navitoclax comprises 200 mg navitoclax administered once daily, and (b) if the human subject has a platelet count of ≤150×10$^9$/L the effective amount of navitoclax comprises 100 mg administered once daily, optionally increased to 200 mg administered once daily. In one aspect, the effective amount of navitoclax is optionally increased to 300 mg administered once daily. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective amount of navitoclax in combination with a therapeutically effective amount of ruxolitinib to the human subject; wherein the effective amount of ruxolitinib comprises 20 mg; wherein (a) if the human subject has a platelet count of >150×10$^9$/L, the effective amount of navitoclax comprises 200 mg, and (b) if the human subject has a platelet count of ≤150×10$^9$/L the effective amount of navitoclax comprises 100 mg, optionally increased to 200 mg. In one aspect, the myelofibrosis is relapsed or refractory. In one aspect, the human subject achieves a spleen reduction volume of at least 35% (SVR$_{35}$). In another aspect, the human subject achieves a spleen reduction volume of at least 35% (SVR$_{35}$) by week 24. In yet another aspect, the human subject achieves a spleen reduction volume of at least 35% (SVR$_{35}$) after week 24. In yet another aspect, the spleen reduction volume of at least 35% (SVR$_{35}$) is measured according to magnetic resonance imaging (MRI) or computed tomography (CT) scan, per International Working Group (IWG) criteria.

In one embodiment, a method for treatment of a human subject with myelofibrosis is provided, comprising administering a therapeutically effective of amount of navitoclax in combination with a therapeutically effective amount of ruxolitinib to the human subject; wherein if the human subject has a platelet count of >200×10$^9$/L, the effective amount of ruxolitinib comprises 20 mg twice daily, and if the human subject has a platelet count of count 100×10$^9$/L to 200×10$^9$/L, the effective amount of ruxolitinib comprises 15 mg twice daily; wherein if the human subject has a platelet count of >150×10$^9$/L, the effective daily amount of navitoclax comprises 200 mg; wherein if the human subject has a platelet count of ≤150×10$^9$/L, the effective daily amount of navitoclax comprises 100 mg, optionally increased to 200 mg navitoclax after ≥7 days if the human subject has a platelet count ≥75×10$^9$/L; and wherein if the human subject fails to achieve SVR$_{35}$ by week 24 of treatment, the navitoclax dose may be optionally increased to 300 mg once daily.

In one embodiment, a method for treatment of a human subject with myelofibrosis is provided, comprising administering a therapeutically effective of amount of navitoclax in combination with a therapeutically effective amount of ruxolitinib to the human subject; wherein if the human subject has a platelet count of >200×10$^9$/L, the effective amount of ruxolitinib comprises 20 mg twice daily, wherein if the human subject has a platelet count of count 100×10$^9$/L to 200×10$^9$/L, the effective amount of ruxolitinib comprises 15 mg twice daily; wherein if the human subject has a platelet count of >150×10$^9$/L, the effective daily amount of navitoclax comprises 200 mg; wherein if the human subject has a platelet count of ≤150×10$^9$/L the effective daily amount of navitoclax comprises 100 mg, optionally increased to 200 mg navitoclax after ≥7 days if the human subject has a platelet count ≥75×10$^9$/L; and wherein if the human subject fails to achieve SVR$_{35}$ by week 24 of treatment, the navitoclax dose may be optionally increased to 300 mg once daily.

In one embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia, wherein if platelets ≥75×10$^9$/L, the current dose of navitoclax is maintained or escalated by one dose level not to exceed 200 mg once daily or 300 mg. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia, wherein if platelets ≥75×10$^9$/L, the current dose of navitoclax is maintained.

In one embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets ≥75×10$^9$/L, the current dose of navitoclax is maintained or escalated by one dose level not to exceed 200 mg once daily or 300 mg. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia, wherein if platelets ≥75×10$^9$/L, the current dose of navitoclax is maintained.

In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <75×10$^9$/L–≥50×10$^9$/L, the current navitoclax dose level is maintained or the current navitoclax dose level is reduced one dose level lower. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <75×10$^9$/L–≥50×10$^9$/L, the current navitoclax dose level is maintained or the current navitoclax dose level is reduced to one dose level lower, and the dose of ruxolitinib is optionally reduced as well, wherein the platelet count is rechecked approximately every 7 days until ≥2 consecutive lab values indicate stable platelet count.

In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <75×10$^9$/L–≥50×10$^9$/L, the current navitoclax dose level is maintained or the current navitoclax dose level is reduced one dose level lower. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <75×10$^9$/L–≥50×10$^9$/L, the current navitoclax dose level is maintained or the current navitoclax dose level is reduced to one dose level lower, and the dose of ruxolitinib is optionally reduced as well. In another embodiment, Platelet count should be rechecked approximately every 7 days until ≥2 consecutive lab values indicate stable platelet count.

In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <50×10$^9$/L, the current navitoclax dose level is interrupted. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <50×10$^9$/L, the current navitoclax dose level is interrupted, and the dose of ruxolitinib is interrupted wherein the platelet count is rechecked approximately 2-3 days until recovery to ≥50×10$^9$/L wherein navitoclax administration is resumed at one dose level lower and ruxolitinib is optionally reduced as well and wherein platelet count should be rechecked approximately every 7 days until ≥2 consecutive lab values indicate stable platelet count.

In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <50×10$^9$/L, the current navitoclax dose level is interrupted or discontinued. In another embodiment, a method for treatment of a human subject with myelofibrosis is provided, comprising administering a therapeutically effective of amount of navitoclax in combination with a therapeutically effective amount of ruxolitinib to the human subject; wherein the dose of navitoclax may be adjusted for thrombocytopenia wherein if platelets <50×10$^9$/L, the current navitoclax dose level is interrupted, wherein the platelet count is rechecked approximately 2-3 days until recovery to ≥50×10$^9$/L wherein navitoclax administration is resumed at one dose level lower and wherein platelet count should be rechecked approximately every 7 days until ≥2 consecutive lab values indicate stable platelet count.

In one embodiment, a method for treatment of a human subject with myelofibrosis is provided, comprising administering a therapeutically effective of amount of navitoclax in combination with a therapeutically effective amount of ruxolitinib to the human subject; wherein if the human subject has a platelet count of >150×10$^9$/L, the effective daily amount of navitoclax comprises 200 mg; wherein if the human subject has a platelet count of ≤150×10$^9$/L, the effective daily amount of navitoclax comprises 100 mg, wherein the effective daily amount of navitoclax is optionally increased to 200 mg navitoclax, if 100 mg dose is tolerable; wherein the dose may be increased to 300 mg once daily for subjects with sub-optimal spleen response defined as failure to achieve a spleen volume reduction of at least 10% after 24 weeks.

In one embodiment, a method for treatment of a human subject with myelofibrosis is provided, comprising administering a therapeutically effective of amount of navitoclax in combination with a therapeutically effective amount of ruxolitinib to the human subject; wherein human subjects receiving ruxolitinib continue at a current stable dose of ≥10 mg twice daily, wherein subjects not receiving ruxolitinib receive ruxolitinib at a dose of 10 mg twice daily; and wherein ruxolitinib dose adjustment in subjects with hepatic or renal impairment is optionally adjusted.

In one embodiment, a method for treatment of a human subject with myelofibrosis or MPN (myeloproliferative neoplasms)-related disorders is provided comprising administering a therapeutically effective amount of navitoclax. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or MPN (myeloproliferative neoplasms)-related disorders who have failed, are intolerant to, or refuse standard therapy is provided comprising administering a therapeutically effective amount of navitoclax. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or MPN (myeloproliferative neoplasms)-related disorders who have failed, are intolerant to, or refuse standard therapy is provided, comprising administering a therapeutically effective amount of navitoclax wherein based on individual tolerability including platelet counts, the dose of navitoclax may be increased weekly in a stepwise fashion. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or MPN (myeloproliferative neoplasms)-related disorders who have failed, are intolerant to, or refuse standard therapy is provided, comprising administering a therapeutically effective amount of navitoclax wherein based on individual tolerability including platelet counts, the dose of navitoclax may be increased weekly in a stepwise fashion, wherein the dose of navitoclax may be increased every ≥7 days to the next dose level up to a maximum dose of navitoclax 300 mg once daily.

In one embodiment, a method for treatment of a human subject with myelofibrosis or MPN (myeloproliferative neoplasms)-related disorders who have failed, are intolerant to, or refuse standard therapy is provided, comprising administering a therapeutically effective amount of navitoclax wherein based on individual tolerability including platelet counts, the dose of navitoclax may be increased weekly in a stepwise fashion, wherein the dose of navitoclax may be increased every ≥7 days to the next dose level up to a maximum dose of navitoclax 300 mg once daily, provided the platelet count is >100×10$^9$/L. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or MPN (myeloproliferative neoplasms)-related disorders who have failed, are intolerant to, or refuse standard therapy is provided, comprising administering 50 mg of navitoclax once daily wherein based on individual tolerability including platelet counts, the dose of navitoclax may be increased weekly in a stepwise fashion, wherein the dose of navitoclax may be increased every ≥7 days to the next dose level up to a maximum dose of navitoclax 300 mg once daily, provided the platelet count is >100×10$^9$/L. In some embodiments, the MPN-related disorder comprises polycythemia vera (PCV), essential thrombocytopenia (ET), or chronic myelomonocytic leukemia (CMML).

In one embodiment, a method for treatment of a human subject with myelofibrosis or MPN (myeloproliferative neoplasms)-related disorders is provided, comprising administering a therapeutically effective amount of navitoclax in combination with a therapeutically effective amount of ruxolitinib. In some embodiments, the MPN-related disorder comprises polycythemia vera (PCV), essential thrombocytopenia (ET), or chronic myelomonocytic leukemia (CMML).

In one embodiment, a method for treatment of a human subject with primary myelofibrosis (PMF) or secondary myelofibrosis (SMF), is provided, comprising administering a therapeutically effective amount of navitoclax in combination with a therapeutically effective amount of ruxolitinib.

In one embodiment, a method for treatment of a human subject with primary myelofibrosis (PMF) or secondary myelofibrosis (SMF), is provided, comprising administering a therapeutically effective amount of navitoclax in combination with a therapeutically effective amount of ruxolitinib wherein the human subject has received ruxolitinib therapy for at least 12 weeks prior to starting navitoclax.

In one embodiment, a method for treatment of a human subject with primary myelofibrosis (PMF) or secondary myelofibrosis (SMF), is provided, comprising administering a therapeutically effective amount of navitoclax in combination with a therapeutically effective amount of ruxolitinib wherein the human subjects has received ruxolitinib therapy for at least 12 weeks prior to starting navitoclax, wherein the human subject is currently on a stable dose of ≥10 mg of ruxolitinib twice daily.

In one embodiment, a method for treatment of a human subject with primary myelofibrosis (PMF) or secondary myelofibrosis (SMF), is provided, comprising administering a therapeutically effective amount of navitoclax in combination with a therapeutically effective amount of ruxolitinib wherein the human subject has received ruxolitinib therapy for at least 12 weeks prior to starting navitoclax, wherein the human subject is currently on a stable dose of ≥10 mg of ruxolitinib twice daily.

In one embodiment, a method for treatment of a human subject with primary myelofibrosis (PMF) or secondary myelofibrosis (SMF), is provided, comprising administering a therapeutically effective amount of navitoclax in combination with a therapeutically effective amount of ruxolitinib wherein the human subject has received ruxolitinib therapy for at least 12 weeks prior to starting navitoclax, wherein the human subject is currently on a stable dose of ≥10 mg of ruxolitinib twice daily, comprising administering a therapeutically effective amount of navitoclax; wherein based on individual tolerability including platelet counts, the dose of navitoclax is increased in a stepwise fashion until at least 300 mg. navitoclax is administered once daily.

In one embodiment, a method for treatment of a human subject with primarily myelofibrosis (PMF) or secondary myelofibrosis (SMF), is provided, comprising administering a therapeutically effective amount of navitoclax in combination with a therapeutically effective amount of ruxolitinib wherein the human subject has received ruxolitinib therapy for at least 12 weeks prior to starting navitoclax, wherein the human subject is currently on a stable dose of ≥10 mg of ruxolitinib twice daily, comprising administering a therapeutically effective amount of navitoclax wherein based on individual tolerability including platelet counts, the dose of navitoclax is increased weekly in a stepwise fashion wherein the dose of navitoclax is increased every ≥7 days up to a maximum dose of navitoclax 300 mg administered once daily.

In one embodiment, a method for treatment of a human subject with primarily myelofibrosis (PMF) or secondary myelofibrosis (SMF), is provided, comprising administering a therapeutically effective amount of navitoclax in combination with a therapeutically effective amount of ruxolitinib wherein the human subject has received ruxolitinib therapy for at least 12 weeks prior to starting navitoclax, wherein the human subject is currently on a stable dose of ≥10 mg of ruxolitinib twice daily, comprising administering a therapeutically effective amount of navitoclax wherein based on individual tolerability including platelet counts, the dose of navitoclax may be increased weekly in a stepwise fashion wherein the dose of navitoclax is increased every ≥7 days up to a maximum dose of navitoclax 300 mg QD, provided the platelet count of the human subject is >100×10$^9$/L.

In one embodiment, a method for treatment of a human subject with primary myelofibrosis (PMF) or secondary myelofibrosis (SMF), is provided, comprising administering a therapeutically effective amount of navitoclax in combination with a therapeutically effective amount of ruxolitinib wherein the human subject has received ruxolitinib therapy for at least 12 weeks prior to starting navitoclax, wherein the human subject is currently on a stable dose of ≥10 mg of ruxolitinib twice daily, comprising administering 50 mg of navitoclax once daily wherein based on individual tolerability including platelet counts, the dose of navitoclax is increased weekly in a stepwise fashion wherein the dose of navitoclax is increased every ≥7 days up to a maximum dose of navitoclax 300 mg once daily, provided the platelet count of the human subject is >100×10$^9$/L.

In one embodiment, a method for treatment of a human subject having CMML (chronic myelomonocytic leukemia) is provided, comprising administering a therapeutically effective amount of navitoclax.

In one embodiment, a method for treatment of a human subject having CMML (chronic myelomonocytic leukemia) is provided, comprising administering a therapeutically effective amount of navitoclax, optionally with a therapeutic amount of ruxolitinib.

In one embodiment, a method for treatment of a human subject CMML (chronic myelomonocytic leukemia) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax.

In one embodiment, a method for treatment of a human subject CMML (chronic myelomonocytic leukemia) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily.

In one embodiment, a method for treatment of a human subject having CMML (chronic myelomonocytic leukemia) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib.

In one embodiment, a method for treatment of a human subject having CMML (chronic myelomonocytic leukemia) is provided, comprising administering one of 50 mg, 100 mg, 150 mg, 200 mg, 250 mg, or 300 mg of navitoclax once daily, optionally with a therapeutically effective amount of ruxolitinib.

In one embodiment, a method for treatment of a human subject having CMML (chronic myelomonocytic leukemia) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject having CMML (chronic myelomonocytic leukemia) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib selected from the group consisting of 5 mg once daily, 10 mg once daily, 15 mg once daily, 20 mg once daily, and 25 mg once daily.

In one embodiment, a method for treatment of a human subject having polycythemia vera (PCV) is provided, comprising administering a therapeutically effective amount of navitoclax.

In one embodiment, a method for treatment of a human subject having polycythemia vera (ACV) is provided, comprising administering a therapeutically effective amount of navitoclax, optionally with a therapeutic amount of ruxolitinib.

In one embodiment, a method for treatment of a human subject having polycythemia vera (PCV) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax.

In one embodiment, a method for treatment of a human subject having polycythemia vera (PCV) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily.

In one embodiment, a method for treatment of a human subject having polycythemia vera (ACV) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib.

In one embodiment, a method for treatment of a human subject having polycythemia vera (PCV) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib.

In one embodiment, a method for treatment of a human subject having polycythemia vera (PCV) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject having polycythemia vera (PCV) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib selected from the group consisting of 5 mg once daily, 10 mg once daily, 15 mg once daily, 20 mg once daily, and 25 mg once daily.

In one embodiment, a method for treatment of a human subject having essential thrombocytopenia (ET) is provided, comprising administering a therapeutically effective amount of navitoclax.

In one embodiment, a method for treatment of a human subject having essential thrombocytopenia (ET) is provided, comprising administering a therapeutically effective amount of navitoclax, optionally with a therapeutic amount of ruxolitinib.

In one embodiment, a method for treatment of a human subject having essential thrombocytopenia (ET) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax.

In one embodiment, a method for treatment of a human subject having essential thrombocytopenia (ET) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily.

In one embodiment, a method for treatment of a human subject having essential thrombocytopenia (ET) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib.

In one embodiment, a method for treatment of a human subject having essential thrombocytopenia (ET) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib.

In one embodiment, a method for treatment of a human subject having essential thrombocytopenia (ET) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib selected from the group consisting of 5 mg twice daily, 10 mg twice daily, 15 mg twice daily, 20 mg twice daily, and 25 mg twice daily.

In one embodiment, a method for treatment of a human subject having essential thrombocytopenia (ET) is provided, comprising administering one of 25 mg, 50 mg, 75 mg, 100 mg, 125 mg, 150 mg, 175 mg, 200 mg, 225 mg, 250 mg, 275 mg, and 300 mg of navitoclax once daily, optionally with a therapeutically effective amount of ruxolitinib selected from the group consisting of 5 mg once daily, 10 mg once daily, 15 mg once daily, 20 mg once daily, and 25 mg once daily.

In any of the embodiments disclosed herein, the effective amount of navitoclax can comprise 25 mg.

In any of the embodiments disclosed herein, the effective amount of navitoclax can comprise 50 mg.

In any of the embodiments disclosed herein, the effective amount of navitoclax can comprise 75 mg.

In any of the embodiments disclosed herein, the effective amount of navitoclax can comprise 100 mg.

In any of the embodiments disclosed herein, the effective amount of navitoclax can comprise 125 mg.

In any of the embodiments disclosed herein, the effective amount of navitoclax can comprise 150 mg.

In any of the embodiments disclosed herein, the effective amount of navitoclax can comprise 175 mg.

In any of the embodiments disclosed herein, the effective amount of navitoclax can comprise 200 mg.

In any of the embodiments disclosed herein, the effective amount of navitoclax can comprise 225 mg.

In any of the embodiments disclosed herein, the effective amount of navitoclax can comprise 250 mg.

In any of the embodiments disclosed herein, the effective amount of navitoclax can comprise 275 mg.

In any of the embodiments disclosed herein, the effective amount of navitoclax can comprise 300 mg.

In any of the embodiments disclosed herein, the effective amount of navitoclax can comprise more than 300 mg.

In any of the embodiments disclosed herein, the effective amount of navitoclax can comprise 50 mg administered once daily.

In any of the embodiments disclosed herein, the effective amount of navitoclax can comprise 75 mg administered once daily.

In any of the embodiments disclosed herein, the effective amount of navitoclax can comprise 100 mg administered once daily.

In any of the embodiments disclosed herein, the effective amount of navitoclax can comprise 125 mg administered once daily.

In any of the embodiments disclosed herein, the effective amount of navitoclax can comprise 150 mg administered once daily.

In any of the embodiments disclosed herein, the effective amount of navitoclax can comprise 175 mg administered once daily.

In any of the embodiments disclosed herein, the effective amount of navitoclax can comprise 200 mg administered once daily.

In any of the embodiments disclosed herein, the effective amount of navitoclax can comprise 225 mg administered once daily.

In any of the embodiments disclosed herein, the effective amount of navitoclax can comprise 250 mg administered once daily.

In any of the embodiments disclosed herein, the effective amount of navitoclax can comprise 275 mg administered once daily.

In any of the embodiments disclosed herein, the effective amount of navitoclax can comprise 300 mg administered once daily.

In any of the embodiments disclosed herein, the effective amount of navitoclax can comprise more than 300 mg administered once daily.

In any of the embodiments disclosed herein, the effective amount of navitoclax can comprise 50 mg administered once daily, optionally increased to 100 mg administered once daily.

In any of the embodiments disclosed herein, the effective amount of navitoclax can comprise 100 mg administered once daily, optionally increased to 150 mg administered once daily.

In any of the embodiments disclosed herein, the effective amount of navitoclax can comprise 100 mg administered once daily, optionally increased to 200 mg administered once daily.

In any of the embodiments disclosed herein, the effective amount of navitoclax can comprise 150 mg administered once daily, optionally increased to 200 mg administered once daily.

In any of the embodiments disclosed herein, the effective amount of navitoclax can comprise 150 mg administered once daily, optionally increased to 250 mg administered once daily.

In any of the embodiments disclosed herein, the effective amount of navitoclax can comprise 150 mg administered once daily, optionally increased to 200 mg administered once daily.

In any of the embodiments disclosed herein, the effective amount of navitoclax can comprise 150 mg administered once daily, optionally increased to 250 mg administered once daily.

In any of the embodiments disclosed herein, the effective amount of navitoclax can comprise 200 mg administered once daily, optionally increased to 250 mg administered once daily.

In any of the embodiments disclosed herein, the effective amount of navitoclax can comprise 200 mg administered once daily, optionally increased to 300 mg administered once daily.

In any of the embodiments disclosed herein, the effective amount of navitoclax can comprise 100 mg administered once daily, optionally increased to 200 mg administered once daily after ≥7 days if the human subject has a platelet count ≥75×10$^9$/L.

In any of the embodiments disclosed herein, the effective amount of navitoclax can be increased to 300 mg administered once daily.

In any of the embodiments disclosed herein, the effective amount of navitoclax can be increased to 300 mg administered once daily, if after 24 weeks the patient fails to achieve a spleen reduction volume (SVR) of at least 10%.

In any of the embodiments disclosed herein, the effective amount of ruxolitinib can comprise 5 mg administered once daily.

In any of the embodiments disclosed herein, the effective amount of ruxolitinib can comprise 10 mg administered once daily.

In any of the embodiments disclosed herein, the effective amount of ruxolitinib can comprise 15 mg administered once daily.

In any of the embodiments disclosed herein, the effective amount of ruxolitinib can comprise 20 mg administered once daily.

In any of the embodiments disclosed herein, the effective amount of ruxolitinib can comprise 25 mg administered once daily.

In any of the embodiments disclosed herein, the effective amount of ruxolitinib can comprise more than 25 mg administered once daily.

In any of the embodiments disclosed herein, the effective amount of ruxolitinib can comprise 5 mg administered twice daily.

In any of the embodiments disclosed herein, the effective amount of ruxolitinib can comprise 10 mg administered twice daily.

In any of the embodiments disclosed herein, the effective amount of ruxolitinib can comprise 15 mg administered twice daily.

In any of the embodiments disclosed herein, the effective amount of ruxolitinib can comprise 20 mg administered twice daily.

In any of the embodiments disclosed herein, the effective amount of ruxolitinib can comprise 25 mg administered twice daily.

In any of the embodiments disclosed herein, the effective amount of ruxolitinib can comprise more than 25 mg administered twice daily.

In any of the embodiments disclosed herein, the effective amount of ruxolitinib can comprise 5 mg.

In any of the embodiments disclosed herein, the effective amount of ruxolitinib can comprise 10 mg.

In any of the embodiments disclosed herein, the effective amount of ruxolitinib can comprise 15 mg.

In any of the embodiments disclosed herein, the effective amount of ruxolitinib can comprise 20 mg.

In any of the embodiments disclosed herein, the effective amount of ruxolitinib can comprise 25 mg.

In any of the embodiments disclosed herein, the effective amount of ruxolitinib can comprise 30 mg.

In any of the embodiments disclosed herein, the effective amount of ruxolitinib can comprise 40 mg.

In any of the embodiments disclosed herein, the effective amount of ruxolitinib can comprise 50 mg.

In any of the embodiments disclosed herein, the effective amount of ruxolitinib can comprise more than 50 mg.

In any of the embodiments disclosed herein, the administration of navitoclax can comprise oral administration.

In any of the embodiments disclosed herein, the administration of ruxolitinib can comprise oral administration.

In any of the embodiments disclosed herein, the administration of navitoclax can comprise oral administration and the administration of ruxolitinib can comprise oral administration.

In any of the embodiments disclosed herein, the human subject can achieve a spleen reduction volume of at least 35% (SVR$_{35}$). In any of the foregoing embodiments, the human subject can achieve a spleen reduction volume of at least 35% (SVR$_{35}$) by week 24. In any of the foregoing embodiments, the human subject can achieve a spleen reduction volume of at least 35% (SVR$_{35}$) after week 24.

In any of the embodiments disclosed herein, the spleen reduction volume of at least 35% (SVR$_{35}$) can be measured according to magnetic resonance imaging (MRI) or computed tomography (CT) scan, per International Working Group (IWG) criteria.

In any of the embodiments disclosed herein, if the human subject has a platelet count of >150×10$^9$/L, the effective amount of ruxolitinib can comprise 20 mg twice daily.

In any of the embodiments disclosed herein, if the human subject has a platelet count of >200×10$^9$/L, the effective amount of ruxolitinib can comprise 20 mg twice daily.

In any of the embodiments disclosed herein, if the human subject has a platelet count of 100×10$^9$/L to 200×10$^9$/L, the effective amount of ruxolitinib can comprise 15 mg twice daily.

In any of the embodiments disclosed herein, if the human subject has a platelet count of >150×10$^9$/L, the effective daily amount of navitoclax can comprise 200 mg.

In any of the embodiments disclosed herein, if the human subject has a platelet count of ≤150×10$^9$/L, the effective daily amount of navitoclax can comprise 100 mg, optionally increased to 200 mg navitoclax after ≥7 days if the human subject has a platelet count ≥75×10$^9$/L.

In any of the embodiments disclosed herein, the navitoclax dose may be increased to 300 mg once daily based on platelet count for subjects with sub-optimal spleen response, defined as failure to achieve a spleen volume reduction of at least 10%.

In any of the embodiments disclosed herein, if the human subject has a platelet count of ≥75×10$^9$/L, the current dose of navitoclax can be maintained.

In any of the embodiments disclosed herein, if the human subject has a platelet count of ≥75×10$^9$/L, the current dose of navitoclax can be escalated to 200 mg or optionally 300 mg once daily.

In any of the embodiments disclosed herein, if the human subject has a platelet count of $\geq 75 \times 10^9$/L, the current dose of navitoclax can be maintained, wherein, the dose of navitoclax may be adjusted for thrombocytopenia.

In any of the embodiments disclosed herein, if the human subject has a platelet count of $<75 \times 10^9$/L–$\geq 50 \times 10^9$/L, the current navitoclax dose level can be maintained or reduced.

In any of the embodiments disclosed herein, if the human subject has a platelet count of $<50 \times 10^9$/L, the current navitoclax dose level can be interrupted, wherein the platelet count is rechecked approximately 2-3 days until recovery to $\geq 50 \times 10^9$/L wherein navitoclax administration can be resumed, optionally at a lower dose level.

In any of the embodiments disclosed herein, the dose of navitoclax can only be escalated if current dose of navitoclax has been administered for at least 7 days, wherein platelet count can be rechecked approximately 7 days after navitoclax dose escalation.

In any of the embodiments disclosed herein, the daily therapeutically effective amount of navitoclax administered to the human subject if the human subject has a platelet count of $>150 \times 10^9$/L can comprise 200 mg.

In any of the embodiments disclosed herein, the daily therapeutically effective amount of navitoclax administered to the human subject if the human subject has a platelet count of $\leq 150 \times 10^9$/L can comprise 100 mg.

In any of the embodiments disclosed herein, the daily therapeutically effective amount of navitoclax administered to the human subject if the human subject has a platelet count of $>150 \times 10^9$/L can comprise 300 mg.

In any of the embodiments disclosed herein, the daily therapeutically effective amount of navitoclax administered to the human subject if the human subject has a platelet count of $\leq 150 \times 10^9$/L can comprise 200 mg.

In any of the embodiments disclosed herein, the daily therapeutically effective amount of navitoclax administered to the human subject if the human subject has a platelet count of $>200 \times 10^9$/L can comprise 200 mg.

In any of the embodiments disclosed herein, the daily therapeutically effective amount of navitoclax administered to the human subject if the human subject has a platelet count of $\leq 200 \times 10^9$/L can comprise 100 mg.

In any of the embodiments disclosed herein, the daily therapeutically effective amount of navitoclax administered to the human subject if the human subject has a platelet count of $>200 \times 10^9$/L can comprise 300 mg.

In any of the embodiments disclosed herein, the daily therapeutically effective amount of navitoclax administered to the human subject if the human subject has a platelet count of $\leq 200 \times 10^9$/L can comprise 200 mg.

In any of the embodiments disclosed herein, human subjects receiving ruxolitinib at Screening can continue at the current stable dose of $\geq 10$ mg twice daily.

In any of the embodiments disclosed herein, human wherein subjects not receiving ruxolitinib before starting navitoclax can receive ruxolitinib at a dose of 10 mg twice daily.

In any of the embodiments disclosed herein, the ruxolitinib dose can be adjusted in subjects with hepatic or renal impairment.

In any of the embodiments disclosed herein, the navitoclax dose can be adjusted in subjects with hepatic or renal impairment.

In any of the embodiments disclosed herein, the ruxolitinib dose can be adjusted, modified, or discontinued temporarily or permanently in subjects receiving treatment with a CYP3A substrate or CYP3A inhibitor.

In any of the embodiments disclosed herein, the navitoclax dose can be adjusted, modified, or discontinued temporarily or permanently in subjects receiving treatment with a CYP3A substrate or CYP3A inhibitor.

In any of the embodiments disclosed herein, the ruxolitinib dose can be adjusted, modified, or discontinued temporarily or permanently in subjects with abnormal hemoglobin levels.

In any of the embodiments disclosed herein, the ruxolitinib dose can be adjusted, modified, or discontinued temporarily or permanently in subjects with abnormal platelet levels.

In any of the embodiments disclosed herein, the navitoclax dose can be adjusted, modified, or discontinued temporarily or permanently in subjects with abnormal platelet levels.

In any of the embodiments disclosed herein, the ruxolitinib dose can be adjusted, modified, or discontinued temporarily or permanently in subjects with abnormal absolute neutrophil count (ANC).

In any of the embodiments disclosed herein, the myelofibrosis can comprise relapsed/refractory (R/R) myelofibrosis.

In any of the embodiments disclosed herein, the myelofibrosis can comprise intermediate or intermediate-risk primary myelofibrosis.

In any of the embodiments disclosed herein, the myelofibrosis can comprise high-risk primary myelofibrosis.

In any of the embodiments disclosed herein, the myelofibrosis can comprise intermediate or intermediate-risk secondary myelofibrosis.

In any of the embodiments disclosed herein, the myelofibrosis can comprise high-risk secondary myelofibrosis.

In any of the embodiments disclosed herein, the myelofibrosis can comprise post-polycythemia vera (post-PCV) myelofibrosis.

In any of the embodiments disclosed herein, the myelofibrosis can comprise post-essential thrombocytopenia (post-ET) myelofibrosis.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent documents incorporated by reference contradict the disclosure contained in the specification; the specification will supersede any contradictory material.

Generally, nomenclatures used in connection with cell and tissue culture, molecular biology, immunology, microbiology, genetics and protein and nucleic acid chemistry and hybridization described herein are those well-known and commonly used in the art. The nomenclatures used in connection with analytical chemistry, synthetic organic chemistry, and medicinal and pharmaceutical chemistry described herein are those well-known and commonly used in the art unless otherwise indicated.

So that the disclosure may be more readily understood, select terms are defined below.

Definitions

As used in the specification and the appended claims, unless specified to the contrary, the following terms have the meaning indicated:

The term "ANC" as used herein refers to absolute neutrophil count.

The term "aPTT" as used herein refers to activated partial thromboplastin time.

The term "ALT" as used herein refers to alanine aminotransferase.

The term "AST" as used herein refers to aspartate aminotransferase.

The term "BID" as used herein refers to twice a day.

The term "CYP3A" as used herein refers to Cytochrome P450 3A.

The term "CT" as used herein refers to computed tomography, as in CT scan.

The term "ECOG" as used herein refers to Eastern Cooperative Oncology Group.

The term "INR" as used herein refers to International Normalized Ratio.

The term "IWG" as used herein refers to International Working Group, as in IWG criteria for myelofibrosis, described in Tefferi et al., Blood, 22 Aug. 2013, Vol. 122, Number 8, hereby incorporated by reference in its entirety.

The term "JAK2" or "JAK-2" as used herein refers to Janus Kinase 2.

The term "LMWH" as used herein refers to low-molecular-weight heparin.

The term "MF" as used herein refers to myelofibrosis.

The term "MRI" as used herein refers to magnetic resonance imaging.

The term "PET-MF" as used herein refers to post-essential thrombocythemia myelofibrosis.

The term "PPV-MF" as used herein refers to post-polycythemia vera myelofibrosis.

The term "QD" as used herein refers to once a day.

The term "SVR" as used herein refers to spleen volume reduction.

The term "ULN" as used herein refers upper normal limit.

The term "relapsed" refers to disease that reappears or grows again after a period of remission.

The term "refractory" is used to describe when the disease does not respond to treatment (meaning that the cancer cells continue to group or when the response to treatment does not last, very long.

The term "therapeutically effective amount" or "effective amount" as used herein refers to a sufficient amount of the compound to treat disorders, at a reasonable benefit/risk ratio applicable to any medical treatment within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound(s) employed; and like factors n in the medical arts.

The term "in combination" means that the drugs administered are given either simultaneously or sequentially. If given sequentially, one of the two compounds is usually detectable in the serum of the subject at the onset of administration of the other compound.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

In order that the invention described herein may be more fully understood, the following examples are set forth.

Example 1

Phase 2 Study of Navitoclax in Combination with Ruxolitinib in Subjects with Primary or Secondary Myelofibrosis Methods This Phase 2 single-arm, multicenter, open-label study assessed the efficacy and safety of navitoclax combined with ruxolitinib in subjects with myelofibrosis (MF). Eligible subjects (≥18 years old, diagnosis of primary myelofibrosis, post-essential thrombocythemia (PET-MF), or post-polycythemia vera myelofibrosis (PPV-MF), Eastern Cooperative Oncology Group Performance Status (ECOG) 0-2, receiving at least 12 weeks of continuous ruxolitinib therapy prior to study treatment initiation) received a starting dose of 50 mg navitoclax once-daily combined with the current stable dose of ruxolitinib (≥10 mg twice a day (BID)). Weekly intra-subject dose-escalation of navitoclax was allowed based on tolerability and platelet count, first from 50 mg to 100 mg, then to 200 mg, up to a maximum daily dose of 300 mg. Treatment continued until the end of clinical benefit, unacceptable toxicity, or discontinuation. The primary efficacy endpoint was percentage reduction in splenic volume from baseline. Secondary endpoints included effect on total symptom score (TSS), overall response rate, rate of anemia response, improvement in bone marrow fibrosis, and safety profile.

Subject Inclusion Criteria

For this study, inclusion criteria included the following:
1. Subject must be ≥18 years of age.
2. Subject has documented diagnosis of Intermediate or High-Risk Primary Myelofibrosis, Post-Polycythemia Vera Myelofibrosis (PPV-MF), or Post-Essential Thrombocythemia Myelofibrosis (PET-MF) as defined by the World Health Organization classification.
3. Subject must be ineligible or unwilling to undergo stem cell transplantation at time of study entry.
4. Subject must have an Eastern Cooperative Oncology Group (ECOG) Performance Score of 0, 1, or 2.
5. Cohort 1a only: Subject must have received ruxolitinib therapy for at least 12 weeks and be currently on a stable dose of ≥10 mg BID of ruxolitinib for ≥8 weeks prior to the 1st dose of navitoclax.
6. Cohort 1b only: Subject must have received prior treatment with JAK-2 inhibitor therapy for at least 12 weeks
7. Cohort 2 only: Subject must have received prior treatment with JAK-2 inhibitor therapy and meet one of the following criteria (a or b):
   a. Prior treatment with JAK-2 inhibitor for at least 12 weeks
   b. Prior treatment with JAK-2 inhibitor for at least 28 days complicated by any of the following:
      i. Development of red blood cell transfusion requirement (at least 2 units/month for 2 months, OR
      ii. Grade ≥3 adverse events of thrombocytopenia, anemia, hematoma and/or hemorrhage while on JAK-2 inhibitor treatment
8. Cohort 3 only: Subject must not have received prior treatment with a JAK-2 inhibitor.
9. Subject has splenomegaly defined as spleen palpation measurement ≥5 cm below costal margin or spleen volume ≥450 cm³ as assessed by MRI.
10. Subject must meet the following laboratory parameters per local laboratory reference range at Screening:
    Adequate bone marrow reserves; in the absence of growth factors, thrombopoietic factors, or platelet transfusions for at least 14 days:
    Platelet count ≥100×10⁹/L (Cohorts 1a, 1b or 3)
    Platelet count ≥75×10⁹/L (Cohort 2)
    ANC ≥1×10⁹/L
    Renal function: calculated creatinine clearance ≥30 mL/minute.
    Hepatic function and enzymes:
      AST and ALT ≤3.0× the upper normal limit (ULN)
      Total Bilirubin ≤1.5×ULN (exception: subjects with Gilbert's Syndrome may have a Bilirubin >1.5× ULN)
      Coagulation: aPTT and INR <1.5×ULN Key Exclusion Criteria
1. Splenic irradiation within 6 months prior to screening, or prior splenectomy.
2. Leukemic transformation (>10% blasts in peripheral blood or bone marrow biopsy).
3. Subject is currently on medications that interfere with coagulation (including warfarin) or platelet function with the exception of low dose aspirin (up to 100 mg) and low-molecular-weight heparin (LMWH).
4. Prior therapy with a BH3 mimetic compound.
5. Subject has received strong or moderate CYP3A inhibitors (e.g., ketoconazole, clarithromycin and fluconazole) within 14 days prior to the administration of the first dose of navitoclax.

TABLE 13

Bone Marrow Grading of Myelofibrosis

| Grading | Description |
| --- | --- |
| MF-0 | Scattered linear reticulin with no intersections (cross-overs) corresponding to normal bone marrow |
| MF-1 | Loose network of reticulin with many intersections, especially in perivascular areas |
| MF-2 | Diffuse and dense increase in reticulin with extensive intersections, occasionally with only focal bundles of collagen and/or focal osteosclerosis |
| MF-3 | Diffuse and dense increase in reticulin with extensive intersections with coarse bundles of collagen, often associated with significant osteosclerosis. |

*Fiber density should be assessed in hematopoietic (cellular) areas. (Thiele J, Kvasnicka HM, Facchetti F, et al. European Consensus on Grading Bone Marrow Fibrosis and Assessment of Cellularity. Haematologica. 2005; 90(8): 1128-32.)

Results

Thirty-four subjects (primary myelofibrosis, n=16; PET-MF, n=5; PPV-MF, n=13) had received ≥1 dose of navitoclax in combination with ruxolitinib. Median age was 68 years old (range was 42 years old-86 years old), 68% were male, and 9 subjects (26%) had ≥3 prior lines of myelofibrosis therapy.

Subjects needed to have received ruxolitinib therapy for at least 12 weeks prior to study enrollment without interruption, have splenomegaly as defined by a spleen palpable ≥5 cm below costal margin and be currently on a stable dose of ≥10 mg BID of ruxolitinib. The median duration of prior ruxolitinib exposure was 745 days (range was 134-4549 days). Of the 34 subjects enrolled, 27 (79%) had JAK-2 and 7 subjects (21%) had CALR mutations. There were no subjects enrolled with triple-negative myelofibrosis. Of 33 subjects with available baseline testing, 17 (52%) had high molecular risk, defined by mutations within ASXL1, EZH2, IDH1/2, SRSF2, or U2AF1. The mean baseline platelet count was 231×10⁹/L (range was 99-706). The mean baseline hemoglobin (Hgb) was 10.8 g/dL. Nineteen (56%) subjects had elevated white blood cell count (WBC) at baseline (>1.5×ULN (upper limit of normal)).

Navitoclax was administered at a starting dose of 50 mg oral QD. Based on individual tolerability including platelet counts, the dose of navitoclax was increased weekly to a maximum dose of 300 mg QD. Of the 34 patients enrolled, maximal navitoclax dose of 300 mg was achieved in 23 subjects (68%). As shown in Table 14, 83% (19/23) of patients subsequently dose reduced navitoclax with the primary reason for dose reduction being thrombocytopenia (47.8%). Hence, an optimal dose of 200 mg navitoclax was chosen.

TABLE 14

Navitoclax Dose Reduction

| Navitoclax QD Dosing | n ᵃ (%) |
| --- | --- |
| Dose Reduction | |
| No Dose Reduction | 4 (17.4) |
| Only One Dose Reduction | 10 (43.5) |
| More Than One Dose Reduction | 9 (39.1) |

TABLE 14-continued

Navitoclax Dose Reduction

| Navitoclax QD Dosing | n [a] (%) |
|---|---|
| All Reasons for Dose Reduction | |
| Adverse Events | 17 (73.9) |
| Thrombocytopenia | 11 (47.8) |
| Diarrhea | 2 (8.7) |
| Anemia | 4 (17.4) |
| Other | 7 (30.4) |
| Logistics/Schedule/Surgery Conflicts | 0 |
| Other | 4 (17.4) |
| Dose Delay/Interruption | |
| No Interruption | 8 (34.8) |
| Only One Interruption | 6 (26.1) |
| More Than One Interruption | 9 (39.1) |
| All Reasons for Dose Delay/Interruption | |
| Adverse Events | 12 (52.2) |
| Thrombocytopenia | 8 (34.8) |
| Diarrhea | 1 (4.3) |
| Anemia | 1 (4.3) |
| Other | 4 (17.4) |
| Logistics/Schedule/Surgery Conflicts | 0 |
| Other | 7 (30.4) |

[a] n = number of subjects

Of the 25 (74%) subjects that enrolled on ruxolitinib doses >10 mg BID, 22 (88%) subsequently had the dose of ruxolitinib reduced to 10 mg BID. At the time of this analysis, 24 subjects were evaluable for efficacy, with 20 subjects completing ≥24 weeks on study and 4 subjects with treatment discontinuations prior to 24 weeks. FIG. 1 shows a waterfall plot of spleen volume change from baseline at week 24.

Efficacy data are shown in Table 15. At week 24 of treatment with the combination of navitoclax and ruxolitinib, 7 of 24 subjects (29%) achieved a spleen volume reduction of ≥35% ($SVR_{35}$) from baseline by MRI (magnetic resonance imaging) as determined by prespecified central review and 54% of subjects achieved >50% reduction of the spleen length (cm, below costal margin) as assessed by palpation. Additionally, spleen responses deepened beyond 24 weeks of treatment and the best overall $SVR_{35}$ at any time on study was achieved in 10 subjects (42%), with 79% of subjects achieving reductions in spleen length by palpation of >50%. Reductions in driver mutation allelic burden of >5% were observed in 10 subjects (42%); 6 subjects (25%) had bone marrow fibrosis (BMF) improvement of ≥1 grade, suggesting that the combination of navitoclax and ruxolitinib is disease modifying.

TABLE 15

Best Response Rates in Efficacy Evaluable Population

| Navitoclax QD + Ruxolitinib BID ($N^a$ = 24)[b] | $N^a$ (%) |
|---|---|
| $SVR_{35}$[c] at week 24 | 7 (29) |
| $SVR_{35}$[c] Best On-Study | 10 (42) |
| Reduction in Bone Marrow Fibrosis of ≥1 Grade | 6 (25) |
| Reduction >5% from Baseline in Allelic Frequency | 10 (42) |

[a] N = number of subjects
[b] Four subjects discontinued treatment prior to Week 24, considered non-responders for analysis purpose
[c] $SVR_{35}$ = spleen volume reduction of 35%

Of the 13 subjects with total symptom score (TSS) data available at baseline and Week 24, 54% of subjects report a reduction in TSS with 3 patients (23%) achieving ≥50% TSS reduction from baseline with the addition of navitoclax. The median TSS at week 24 was 7.4 (range: 0-23), a 20.4% improvement from baseline. All patients (N=34) receiving navitoclax and ruxolitinib combination therapy experienced at least 1 treatment-emergent adverse event (TEAE). The most common (≥20%) were thrombocytopenia (82%), diarrhea (62%), fatigue (53%), anemia (27%), nausea (27%), contusion (24%), and vomiting (21%). TEAE Grade ≥3 TEAEs occurred in 26 subjects (77%); most common were thrombocytopenia (n=15, 44%; Grade 4 n=1, 3%) and anemia (n=8, 24%; no Grade 4). Five subjects (15%) experienced serious adverse events that resolved including anemia, upper abdominal pain, vomiting, chest pain, increased C-reactive protein, and abnormal liver function test (3% each). One subject (4%) had an anemia response; the mean Hgb at week 24 was slightly improved over baseline at 11.3 g/dL. Of the 19 subjects with elevated baseline white blood cell count, 16 (84%) reduced to within normal limits during treatment, with a median white blood cell count (WBC) reduction of $17.7 \times 10^9$/L. Notably, there were no significant episodes of bleeding and no TEAE-related deaths.

The Phase 2 clinical data demonstrate, for the first time in human patients, that the combination therapy of navitoclax and ruxolitinib, particularly for patients who are refractory to ruxolitinib monotherapy, led to a clinically meaningful reduction in spleen volume, allelic burden reductions, Total Symptom Score improvements and, importantly, encouraging improvements in bone marrow fibrosis (BMF) in subjects with myelofibrosis who have received prior treatment with ruxolitinib, with a manageable safety profile. Weekly navitoclax dose escalation from 50 mg once daily to 300 mg once daily in combination with ruxolitinib at ≥10 mg, was generally safe without clinically relevant thrombocytopenia-related bleeding. In addition, 83% of subjects experienced a dose reduction of navitoclax during study treatment with the primary reason being thrombocytopenia. Of the subjects with navitoclax dose reductions for thrombocytopenia, 60% received 300 mg of navitoclax. Therefore, doses of navitoclax <300 mg once daily seem to be better tolerated in patients with myelofibrosis.

Example 2

Figure 2:
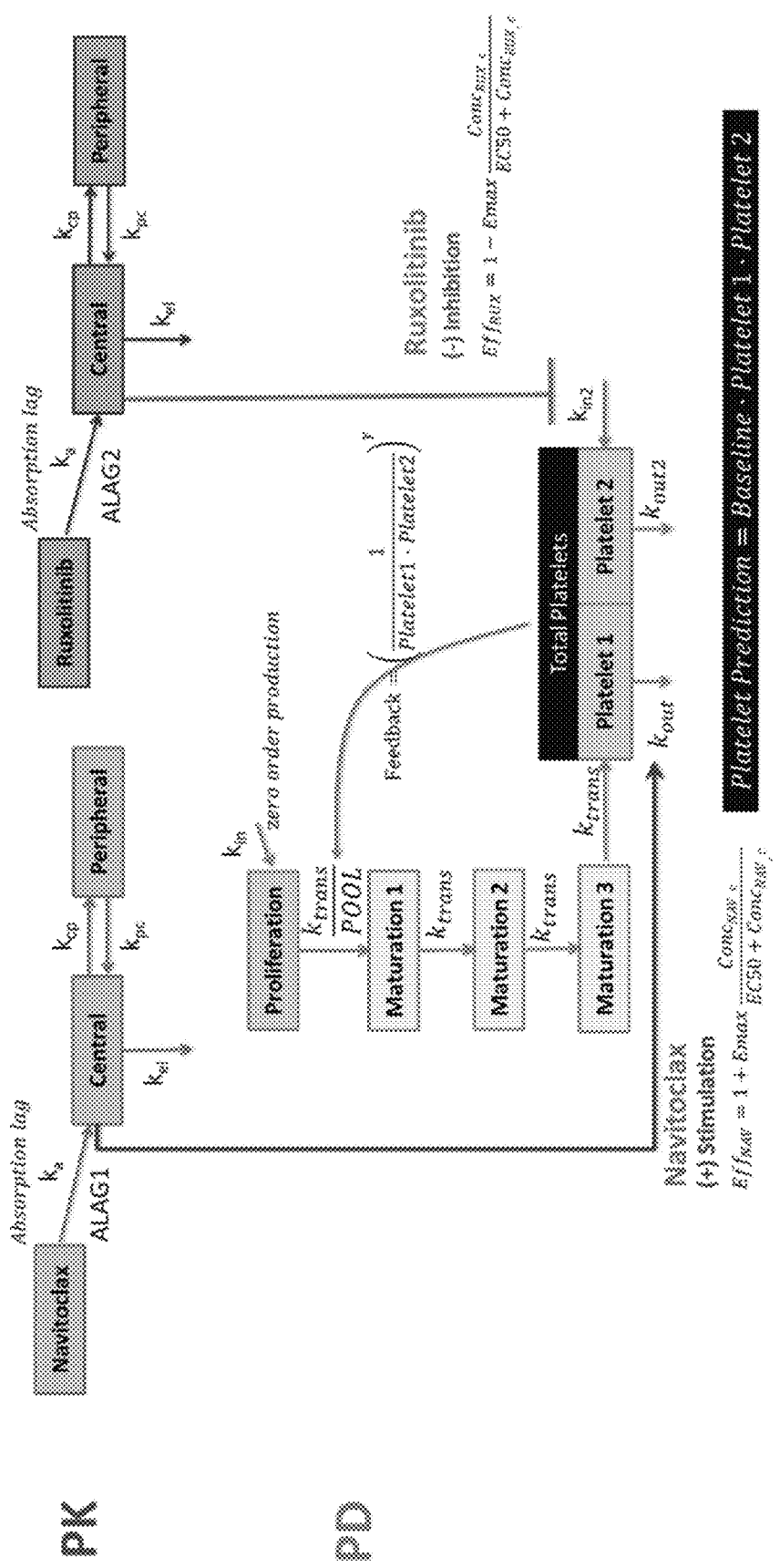
FIG. 2 is a schematic of the exposure-response model for platelet inhibition by combination of navitoclax and ruxolitinib described in Example 2.

Dose Selection of Navitoclax and Ruxolitinib in Phase 3 Studies in Subjects with Myelofibrosis Selection of Navitoclax Dose using Exposure-Platelet Response Modeling
Exposure-Platelet Response Model A mechanistic model evaluating the effect of navitoclax and ruxolitinib on platelets counts was developed to guide navitoclax dose selection in Phase 3 studies (Examples 4 and 5 supra) in combination with ruxolitinib in MF. The model was based on established models described in the literature (Kaefer, A., Yang, J., Noertersheuser, P. et al. Cancer Chemother Pharmacol (2014) 74: 593. doi:10.1007/s00280-014-2530-2530; and Friberg, Lena E., et al. "Model of chemotherapy-induced myelosuppression with parameter consistency across drugs. "*Journal of clinical oncology* 20.24 (2002): 4713-4721, both references hereby incorporated by reference in their entireties). The model was also used to perform simulations of the add-on effects of navitoclax at stable ruxolitinib dose. FIG. 2 shows the model scheme utilized wherein Ka is first-order absorption rate constant,
ALAG1 is absorption lag time of navitoclax,
ALAG2 is absorption lag time of ruxolitinib,
kel is first order elimination rate constant,
kcp and kpc are first-order intercompartmental rate constants between central and peripheral PK compartments,
Proliferation is progenitor cell compartment,
Maturation 1, Maturation 2, and Maturation 3 are transit compartments representing maturation of the progenitor cells,
Platelet 1+Platelet 2 are circulating platelets relative to baseline,
$k_{in}$ and $k_{in2}$ are zero-order platelet proliferation rate constants,
$k_{trans}$ is rate constant describing the transfer between the different transit compartments,
$k_{out}$ is rate constant describing loss of the circulating cells in blood,
γ is power term on the feedback mechanism,
POOL is initial size of the progenitor cell compartment,
$Eff_{NAV}$ and $Eff_{RUX}$ are effect of navitoclax and ruxolitinib, respectively on platelets,
$EC50_{NAV}$ and $EC50_{RUX}$, are navitoclax and ruxolitinib concentrations, respectively at which half-maximal drug effect is obtained,
$Emax_{NAV}$ and $Emax_{RUX}$ are maximum effect of navitoclax and ruxolitinib, respectively on platelets, and
$Conc_{NAV,c}$ and $Conc_{RUX,c}$ are navitoclax and ruxolitinib concentration in the central plasma compartment, respectively.

The mechanistic model was fitted in NONMEM® (Version 7.4.3, 3) to individual concentration (navitoclax and ruxolitinib) and platelet response data from 34 subjects receiving oral navitoclax starting at 50 mg QD with stepwise weekly dose escalation to 100 mg QD, 200 mg QD and 300 mg QD and ruxolitinib at ≥10 mg BID (Data from Example 1 infra).

The navitoclax pharmacokinetic (PK) model was a two-compartmental model with a lag-time in absorption (Equations 1a through 1c). PK model for ruxolitinib was described by a two-compartment model with a lag-time in absorption (Equations 2a through 2c).

Subsequently, the relationship between navitoclax and ruxolitinib exposure and longitudinal platelet response was analyzed. The time course of platelet response was modeled using a semi-physiological model that comprised a progenitor cell compartment, three transition compartments representing the maturation chain in the bone marrow and a peripheral blood compartment (see FIG. 2). A feedback system was used in this model to describe the increase in the maturation rate in bone marrow when the platelet level in the blood compartment is below baseline and decrease in the maturation rate when the platelet level in blood is above baseline. The model also included a progenitor cell "POOL" which describes a large pool of platelet progenitor cells at the beginning of navitoclax and ruxolitinib treatment. Navitoclax effect was modeled to increase the elimination of the circulating platelets (increasing elimination of platelets). Due to insufficient data to estimate ruxolitinib effect and observed difference in the effect of ruxolitinib on platelets compared to navitoclax (owing to longer exposure to ruxolitinib prior to navitoclax introduction), ruxolitinib effect on platelets was described based on an available model (4) and was assumed to inhibit proliferation of platelets. The drug effect was incorporated as an $E_{max}$-$EC_{50}$ inhibitory model based on navitoclax and ruxolitinib concentrations. Equations 3 to 9 represent the PD model.

Navitoclax PK Model $$\frac{dGut}{dt} = -k_a \times Gut \quad \text{Equation 1a}$$

$$\frac{dConc_{NAV,c}}{dt} \times V_c = k_a \times Gut - k_{el} \times Conc_{NAV,c} \times V_{NAV,c} - k_{cp} \times Conc_{NAV,c} \times V_{NAV,c} + k_{pc} \times Conc_{NAV,p} \times V_{NAV,p} \quad \text{Equation 1b}$$

$$\frac{dConc_{NAV,p}}{dt} \times V_p = k_{cp} \times Conc_{NAV,c} \times V_{NAV,c} - k_{pc} \times Conc_{NAV,p} \times V_{NAV,p} \quad \text{Equation 1c}$$

Ruxolitinib PK Model $$\frac{dGut}{dt} = -k_a \times Gut \quad \text{Equation 2a}$$

$$\frac{dConc_{RUX,c}}{dt} \times V_c = k_a \times Gut - k_{el} \times Conc_{RUX,c} \times V_{RUX,c} - k_{cp} \times Conc_{RUX,c} \times V_{RUX,c} + k_{pc} \times Conc_{RUX,p} \times V_{RUX,p} \quad \text{Equation 2b}$$

$$\frac{dConc_{RUX,p}}{dt} \times V_p = k_{cp} \times Conc_{RUX,c} \times V_{RUX,c} - k_{pc} \times Conc_{RUX,p} \times V_{RUX,p} \quad \text{Equation 2c}$$

Pharmacodynamic (PD) Model $$\text{Feedback} = k_{in} - \frac{k_{trans}}{POOL} \times \left(\frac{1}{PLT1 + PLT2}\right)^\gamma \quad \text{Equation 3}$$

$$\frac{dPROLIF}{dt} = k_{in} - \frac{k_{trans}}{POOL} \times PROLIF \times \text{Feedback} \quad \text{Equation 4}$$

$$\frac{dMAT1}{dt} = \frac{k_{trans}}{POOL} \times PROLIF \times \text{Feedback} - k_{trans} \times MAT1 \quad \text{Equation 5}$$

$$\frac{dMAT2}{dt} = k_{trans} \times MAT1 - k_{trans} \times MAT2 \quad \text{Equation 6}$$

$$\frac{dMAT3}{dt} = k_{trans} \times MAT2 - k_{trans} \times MAT3 \quad \text{Equation 7}$$

$$\frac{dPLT1}{dt} = k_{trans} \times MAT3 - k_{out} \times PLT1 \times \left(1 + \frac{Emax_{NAV} \times Conc_{NAV,c}}{EC50_{NAV} + Conc_{NAV,c}}\right) \quad \text{Equation 8}$$

$$\frac{dPLT2}{dt} = k_{in2} \times PLT2 \times \left(1 - \frac{Emax_{RUX} \times Conc_{RUX,c}}{EC50_{RUX} + Conc_{RUX,c}}\right) - k_{out2} \times PLT2 \quad \text{Equation 9}$$

In the PK model, the term(s)

"Gut" is the amount of navitoclax or ruxolitinib remaining to be absorbed from the gut "$k_a$" represents a first-order absorption rate constant "$Conc_{NAV,c}$" and "$Conc_{RUX,c}$" represent navitoclax and ruxolitinib concentration in the central plasma compartment, respectively, "$Conc_{NAV,p}$" and "$Conc_{RUX,p}$" represent navitoclax and ruxolitinib concentration in the peripheral compartment, respectively, "$V_{NAV,c}$" and "$V_{RUX,c}$" represent navitoclax and ruxolitinib central volumes of distribution, respectively, "$V_{NAV,p}$" and "$V_{RUX,p}$" represent navitoclax and ruxolitinib peripheral volumes of distribution, respectively, "$k_{cp}$" and "$k_{pc}$" represent first-order intercompartmental rate constants between central and peripheral PK compartments, and "$k_{el}$" represents a first-order elimination rate constant.

In the pharmacodynamic (PD) model, the term(s)

"PROLIF" represents the progenitor cell compartment that undergoes active proliferation, "MAT1", "MAT2", "MAT3" are the transit compartments representing maturation of the progenitor cells, "PLT1" and "PLT2" together represent circulating platelets relative to baseline, "$k_{in}$" and "$k_{in2}$" represent zero-order platelet proliferation rate constant, "$k_{trans}$" is the rate constant describing the transfer between the different transit compartments, "$k_{out}$" is the rate constant describing loss of the circulating cells in blood, "$\gamma$" is the power term on the feedback mechanism, "POOL" represents the initial size of the progenitor cell compartment, "$EC50_{NAV}$" and "$EC50_{RUX}$" represent the navitoclax and ruxolitinib concentrations, respectively at which half-maximal drug effect is obtained, and $Emax_{NAV}$ and $Emax_{RUX}$ represent the maximum effect of navitoclax and ruxolitinib, respectively on platelets.

The model is initialized at 0 for the PK related compartments, at POOL for the PROLIF compartment, and at 1 for the maturation and circulation compartments. The platelet prediction is obtained by (Baseline Platelets)×PLT1×PLT2. The rates of the Platelet1 model are set to be the same $k_{trans}=k_{in}=k_{out}$ due to a steady state assumption without treatment interference.

Some of the parameters were fixed to values published in the literature. $k_{out}$ was fixed to 0.521 l/day, $\gamma$ was fixed to 0.667, $E_{max}$ of navitoclax was fixed to 5 based on Kaefer et al. (Kaefer, A., Yang, J., Noertersheuser, P. et al. Cancer Chemother Pharmacol (2014) 74: 593. doi:10.1007/s00280-014-2530-2530), hereby incorporated by reference in its entirety. EC50 values of ruxolitinib was fixed to published value of 0.08248 mg/L, $k_{out2}$ was fixed to 0.0312 l/day and $E_{max}$ value of ruxolitinib was assumed to be 1 (US Drug Approval Package for JAKAFI® (ruxolitinib) Tablets. CLINICAL PHARMACOLOGY AND BIOPHARMACEUTICS REVIEW(S); APPLICATION NUMBER: 202192Orig1s000), hereby incorporated by reference in its entirety.

To account for the ruxolitinib experienced nature of subjects, platelets at the initiation of Navitoclax (baseline) were assumed to be ruxolitinib treatment challenged. A factor was included on the baseline platelet count such that baseline($t$=−84 days)=factor×baseline($t$=0 days)

where t=0 is the time of initiation of navitoclax. This yields a relative pseudo baseline at initiation of ruxolitinib (referred to as 'ruxolitinib factor' on baseline platelet count). Thus, the model was run for 84 days before the start of navitoclax (with ruxolitinib administered in monotherapy) to account for ruxolitinib effect in the 12 weeks prior to administration of navitoclax. However, data before initiation of navitoclax was not fitted due to incomplete history of individual ruxolitinib treatment before start of the study. The first 56 days of data were fitted to avoid influence of long-term disease effects on the model.

EC50 for navitoclax, the POOL size and the ruxolitinib factor for pseudo baseline were the only parameters that were estimated. Inter-individual variability was incorporated on navitoclax EC50 and the residual variability was characterized using combined proportional and additive error model. No inter-individual variability was estimated on ruxolitinib EC50 since limited data precluded its appropriate estimation.

Results

The estimated model parameters are listed in Table 16. All parameters were estimated with good precision.

As the observed baseline at initiation is assumed to be lower than at the initiation of ruxolitinib, a factor was estimated that yields the relative pseudo baseline at initiation of ruxolitinib. This factor was estimated to be 1.53-fold, thus, ruxolitinib was estimated to cause a ~36% drop in platelet count (from 1.53 to 1) at average ruxolitinib concentration. This estimate is aligned with the observed decline published in the US FDA clinical pharmacology review of ruxolitinib (Drug Approval Package for JAKAFI® (ruxolitinib) Tablets. CLINICAL PHARMACOLOGY AND BIOPHARMACEUTICS REVIEW(S); APPLICATION NUMBER: 202192Orig1s000) and by Verstovsek et al (Verstovsek S, Gotlib J, Gupta V, Atallah E, Mascarenhas J, Quintas-Cardama A, Sun W, Sarlis N J, Sandor V, Levy R S, Kantarjian H M, Mesa R A. Management of cytopenias in patients with myelofibrosis treated with ruxolitinib and effect of dose modifications on efficacy outcomes. Onco Targets Ther. 2013 Dec. 17; 7:13-21. doi: 10.2147/OTT.S53348. PMID: 24368888; PMCID: PMC3869911), all references hereby incorporated by reference in their entireties.

TABLE 16

Parameter Estimates of the Exposure-Platelet Response Model for the Combination of Navitoclax and Ruxolitinib

| Parameter | Estimate and 95% Confidence Interval | Inter individual variablity (OMEGA) |
|---|---|---|
| $k_{out}$ (1/day) | 0.521 fixed | |
| Gamma | 0.667 fixed | |
| POOL size | 15.8 (8.12; 31.0) | |
| BaselineFactor | 1.53 (1.41; 1.65) | |
| Navitoclax $EC_{50}$ (mg/L) | 3.61 (1.97; 6.58) | 1.03 (134% CV) |
| Navitoclax $E_{max}$ | 5 fixed | |
| $k_{out2}$ (1/day) | 0.0312 fixed | |
| Ruxolitinib $EC_{50}$ (mg/L) | 0.0825 fixed | |
| Ruxolitinib $E_{max}$ | 1 fixed | |

Simulations

Platelet count simulations were conducted considering two dosing regimens corresponding to R/R MF population and naive MF (no prior treatment for MF) population enrolling 100 subjects for each scenario. Within each of these scenarios, simulations were conducted at different navitoclax doses in combination with 10 mg BID ruxolitinib:

R/R MF subjects: In R/R MF subjects currently on ruxolitinib treatment of 10 mg BID, different doses navitoclax were simulated as follows:

Flat starting doses of navitoclax (100 mg QD, 200 mg QD, 300 mg QD)

Starting navitoclax at 100 mg QD with a weekly ramp-up to 200 mg QD.

Naive MF: In naive MF subjects, different doses navitoclax in combination with 10 mg BID ruxolitinib were simulated as follows:

Flat starting doses of navitoclax (100 mg QD, 200 mg QD, 300 mg QD)

Starting navitoclax at 100 mg QD with a weekly ramp-up to 200 mg QD.

The impact of adaptive dosing was explored using a regimen with platelet count dependent dose escalation from 100 mg QD to 200 mg QD navitoclax after two weeks of treatment (only if platelet count >=100×10$^9$ cells/L).

100 subjects were simulated for each regimen and scenario. 250 replicates of the simulations were run and summarized. Overall, 12 weeks of various navitoclax daily doses plus continuous 10 mg BID treatment of ruxolitinib were administered. Continuous dosing of navitoclax and ruxolitinib without any dose reductions or interruptions was assumed.

All simulations were conducted using the model estimated for 34 subjects from Example 1. For the simulation, the inter individual variability for ruxolitinib EC50 was assumed to be 98.2% based on the available model (4). Only subjects with a platelet count between 100 and 500 at the initiation of navitoclax were allowed in the simulation. For R/R the observed baseline from Example 1 was used (~200× 10$^9$ cells/L), with CV of 51%) and adjusted with the estimated baseline factor. The R/R population was treated with ruxolitinib for 12 weeks before administration of the first navitoclax dose. For the naïve population, the baseline factor was not used, but a slightly higher baseline based on the available model was used (276×10$^9$ cells/L, CV of 57%) (Drug Approval Package for JAKAFI® (ruxolitinib) Tablets. CLINICAL PHARMACOLOGY AND BIOPHARMACEUTICS REVIEW(S); APPLICATION NUMBER: 202192Orig1s000), hereby incorporated by reference in its entirety. Baseline platelet count was assumed to be lognormally distributed.

Mean percent subjects with Grade 3/4 thrombocytopenia were calculated using all replicates. Based on these percentages, confidence intervals were derived using a binomial distribution assumption. Table 17 shows the allocation of subjects to baseline groups was used (resulting from the baseline distribution as defined above).

TABLE 17

Allocation of Subjects to Different Baseline Groups in the Simulations

| Baseline group (×10$^9$ cells/L) | Naive MF | R/RMF |
|---|---|---|
| 100-150 | 22 | 12 |
| 150-300 | 59 | 52 |
| 300-500 | 19 | 36 |
| Total | 100 | 100 |

Simulation Results

Figure 3A:
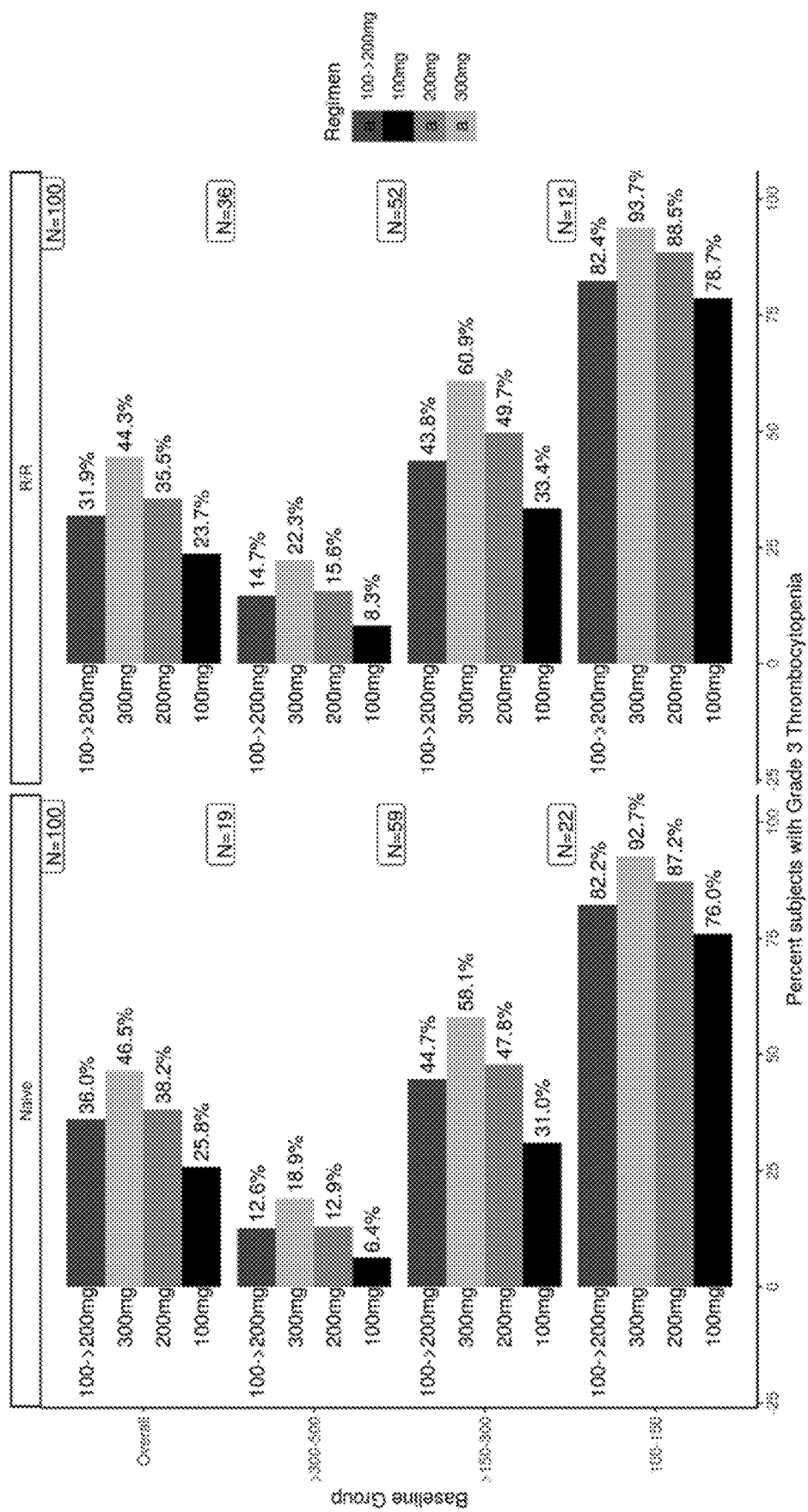
FIGS. 3A, 3B shows the predicted percent incidence of grade 3 (FIG. 3A) and grade 4 (FIG. 3B) thrombocytopenia for combination of navitoclax and ruxolitinib (10 mg twice a day (BID)) in naive myelofibrosis and relapsed or refractory myelofibrosis as described in Example 2.
Figure 3B:
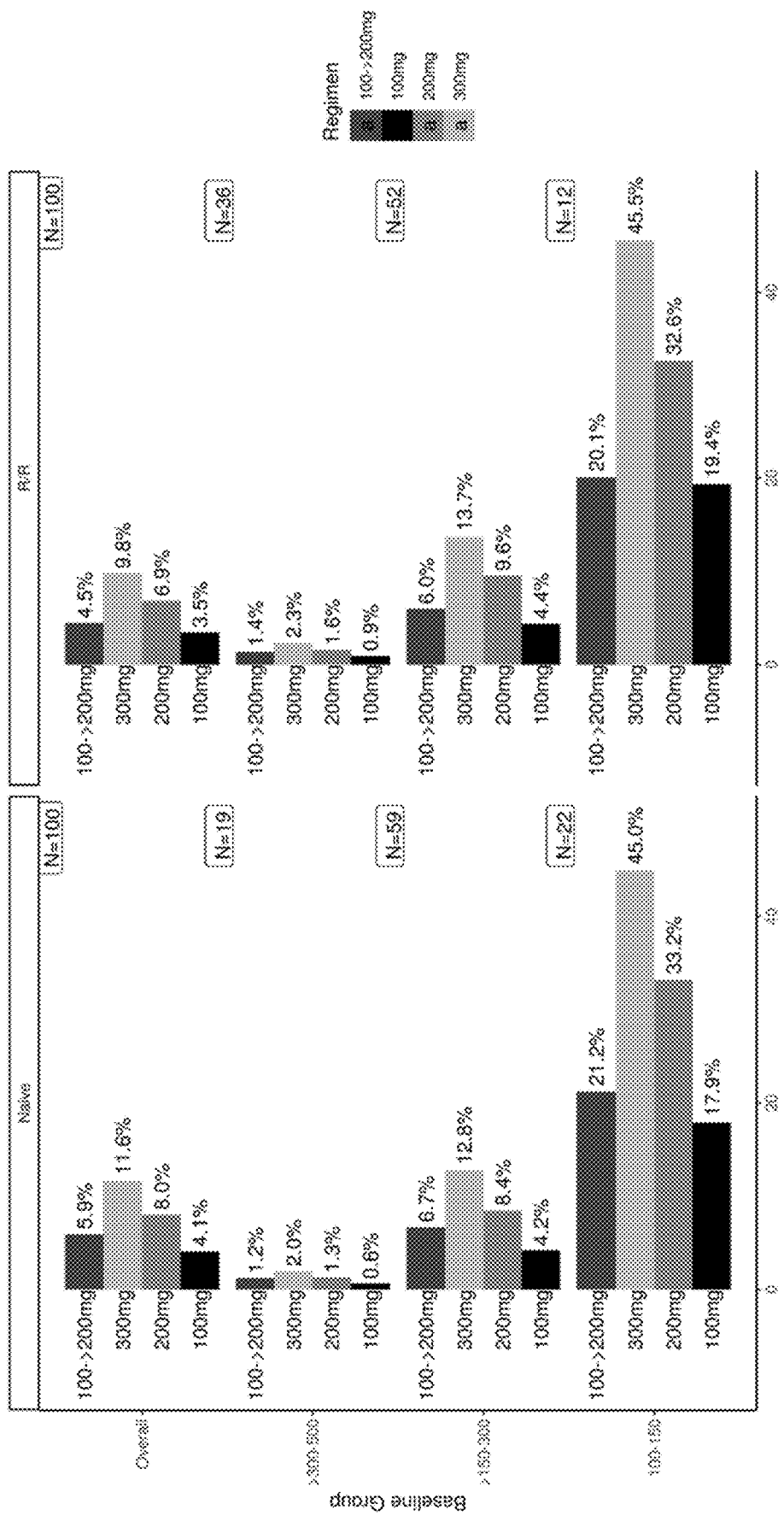

Based on the simulations, maximum decreases in platelets and incidences of Grade 3/4 thrombocytopenia during weekly ramp-up from 100 mg to 200 mg QD were either similar to or slightly lower than those predicted at a flat starting dose of 200 mg (<6% difference for baseline platelet >150×10$^9$/L and ≤150×10$^9$/L) in both R/R and Naive MF (FIG. 3, Table 18).

TABLE 18

Simulated Mean (90% CI) Percent Changes from Baseline, Percent Incidence of Grade 3/4 Thrombocytopenia for Combination of Navitoclax and Ruxolitinib (10 mg BID) in Naïve MF and R/R MF

| Cohort | Baseline Platelet Count (×10$^9$ Cells/L) | Regimen | Grade 3 | Grade 4 |
|---|---|---|---|---|
| Naive MF | 100-150 | 100 mg | 76.0% (59.1; 90.9) | 17.9% (4.5; 31.8) |
| | 100-150 | 200 mg | 87.2% (72.7; 95.5) | 33.2% (18.2; 50.0) |
| | 100-150 | 300 mg | 92.7% (81.8; 100.0) | 45.0% (27.3; 63.6) |
| | 100-150 | 100−>200 mg | 82.2% (68.2; 95.5) | 21.2% (9.1; 36.4) |
| | >150-300 | 100 mg | 31.0% (22.0; 40.7) | 4.2% (0.0; 8.5) |
| | >150-300 | 200 mg | 47.8% (37.3; 57.6) | 8.4% (3.4; 15.3) |
| | >150-300 | 300 mg | 58.1% (47.5; 67.8) | 12.8% (6.8; 20.3) |
| | >150-300 | 100−>200 mg | 44.7% (33.9; 55.9) | 6.7% (1.7; 11.9) |
| | >300-500 | 100 mg | 6.4% (0.0; 15.8) | 0.6% (0.0; 5.3) |
| | >300-500 | 200 mg | 12.9% (0.0; 26.3) | 1.3% (0.0; 5.3) |
| | >300-500 | 300 mg | 18.9% (5.3; 36.8) | 2.0% (0.0; 10.5) |
| | >300-500 | 100−>200 mg | 12.6% (0.0; 26.3) | 1.2% (0.0; 5.3) |
| R/R MF | 100-150 | 100 mg | 78.7% (58.3; 100.0) | 19.4% (0.0; 41.7) |
| | 100-150 | 200 mg | 88.5% (75.0; 100.0) | 32.6% (8.3; 58.3) |
| | 100-150 | 300 mg | 93.7% (83.3; 100.0) | 45.5% (25.0; 66.7) |
| | 100-150 | 100−>200 mg | 82.4% (66.7; 100.0) | 20.1% (0.0; 41.7) |
| | >150-300 | 100 mg | 33.4% (23.1; 44.2) | 4.4% (0.0; 9.6) |
| | >150-300 | 200 mg | 49.7% (38.5; 61.5) | 9.6% (3.8; 17.3) |
| | >150-300 | 300 mg | 60.9% (50.0; 71.2) | 13.7% (5.8; 21.2) |
| | >150-300 | 100−>200 mg | 43.8% (32.7; 55.8) | 6.0% (1.9; 11.5) |
| | >300-500 | 100 mg | 8.3% (2.8; 16.7) | 0.9% (0.0; 2.8) |
| | >300-500 | 200 mg | 15.6% (5.6; 25.0) | 1.6% (0.0; 5.6) |
| | >300-500 | 300 mg | 22.3% (11.1; 33.3) | 2.3% (0.0; 8.3) |
| | >300-500 | 100−>200 mg | 14.7% (5.6; 25.0) | 1.4% (0.0; 5.6) |

Using this model-based approach, a flat starting dose of navitoclax was proposed at 200 mg QD in subjects with baseline platelet >150×10$^9$/L and a conservative dose of 100 mg QD in subjects with baseline platelet ≤150×10$^9$/L to minimize the risk of clinically relevant thrombocytopenia in combination with ruxolitinib.

Selection of Ruxolitinib Dose in R/R MF using Exposure-Spleen Volume Response Modeling Example 1 allowed subjects who were on stable ruxolitinib dose of ≥10 mg BID for at least 8 weeks. Ruxolitinib dose reductions have occurred in 22 of the 25 subjects that began study on doses >10 mg twice daily primarily due to thrombocytopenia (86.4%) and anemia (18.2%). By 12 weeks, the average daily dose of ruxolitinib was around 10 mg BID. Exposure-spleen volume response analysis was conducted to evaluate if >10 mg BID ruxolitinib would be more efficacious in combination with navitoclax in R/R MF subjects.

Exposure-Spleen Volume Response Model

Figure 4:
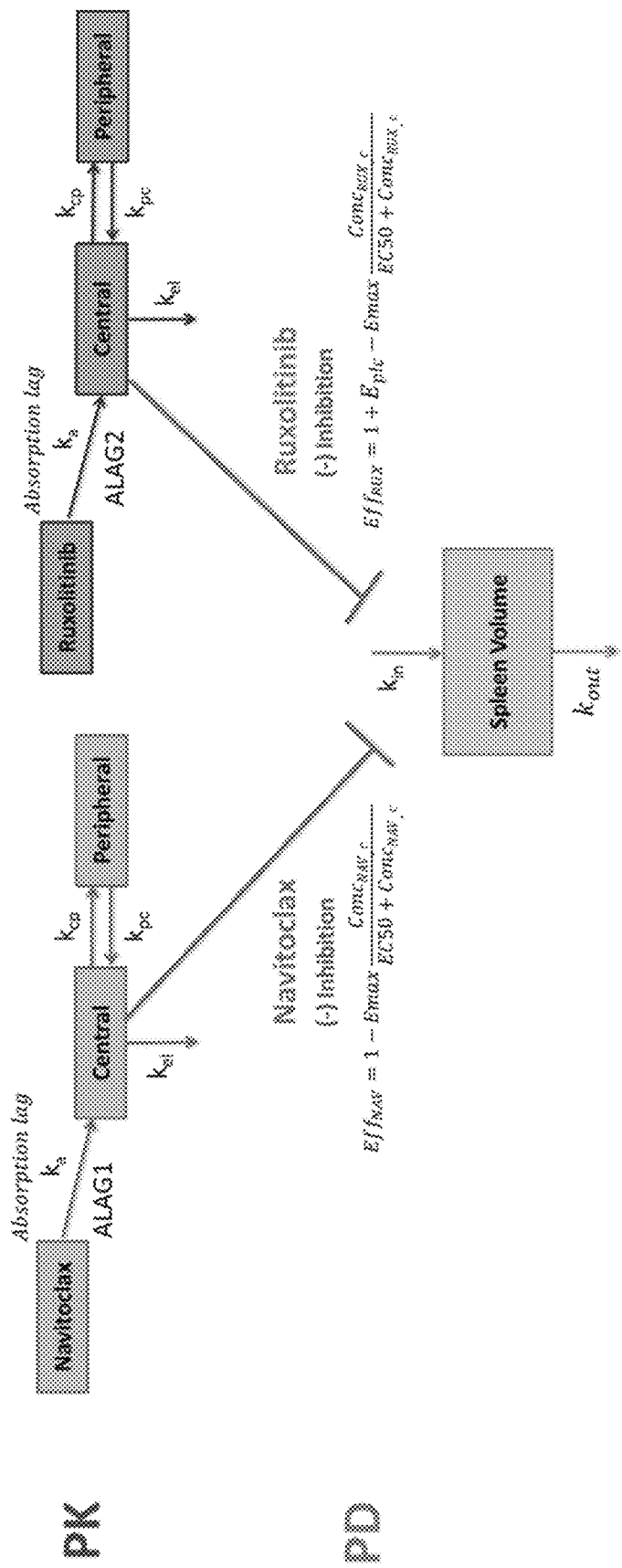
FIG. 4 is a schematic of the exposure—response model for spleen volume inhibition by combination of navitoclax and ruxolitinib as described in Example 2.

The effect of navitoclax and ruxolitinib on spleen volume was evaluated using data from cohort 1a of Example 1 in patients with relapsed/refractory MF. An indirect response model incorporating inhibitory effects of both navitoclax and ruxolitinib on spleen volume best described the data from Example 1. The model was also used to perform simulations of combination of navitoclax and ruxolitinib at different dose levels. FIG. 4 shows the model scheme.

The PK/PD model was fitted in NONMEM® (Version 7.4.3, 3) to individual concentration (navitoclax and ruxolitinib) and spleen volume data from 34 subjects receiving oral navitoclax starting at 50 mg QD with step-wise weekly dose escalation to 100 mg QD, 200 mg QD and 300 mg QD and ruxolitinib at ≥10 mg BID (data from Example 1).

The navitoclax and ruxolitinib PK models were already described above (Equations 1a through 2c). The relationship between navitoclax and ruxolitinib exposure and longitudinal spleen volume was analyzed. The time course of spleen volume was modeled using an indirect response model represented by a single spleen compartment linked to navitoclax and ruxolitinib central compartments with inhibitory effects of navitoclax and ruxolitinib on spleen volume (see FIG. 3 and Equation 10). The drug effect was incorporated as an $E_{max}$-$EC_{50}$ model based on navitoclax and ruxolitinib concentrations.

PD Model $$\frac{dSV}{dt} = k_{in} \times \left(1 - \frac{Emax_{NAV} \times Conc_{NAV,c}}{EC50_{NAV} + Conc_{NAV,c}}\right) \times \left(1 + E_{plc} - \frac{Emax_{RUX} \times Conc_{RUX,c}}{EC50_{RUX} + Conc_{RUX,c}}\right) - k_{out} \times SV \quad \text{Equation 10}$$

where the term "SV" represents the spleen volume,

"$k_{in}$" represents zero-order spleen growth rate constant,

"$k_{out}$" represents first-order spleen volume loss rate constant,

"$E_{prog}$" is the disease progression effect introduced on "$k_{in}$",

"$EC50_{NAV}$" and "$EC50_{RUX}$" represent the navitoclax and ruxolitinib concentrations, respectively at which half-maximal drug effect is obtained, and $Emax_{NAV}$ and $Emax_{RUX}$ represent the maximum effect of navitoclax and ruxolitinib, respectively on spleen volume.

Spleen volume data up to only week 40 was used in the model to improve model predictability. Emax of Navitoclax was fixed to 1 while Emax of ruxolitinib was fixed to a published value of 0.765 (4). Inter-individual variability with full correlation matrix was incorporated on estimated baseline spleen volume, $k_{out}$, $EC50_{NAV}$ and $EC50_{RUX}$ using exponential function and the residual variability was characterized using combined proportional and additive error model.

At baseline, the rates of the spleen volume model are set to be the same $k_{in}=k_{out}$ due to a theoretical steady state assumption without treatment interference. This leads to an initial condition for the SV compartment of 1, where SV predictions are derived by multiplying this compartment with baseline. Disease progression was included in the model with the factor "$E_{prog}$" on "$k_{in}$".

Results

The estimated model parameters are listed in Table 19. Due to the large % CV of the model estimates, a full covariance matrix was used during the modeling to account for correlations in the variability and thus reducing the overall variability. The shrinkage (statistical measure for overestimation of variability) of the inter-individual variability was acceptably low with a range of 12% to 39%.

TABLE 19

Parameter Estimates of the Spleen Volume Inhibition Model for Navitoclax and Ruxolitinib Combination

| Parameter | Estimate | 95% Confidence Interval | Inter-individual Variability |
|---|---|---|---|
| $k_{in}$, $k_{out}$ (1/day) | 0.000222 | 0.0000533, 0.000924 | 3.54 (579% CV) |
| $E_{prog}$ (cm³/day) | 0.0594 | 0.00394, 0.897 | 5.75 (1700% CV) |
| Navitoclax $EC_{50}$ (mg/L) | 4.37 | 0.114, 167.2 | 2.89 (412% CV) |
| Navitoclax $E_{max}$ | 1 fixed | | |
| Ruxolitinib $EC_{50}$ (mg/L) | 0.0144 | 0.00047, 1.08550 | 1.20 (152% CV) |
| Ruxolitinib $E_{max}$ | 0.765 fixed | | |

Simulations

Simulations were conducted at different doses of navitoclax at 100 mg QD, 200 mg QD and 300 mg QD in combination with different doses of ruxolitinib at 10 mg BID, 15 mg BID, and 20 mg BID. 5000 subjects/dose group were simulated. Key assumptions or the simulations included continuous dosing scenarios without any dose reductions or interruptions and baseline spleen volume (median 1.63) with interindividual variability (68.7% CV) was estimated from observed data (limited to 0.35-5.5 cm³).

Simulation Results

Figure 5:
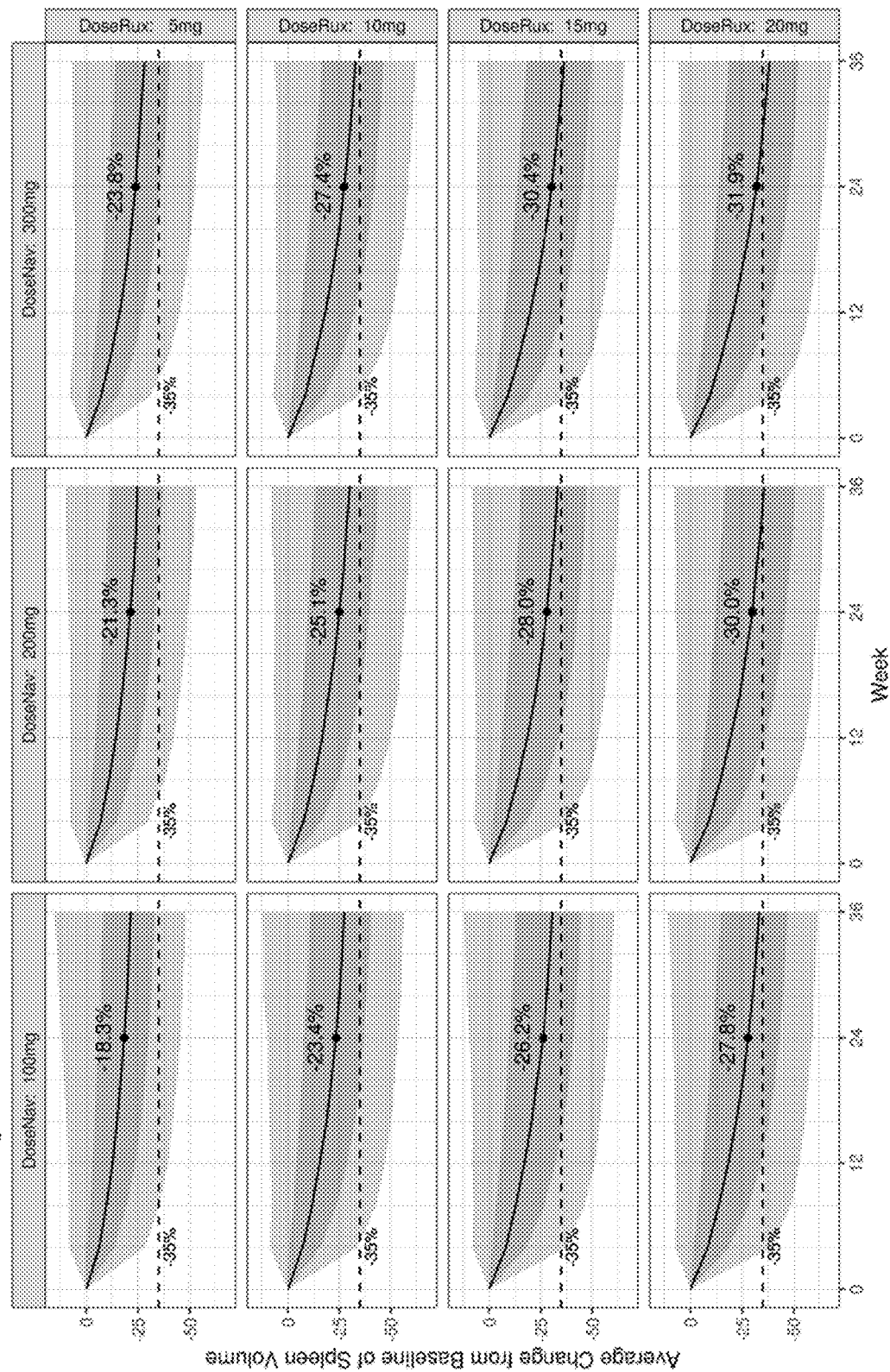
FIG. 5 shows the predicted average change from baseline of spleen volume over time for different dose combinations of navitoclax and ruxolitinib described in Example 2.

Simulations suggested moderate dose dependent decrease in percent change from baseline spleen volume for both navitoclax and ruxolitinib (FIG. 5).

Figure 6:
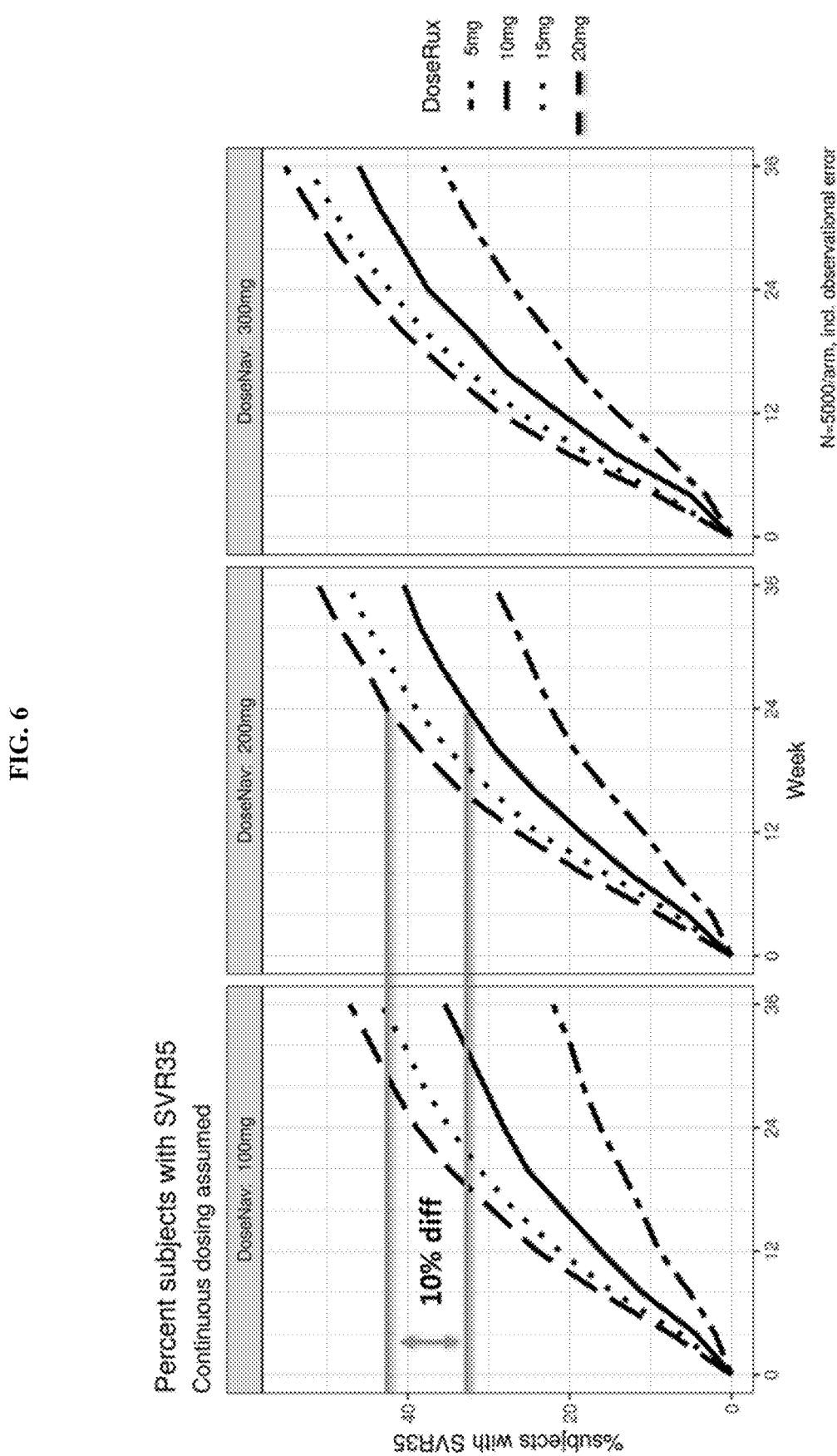
FIG. 6 shows the predicted percent of subjects with spleen volume reduction of at least 35% ($SVR_{35}$) over time for different dose combinations of navitoclax and ruxolitinib.

Percent of subjects with at least 35% of reduction in spleen volume (referred to as SVR35) at week 24, which is the primary end point of the study, was also simulated. Predicted SVR35 at week 24 was 33% which was consistent with the observed SVR rate of 30%. Percent of subjects with SVR35 were predicted to be higher for higher doses of navitoclax and ruxolitinib. Specifically, a 10% higher $SVR_{35}$ was predicted with ruxolitinib dose of 20 mg BID compared to 10 mg BID at week 24 in combination with navitoclax at 200 mg QD (FIG. 6).

Thus, simulation of spleen volume response at different navitoclax and ruxolitinib dose combinations suggested that safety permitting, higher ruxolitinib doses are likely to provide better spleen volume response in patients with R/R MF.

Using model-based approach, it was proposed that subjects on a stable dose of ruxolitinib at the time of study entry can continue at that dose in combination with navitoclax (at 100 mg QD or 200 mg QD based on baseline platelet count). Furthermore, the dose reduction strategy established in Phase 3 trials and safety and tolerability data from Example 1 support starting ruxolitinib at >10 mg BID, e.g. 200 mg QD or 100 mg QD Navitoclax and 10, 15, or 20 mg ruxolitinib BID, depending on baseline platelet counts. For subjects who have not been on a stable dose of ruxolitinib at time of study entry were proposed to start ruxolitinib therapy at 10 mg BID in combination with navitoclax.

Example 3

Extended Phase 2 Open-Label Study Evaluating Tolerability and Efficacy of Navitoclax Alone or in Combination with Ruxolitinib in Subjects with Myelofibrosis Objective(s)

Building off Example 1, the primary objective of this study is to evaluate the effect of navitoclax alone or in combination with ruxolitinib on spleen volume reduction.

The secondary objectives of the study are: to assess the effect of navitoclax alone or in combination with ruxolitinib on total symptom score (TSS) as assessed by the Myelofibrosis Symptom Assessment Form (MFSAF) version 4.0 diary, to evaluate the effect of navitoclax alone or in combination with ruxolitinib on bone marrow fibrosis, to determine the rate of anemia response associated with navitoclax alone or in combination with ruxolitinib, and to describe the safety profile and PK profile observed with navitoclax alone or in combination with ruxolitinib.

The exploratory objectives of the study include but are not limited to the evaluation of the duration of disease response including effects on spleen and anemia, survival, impact on quality of life and translational biomarkers.

Study Population

Approximately 164 subjects with primary or secondary (post-polycythemia vera MF [PPV-MF]), post-essential thrombocythemia [PET-MF]) myelofibrosis who have received prior treatment with ruxolitinib or another JAK-2 inhibitor (Cohorts 1a, 1b and 2) or who have not received prior treatment with a JAK-2 inhibitor or BET inhibitor (Cohort 3).

Methodology

Figure 7:
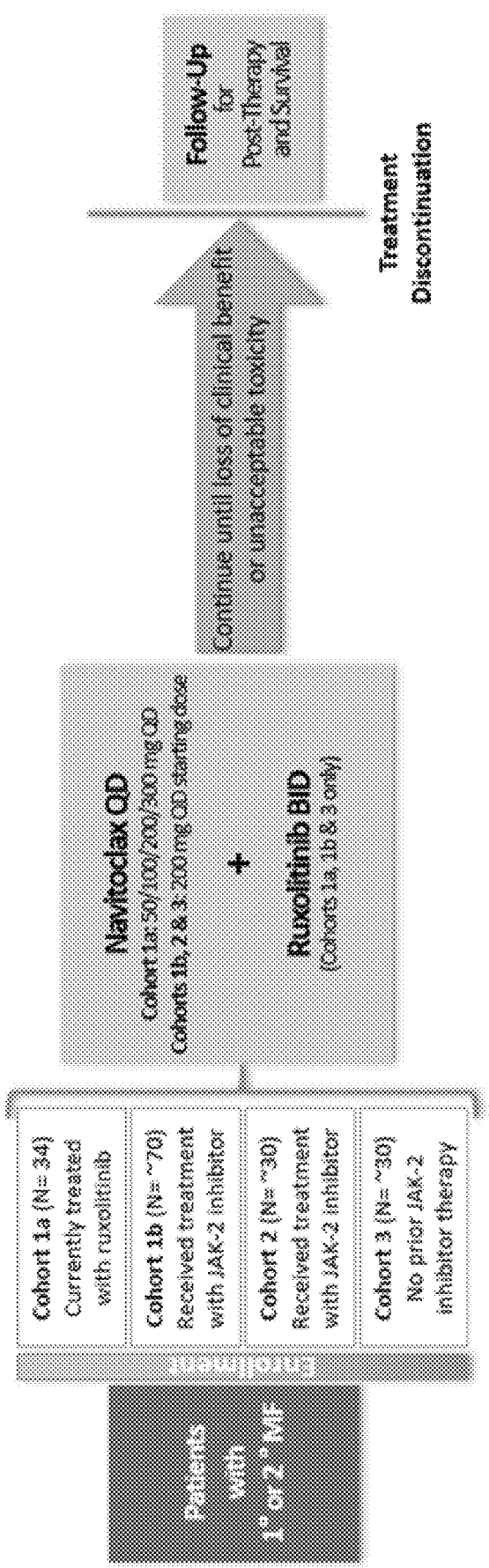
FIG. 7 shows the design of a Phase 2, multicenter, open-label study to evaluate the tolerability and efficacy of navitoclax alone or in combination with ruxolitinib in subjects with primary or secondary myelofibrosis.

This extended Phase 2, multicenter, open-label study (FIG. 7) evaluates the tolerability and efficacy of navitoclax alone or in combination with ruxolitinib in subjects with primary or secondary myelofibrosis. For Cohort 1a, subjects must have received ruxolitinib therapy for at least 12 weeks and currently be on a stable dose of ≥10 mg twice daily of ruxolitinib. For Cohorts 1b or 2, subjects must have received prior treatment with a JAK-2 inhibitor. For Cohort 3, subjects must not have received prior treatment with a JAK-2 inhibitor or BET inhibitor. Navitoclax will be administered at a starting dose of 50 mg once daily (Cohort 1a) or at 100 or 200 mg once daily (Cohorts 1b, 2 and 3).

Navitoclax Dose

Cohort 1a

The dose of navitoclax may be increased after approximately 7 or more days to the next dose level provided the platelet count is ≥75×10$^9$/L up to a maximum dose of navitoclax 300 mg once daily.

Cohorts 1b, 2 or 3

Baseline Platelet Count >150×10$^9$/L: 200 mg once daily navitoclax starting dose.

Baseline platelet count ≤150×10$^9$/L: 100 mg once daily navitoclax starting dose. The dose of navitoclax may be increased to 200 mg once daily after 7 days provided the platelet count is ≥75×10$^9$/L.

The dose of navitoclax should not exceed 200 mg once daily for the first 24 weeks of treatment.

After the Week 24 disease assessment, the dose of navitoclax may be increased to 300 mg once daily for subjects with sub-optimal spleen response defined as failure to achieve spleen volume reduction of at least 10% as assessed by imaging.

Ruxolitinib Dose

Cohorts 1a and 1b

Subjects receive ruxolitinib administered orally twice daily at either the current stable dose of ≥10 mg twice daily or at a dose of 10 mg twice daily if not currently taking ruxolitinib at the time of screening.

Cohort 3

Subjects receive ruxolitinib administered orally twice daily at the individualized starting dose based on baseline platelet count as per the local approved ruxolitinib label, e.g. the FDA-approved JAKAFI® label in the US.

Cohort 2

Subjects receive Navitoclax monotherapy.

Diagnosis and Main Criteria for Inclusion/Exclusion

Key Inclusion

Subjects ≥18 years of age

Subjects with documented diagnosis of Primary MF, PPV-MF or PETMF as defined by the World Health Organization classification.

Subjects classified as intermediate-2 or high-risk MF, as defined by the Dynamic International Prognostic Scoring System (DIPSS.)

Subject must be ineligible or unwilling to undergo stem cell transplantation at time of study entry.

ECOG 0, 1, or 2.

Cohort 1a Only

Subject must have received ruxolitinib therapy for at least 12 weeks and be currently on a stable dose of ≥10 mg twice daily of ruxolitinib for ≥8 weeks prior to the 1$^{st}$ dose of navitoclax. (Subjects with ruxolitinib dose reductions within 8 weeks prior to study enrollment may be considered on a stable dose if stable at that decreased dose of ruxolitinib for ≥2 weeks prior to the 1$^{st}$ dose of navitoclax. If the dose reduction was due to thrombocytopenia, the platelets must be confirmed to be stable by a repeat laboratory test).

Cohort 1b Only

Subject must have received prior treatment with JAK-2 inhibitor therapy and meet one of the following criteria:

Prior treatment with JAK-2 inhibitor for ≥24 weeks that was stopped for lack of efficacy or intolerance, Prior treatment with JAK-2 inhibitor for <24 weeks with documented disease progression while on JAK-2 inhibitor therapy as defined by any of the following:

a. Appearance of new splenomegaly that is palpable to at least 5 cm below the left costal margin (LCM) in subjects with no evidence of splenomegaly prior to the initiation of JAK-2 inhibitor.

b. A≥100% increase in the palpable distance below the LCM in subjects with measurable spleen distance 5 to 10 cm prior to the initiation of JAK-2 inhibitor.

c. A≥50% increase in the palpable distance below the LCM in subjects with measurable spleen distance >10 cm prior to the initiation of JAK-2 inhibitor.

d. A spleen volume increase of ≥25% (as assessed by MRI or CT scan) in subjects with a spleen volume assessment prior to the initiation of JAK-2 inhibitor.

Prior treatment with JAK-2 inhibitor for ≥28 days complicated by i or ii while receiving a total daily ruxolitinib dose of ≥30 mg but unable to reduce dose further due to lack of efficacy.

i. Development of RBC transfusion requirement (at least 2 units/month for 2 months), or ii. Grade ≥3 adverse events of neutropenia and/or anemia while on JAK-2 inhibitor treatment.

Cohort 2 Only

Subject must have received prior treatment with JAK-2 inhibitor therapy and meet one of the following criteria (a or b):
  a. Prior treatment with JAK-2 inhibitor for at least 12 weeks
  b. Prior treatment with JAK-2 inhibitor for at least 28 days complicated by any of the following:
    i. Development of red blood cell transfusion requirement (at least 2 units/month for 2 months) or
    ii. Grade ≥3 adverse events of thrombocytopenia, anemia, hematoma and/or hemorrhage while on JAK-2 inhibitor treatment Cohort 3 Only Subject must not have received prior treatment with a JAK-2 or BET inhibitor.

Subject has splenomegaly defined as spleen palpation measurement ≥5 cm below costal margin or spleen volume ≥450 cm$^3$ as assessed by MRI/CT, Cohorts 1b and 3 Only Subject has at least 2 symptoms each with a score ≥3 or a total score of ≥12, as measured by the MFSAF v4.0.

Subject must meet the following laboratory parameters per local laboratory reference range at Screening:

Adequate bone marrow reserves; in the absence of growth factors, thrombopoietic factors, or platelet transfusions for at least 14 days:
  a. Platelet count ≥100×10$^9$/L (Cohorts 1a, 1b or 3)
  b. Platelet count ≥75×10$^9$/L (Cohort 2)
  c. ANC ≥1×10$^9$/L Renal Function:
  a. calculated creatinine clearance ≥30 mL/min Hepatic Function and Enzymes:
  a. AST and ALT ≤3.0× the upper normal limit (ULN)
  b. Total Bilirubin ≤1.5×ULN (exception: subjects with Gilbert's Syndrome may have a Bilirubin >1.5×ULN)

Coagulation:
  a. aPTT and INR ≤1.5×ULN

Key Exclusions

Splenic irradiation within 6 months prior to Screening, or prior splenectomy

Leukemic transformation (>10% blasts in peripheral blood or bone marrow biopsy)

Subject is currently on medications that interfere with coagulation (including warfarin) or platelet function with the exception of low dose aspirin (up to 100 mg) and low-molecular-weight heparin (LMWH).

Prior therapy with a BH3 mimetic compound.

Cohort 1b Drug-Drug Interaction (DDI) sub-study subjects only: Subject has received strong or moderate CYP3A inhibitors (e.g., ketoconazole, clarithromycin and fluconazole) within 14 days prior to the administration of the first dose of navitoclax.

Cohort 1a Planned Navitoclax Dose(s) (Mode of Administration: Oral)
  Dose Level −1: 25 mg once daily
  Dose Level 1 (Starting Dose): 50 mg once daily
  Dose Level 2: 100 mg once daily
  Dose Level 3: 200 mg once daily
  Dose Level 4: 300 mg once daily Cohorts 1b, 2 and 3 Planned Navitoclax Dose(s) (Mode of Administration: Oral)
  Dose Level −3: 25 mg once daily
  Dose Level −2: 50 mg once daily
  Dose Level −1: 100 mg once daily (Starting dose; baseline platelet count ≤150×10$^9$/L)
  Dose Level 1: 200 mg once daily (Starting dose; baseline platelet count >150×10$^9$/L)
  Dose Level 2: 300 mg once daily (after Week 24 for inadequate response)

All Cohorts Planned Ruxolitinib Dose(s) (Mode of Administration: Oral)
  ≥10 mg twice daily
  Dose reductions to 5 mg twice daily is permissible during study, if needed for management of toxicities.

Duration of Treatment

Until end of clinical benefit or occurrence of unacceptable toxicity or discontinuation criteria have been met.

Toxicity Management for Thrombocytopenia

Navitoclax accelerates apoptosis of circulating mature platelets whether endogenous or transfused. This mechanism of toxicity differs from the thrombocytopenia caused by ruxolitinib and other conventional chemotherapy (i.e., toxicity to platelet progenitors in the bone marrow) and should, therefore, be managed according to the guidelines below.

Dose Adjustment Guidelines for Thrombocytopenia

If platelets ≥75×10$^9$/L, maintain current dose of navitoclax OR escalate navitoclax dose by one dose level not to exceed 200 mg once daily (Cohorts 1b, 2 or 3) or 300 mg once daily (Cohort 1a and after the Week 24 disease assessment for Cohorts 1b, 2 or 3). The dose of navitoclax should only be escalated if current dose of navitoclax has been administered for at least 7 days. If applicable, modify the ruxolitinib dose according to the approved local label for ruxolitinib. Platelet count should be rechecked approximately 7 days after navitoclax dose escalation.

If platelets ≤75×10$^9$/L–≥50×10$^9$/L, maintain current navitoclax dose level or consider navitoclax dose reduction to one dose level lower. If applicable, reduce the dose ruxolitinib per the approved local label guidance. Platelet count should be rechecked approximately every 7 days until ≥2 consecutive lab values indicate stable platelet count.

If platelets <50×10$^9$/L, for Cohorts 1a, 1b and 3, interrupt ruxolitinib and navitoclax. Recheck platelets every 2-3 days until recovery to ≥50×10$^9$/L. Then resume navitoclax at one dose level lower and ruxolitinib per the approved local label guidance. Platelet count should be rechecked approximately every 7 days until ≥2 consecutive lab values indicate stable platelet count.

If platelets <50×10$^9$/L, for Cohort 2, interrupt navitoclax. Recheck platelets every 2-3 days until recovery of platelets to ≥50×10$^9$/L and then resume navitoclax at one dose level lower. Platelet count should be rechecked approximately every 7 days until ≥2 consecutive lab values indicate stable platelet count.

Criteria for Evaluation

Efficacy

To determine initial disease status, MRI, bone marrow biopsy and aspirate are obtained at screening for all subjects. The local bone marrow evaluation includes staining for fibrosis and cytogenetics. To assess for efficacy, bone marrow biopsy, aspirate, MRI, MFSAF and laboratory tests are performed at designated timepoints throughout until disease progression is documented.

Efficacy is assessed according to International Working Group-Myeloproliferative Neoplasms Research and European LeukemiaNet (IWG-MRT/ELN).

Transfusion requirements are documented during the time period of 12 weeks before the start of navitoclax on Day 1.

Statistical Methods

Primary Efficacy Endpoint

At least 35% reduction from baseline in spleen volume at Week 24 ($SVR_{35w24}$) as measured by MRI/CT.

Secondary Efficacy Endpoints

At least 50% reduction in total symptom score (TSS) at Week 24 from baseline as measured by MFSAF v4.

Anemia Response.

Change in grade of bone marrow fibrosis.

Sample Size

For Cohort 1a, approximately 34 subjects are enrolled; For Cohort 1b, approximately 70 subjects are enrolled; For Cohorts 2 and 3, approximately 30 subjects are enrolled into each cohort.

Table 20 provides point estimate of $SVR_{35w24}$ Rate and corresponding 95% confidence interval (CI) assuming different response rate scenarios given proposed sample sizes.

TABLE 20

| Cohort | Sample size | Number of Subjects with $SVR_{35w24}$ | Point Estimate $SVR_{35w24}$ Rate (%) | Exact 95% CI Lower Limit (%) | Exact 95% CI Upper Limit (%) | Half Width of CI |
|---|---|---|---|---|---|---|
| 1a | 34 | 16 | 47.06 | 29.78 | 64.87 | 17.55 |
| 1a | 34 | 18 | 52.94 | 35.13 | 70.22 | 17.55 |
| 1a | 34 | 20 | 58.82 | 40.70 | 75.35 | 17.33 |
| 1a | 34 | 22 | 64.71 | 46.49 | 80.25 | 16.88 |
| 1b | 70 | 32 | 45.71 | 33.74 | 58.06 | 12.16 |
| 1b | 70 | 34 | 48.57 | 36.44 | 60.83 | 12.19 |
| 1b | 70 | 36 | 51.43 | 39.17 | 63.56 | 12.19 |
| 1b | 70 | 38 | 54.29 | 41.94 | 66.26 | 12.16 |
| 2 or 3 | 30 | 12 | 40.00 | 22.66 | 59.40 | 18.37 |
| 2 or 3 | 30 | 14 | 46.67 | 28.34 | 65.67 | 18.67 |
| 2 or 3 | 30 | 16 | 53.33 | 34.33 | 71.66 | 18.67 |
| 2 or 3 | 30 | 18 | 60.00 | 40.60 | 77.34 | 18.37 |

Based on the table above, this study with proposed sample sizes provides a reasonable precise estimate of the proportion of subjects with $SVR_{35w24}$ for each cohort. Also, if true probability of experiencing a serious adverse event (SAE) due to the study drug is 10%, then the probability of observing at least one SAE in 34 subjects is more than 97% in Cohort 1a; the probability of observing at least one SAE in 70 subjects is more than 99% in Cohort 1b; and the probability of observing at least one SAE in 30 subjects is more than 95% in either Cohort 2 or 3. Therefore, from safety assessment prospective the proposed sample sizes are adequate.

Example 4

Phase 3 Study Design of Navitoclax in Combination with Ruxolitinib in Subjects with Primary or Secondary Myelofibrosis M16-191: A Randomized, Open-Label, Phase 3 Study of Navitoclax in Combination with Ruxolitinib Versus Ruxolitinib Alone in Subjects with Myelofibrosis Objectives The primary objective is to evaluate the effect of navitoclax in combination with ruxolitinib on splenomegaly response when compared to ruxolitinib alone in subjects with MF.

The secondary objectives are to evaluate the effect of navitoclax in combination with ruxolitinib on the onset, magnitude, and duration of disease response, including Total Symptom Score (TSS), effects on spleen, bone marrow fibrosis, and anemia, to evaluate the effect of navitoclax in combination with ruxolitinib on measures of health-related quality of life (HRQoL), including fatigue, and physical functioning, and to evaluate the effect of navitoclax in combination with ruxolitinib on overall survival (OS) and leukemia-free survival (LFS).

The exploratory objectives are to evaluate responses to navitoclax and ruxolitinib versus ruxolitinib in subjects with high molecular risk (HMR) mutations, to evaluate the effect of navitoclax in combination with ruxolitinib on progression-free survival (PFS), to evaluate the effect of navitoclax in combination with ruxolitinib on the frequency of mutated alleles, exploration of biomarkers predictive of navitoclax activity and response may be performed. Potential analysis may include, but will not be limited to, the evaluation of: BCL-2 family profiling, inflammatory cytokine reduction, and/or mutational status.

Endpoints

Primary Efficacy Endpoint

At least 35% reduction in spleen volume from baseline at Week 24 ($SVR_{35w24}$) as measured by magnetic resonance imaging (MRI) or computed tomography (CT) scan, per International Working Group (IWG) criteria.

Secondary Efficacy Endpoints

At least 50% reduction in total symptom score (TSS) at Week 24 from baseline as measured by Myelofibrosis Symptom Assessment Form (MFSAF) v4.0

At least 35% reduction in spleen volume from baseline ($SVR_{35}$) as measured by MRI or CT scan, per IWG criteria Duration of $SVR_{35}$ Change in fatigue from baseline as measured by the PROMIS Fatigue SF 7a Time to deterioration of physical functioning, as measured by the physical functioning domain of the European Organisation for Research and Treatment of Cancer (EORTC) quality of life questionnaire (QLQ)-C30

Anemia response per IWG criteria

Overall survival

Leukemia-free survival

Overall response and composite response per IWG criteria.

Reduction in grade of bone marrow fibrosis from baseline as measured by the European consensus grading system Exploratory Endpoints At least 50% reduction in palpable splenomegaly from baseline per IWG criteria Red blood cell (RBC) transfusion during study drug treatment Change in quality of life from baseline as measured by the global health status/quality of life domain of the EORTC-QLQ-C30

Change from baseline in the summary score for the EORTC QLQ-C30

Progression-free survival per IWG criteria

Change in frequency of allelic mutations from baseline

Translational biomarkers

Response in subjects with high molecular risk (HMR) mutations.

Change in EQ-5D-5L from baseline

Change in impacts associated with fatigue from baseline as assessed by the PROMIS Fatigue 7a impact items Change in fatigue-related symptoms from baseline as assessed by the PROMIS Fatigue 7a symptom items Safety Endpoints Safety endpoints will be based on the following evaluations: adverse event (AE) monitoring, physical examinations, vital sign measurements, electrocardiogram (ECG) variables, and clinical laboratory testing (hematology and chemistry).

Study Population

Approximately 230 adult subjects with intermediate-2, or high-risk MF that have not been previously treated with JAK-2 inhibitor therapy Investigational Plan Approximately 230 subjects will receive either navitoclax once daily and ruxolitinib twice daily (Arm A), or placebo once daily and ruxolitinib twice daily (Arm B, control) until end of clinical benefit or occurrence of unacceptable toxicity or discontinuation criteria have been met. Stratification will be based on intermediate-2 versus high risk (Dynamic International Prognostic Scoring System Plus [DIPSS+]) and platelet count ≤200×10$^9$/L versus >200×10$^9$/L.

Subject Inclusion Criteria

Subject ≥18 years of age.

Subject with a documented diagnosis of primary MF or secondary MF (post polycythemia vera [PPV]-MF or post essential thrombocythemia [PET]-MF) as defined by the World Health Organization classification.

Subject must be able to complete the MFSAF v4.0 on at least 4 out of 7 days prior to Week 1 Day 1.

Subject has at least 2 symptoms with a score ≥3 or a total score of ≥12, as measured by the MFSAF v4.0.

Subject classified as intermediate-2 or high-risk MF as defined by the Dynamic International Prognostic Scoring System.

Subject must not have received prior treatment with a JAK-2 inhibitor.

Subject must not have received prior treatment with a BH3-mimetic compound or bromodomain and extra-terminal motif (BET) inhibitor.

Subject has splenomegaly defined as spleen palpation measurement ≥5 cm below costal margin or spleen volume ≥450 cm$_3$ as assessed centrally by MRI or CT scan.

Subject must be ineligible for stem cell transplantation at time of study entry.

Subject with an Eastern Cooperative Oncology Group (ECOG) performance status of 0, 1, or 2.

Subject must not receive medication that interferes with coagulation or platelet function except for low dose aspirin (up to 100 mg daily) and low molecular weight heparin (LMWH) within 3 days prior to the first dose of study drug or during the study treatment period.

Study Drug and Duration of Treatment

Navitoclax is provided as film-coated tablets (25 mg and 100 mg) for oral administration.

Arm A—Experimental group: navitoclax+ruxolitinib

Arm B—Control group: placebo to match navitoclax plus ruxolitinib

Dosing of Study Drug:

Navitoclax/placebo:

Platelet count >150×10$^9$/L: 200 mg once daily starting dose

Platelet count ≤150×10$^9$/L: 100 mg once daily starting dose; escalate to 200 mg once daily after ≥7 days, if tolerable (platelets ≥75×10$^9$/L).

After the Week 25 Day 1 visit, dose may be increased to 300 mg once daily at the discretion of the investigator based on platelet count for subjects with sub-optimal spleen response defined as failure to achieve a spleen volume reduction of at least 10%.

Dosing of Ruxolitinib (Administered Per USPI/SmPC/Local Prescribing Guidance):

Platelet count >200×10$^9$/L: 20 mg twice daily starting dose

Platelet count 100×10$^9$/L to 200×10$^9$/L: 15 mg twice daily starting dose.

Ruxolitinib dose adjustment in subjects with hepatic or renal impairment should be determined per local label/prescribing guidance.

Treatment continues until end of clinical benefit or occurrence of unacceptable toxicity or discontinuation criteria have been met.

Example 5

Phase 3 Study Design of Navitoclax in Combination with Ruxolitinib in Subjects with Relapsed or Refractory Myelofibrosis M20-178: A Randomized, Open-Label, Phase 3 Study of Navitoclax in Combination with Ruxolitinib versus Best Available Therapy in Subjects with Relapsed/Refractory Myelofibrosis Objectives The primary objective is to evaluate the effect of navitoclax in combination with ruxolitinib compared to BAT on splenomegaly response in subjects with relapsed/refractory MF.

The secondary objectives are: to evaluate the effect of navitoclax in combination with ruxolitinib compared to BAT on measures of health-related quality of life (HRQoL) including total symptom score, fatigue, and physical functioning, to evaluate the effect of navitoclax in combination with ruxolitinib compared to BAT on the onset, magnitude, and duration of disease response, including effects on spleen, bone marrow fibrosis, and anemia, and to evaluate the effect of navitoclax in combination with ruxolitinib compared to BAT on overall survival (OS) and leukemia-free survival (LFS).

The exploratory objectives are to evaluate responses to navitoclax in combination with ruxolitinib versus BAT in subjects with high molecular risk (HMR) mutations, to evaluate the effect of navitoclax in combination with ruxolitinib on progression-free survival, to evaluate the effect of navitoclax in combination with ruxolitinib compared to BAT on the frequency of mutated alleles, and exploration of biomarkers predictive of navitoclax activity and response may be performed, where potential analysis may include, but will not be limited to: to evaluate BCL-2 family profiling; to evaluate inflammatory cytokine reduction; and to evaluate mutational status.

Endpoints

Primary Efficacy Endpoint

At least 35% reduction in spleen volume from baseline at Week 24 (SVR$_{35w24}$) as measured by magnetic resonance imaging (MRI) or computed tomography (CT) scan, per International Working Group (IWG) criteria.

Secondary Efficacy Endpoints

At least 50% reduction in total symptom score (TSS) at Week 24 from baseline as measured by Myelofibrosis Symptom Assessment Form (MFSAF) v4.0

At least 35% reduction in spleen volume from baseline (SVR$_{35}$) as measured by MRI or CT scan, per IWG criteria Duration of SVR$_{35}$ Change in fatigue from baseline as measured by the PROMIS Fatigue SF 7a Time to deterioration of physical functioning as measured by the physical functioning domain of the EORTC QLQ-C30

Anemia response per IWG criteria
Overall survival
Leukemia-free survival
Overall response and composite response per IWG criteria
Reduction in grade of bone marrow fibrosis from baseline as measured by the European consensus grading system
Exploratory Endpoints
At least 50% reduction in palpable splenomegaly from baseline per IWG criteria
Red blood cell (RBC) transfusion during study treatment
Change in quality of life from baseline as measured by the global health status/quality of life domain of the EORTC-QLQ-C30
Change from baseline in the summary score for the EORTC QLQ-C30
Progression-free survival time per IWG criteria
Change in frequency of allelic mutations from baseline
Translational biomarkers
Response in subjects with high molecular risk (HMR) mutations
Change in EQ-5D-5L from baseline
Change in fatigue-related symptoms from baseline as assessed by the PROMIS Fatigue 7a symptom items
Change in impacts associated with fatigue from baseline as assessed by the PROMIS Fatigue 7a impact items
Safety Endpoints
Safety endpoints will be based on the following evaluations:
  Adverse event monitoring
  Physical examinations
  Vital sign measurements
  Electrocardiogram (ECG) variables
  Clinical laboratory testing (hematology and chemistry).
Study Population
Approximately 330 adult subjects with relapsed or refractory MF who have previously been treated with a JAK-2 inhibitor, have measurable splenomegaly, and are not candidates for allogeneic stem cell transplantation.
Investigational Plan
This is a Phase 3, open-label, randomized, 2-arm study evaluating the efficacy and safety of the combination of navitoclax and ruxolitinib compared to BAT, in subjects with intermediate-2 or high-risk MF.
Approximately 330 subjects will be randomized to receive either navitoclax once daily and ruxolitinib twice daily (Arm A) or BAT (Arm B, control). Stratification will be based on region (US versus Japan versus Europe versus Rest of World), Dynamic International Scoring System Plus (DIPSS+; intermediate-2 versus high risk), JAK-2 inhibitor therapy at time of randomization (on stable ruxolitinib versus not on ruxolitinib/JAK-2 inhibitor).
Subject Inclusion Criteria
Subject ≥18 years of age.
Subject must be able to complete the MFSAF v4.0 on at least 4 out of 7 days prior to randomization.
Subject has at least 2 symptoms with a score ≥3 or a total score of ≥12, as measured by the MFSAF v4.0.
Subject with a documented diagnosis of primary MF, post polycythemia vera (PPV)-MF, or post essential thrombocythemia (PET)-MF as defined by the World Health Organization classification.
Subject classified as intermediate-2 or high-risk MF, as defined by the Dynamic International Prognostic Scoring System (DIPSS).
Subject must have received prior treatment with a single JAK-2 inhibitor and meet one of the following criteria (in addition to the minimum splenomegaly and symptom burden also required for eligibility):
  a. Prior treatment with JAK-2 inhibitor for ≥24 weeks that was stopped due to lack of spleen response (refractory), or loss of spleen response or symptom control after a previous response (relapsed), or was continued despite relapsed/refractory status
  b. Prior treatment with JAK-2 inhibitor for <24 weeks with documented disease progression while on JAK-2 inhibitor therapy as defined by any of the following:
    i. Appearance of new splenomegaly that is palpable to at least 5 cm below the left costal margin (LCM) in subjects with no evidence of splenomegaly prior to the initiation of JAK-2 inhibitor.
    ii. A ≥100% increase in the palpable distance below the LCM in subjects with measurable spleen distance 5 to 10 cm prior to the initiation of JAK-2 inhibitor.
    iii. A≥50% increase in the palpable distance below the LCM in subjects with measurable spleen distance >10 cm prior to the initiation of JAK-2 inhibitor.
    iv. A spleen volume increase of ≥25% (as assessed by MRI or CT scan) in subjects with a spleen volume assessment prior to the initiation of JAK-2 inhibitor.
Subject must not have received prior treatment with a BH3-mimetic compound or prior use of >1 JAK-2 inhibitor.
Subject has splenomegaly defined as spleen palpation measurement ≥5 cm below costal margin or spleen volume ≥450 cm$^3$ as assessed centrally by MRI or CT scan.
Subject has a baseline platelet count ≥100×10$^9$/L.
Subject must not receive medication that interferes with coagulation or platelet function except for low dose aspirin (up to 100 mg daily) and low molecular weight heparin (LMWH) within 3 days prior to the first dose of study drug or during the study treatment period.
Subject must not receive anticancer therapy including chemotherapy, radiation therapy, hormonal therapy (with the exception of hormones for thyroid conditions or estrogen replacement therapy) within 30 days prior to first dose of study drug, and during the study treatment period (other than any overlapping therapy as part of the selected BAT).
Study Drug and Duration of Treatment
Navitoclax is provided as film-coated tablets (25 mg and 100 mg) for oral administration.
Arm A—Experimental Group: Navitoclax+Ruxolitinib
Navitoclax Dosing
Platelet count >150×10$^9$/L: 200 mg once daily
Platelet count ≤150×10$^9$/L: 100 mg once daily; if tolerable, may increase to 200 mg once daily
After the Week 25 Day 1 visit, dose may be increased to 300 mg once daily at the discretion of the investigator based on platelet count for subjects with sub-optimal spleen response defined as failure to achieve a spleen volume reduction of at least 10%.
Ruxolitinib Dosing
Subjects receiving ruxolitinib at Screening will continue at the current stable dose of ≥10 mg twice daily
Subjects not receiving ruxolitinib at Screening will receive ruxolitinib at a dose of 10 mg twice daily.
Ruxolitinib dose adjustment in subjects with hepatic or renal impairment is determined per local label/prescribing guidance.
Arm B—Control Group: Best Available Therapy
The investigator identifies one of the following treatment options for each subject pre-randomization: ruxolitinib, hydroxyurea, PEG-interferon-α2 or danazol additional options where BAT is sourced locally include other locally available formulations of interferon and fedratinib, where approved for relapsed/refractory MF.

Treatment continues until end of clinical benefit, occurrence of unacceptable toxicity, or discontinuation criteria have been met.

What is claimed is:

1. A method for treatment of a human subject having myelofibrosis comprising concomitant administration to the human subject of:
   (i) a therapeutically effective amount of navitoclax selected from the group consisting of 50 mg, 100 mg, 200 mg, and 300 mg once daily; and
   (ii) a therapeutically effective amount of ruxolitinib selected from the group consisting of 10 mg, 15 mg, and 20 mg twice daily,
   wherein the method results in a spleen volume reduction of at least 35% in the human subject at week 24 of the treatment.

2. The method of claim 1, wherein the myelofibrosis is relapsed and/or refractory myelofibrosis.

3. The method of claim 2, wherein the myelofibrosis is relapsed and/or refractory to treatment with a JAK-2 inhibitor.

4. The method of claim 1, wherein the myelofibrosis is primary myelofibrosis.

5. The method of claim 1, wherein the myelofibrosis is secondary myelofibrosis.

6. The method of claim 1, wherein the myelofibrosis is intermediate- or high-risk myelofibrosis.

7. The method of claim 1, wherein the therapeutically effective amount of navitoclax is 200 mg. once daily.

8. The method of claim 1, wherein the therapeutically effective amount of ruxolitinib is 10 mg. twice daily.

9. The method of claim 7, wherein the therapeutically effective amount of ruxolitinib is 10 mg. twice daily.

10. The method of claim 1, wherein the therapeutically effective amount of ruxolitinib is 20 mg. twice daily.

11. The method of claim 7, wherein the therapeutically effective amount of ruxolitinib is 20 mg. twice daily.

12. The method of claim 2, comprising concomitant oral administration to the human subject of:
    (i) 200 mg. navitoclax once daily; and
    (ii) a therapeutically effective amount of ruxolitinib selected from the group consisting of 10 mg. and 20 mg. twice daily.

13. The method of claim 12, wherein the myelofibrosis is relapsed and/or refractory to treatment with a JAK-2 inhibitor.

14. The method of claim 12, wherein the therapeutically effective amount of ruxolitinib comprises 10 mg. twice daily.

15. The method of claim 13, wherein the therapeutically effective amount of ruxolitinib comprises 10 mg. twice daily.

16. The method of claim 12, wherein the therapeutically effective amount of ruxolitinib is 20 mg. twice daily.

17. The method of claim 13, wherein the therapeutically effective amount of ruxolitinib is 20 mg. twice daily.

18. The method of claim 12, wherein the myelofibrosis is primary myelofibrosis.

19. The method of claim 12, wherein the myelofibrosis is secondary myelofibrosis.

20. The method of claim 12, wherein the myelofibrosis is intermediate- or high-risk myelofibrosis.

21. The method of claim 2, comprising concomitant oral administration to the human subject:
    (i) 200 mg. navitoclax once daily; and
    (ii) 10 mg. ruxolitinib twice daily.

22. The method of claim 21, wherein the myelofibrosis is relapsed and/or refractory to treatment with a JAK-2 inhibitor.

23. The method of claim 21, wherein the myelofibrosis is primary myelofibrosis.

24. The method of claim 21, wherein the myelofibrosis is secondary myelofibrosis.

25. The method of claim 21, wherein the myelofibrosis is intermediate- or high-risk myelofibrosis.

26. The method of claim 2, comprising concomitant oral administration to the human subject:
    (i) 200 mg. navitoclax once daily; and
    (ii) 20 mg. ruxolitinib twice daily.

27. The method of claim 26, wherein the myelofibrosis is relapsed and/or refractory to treatment with a JAK-2 inhibitor.

28. The method of claim 26, wherein the myelofibrosis is primary myelofibrosis.

29. The method of claim 26, wherein the myelofibrosis is secondary myelofibrosis.

30. The method of claim 26, wherein the myelofibrosis is intermediate- or high-risk myelofibrosis.

31. The method of claim 4, comprising concomitant oral administration to the human subject:
    (i) 200 mg. navitoclax once daily; and
    (ii) a therapeutically effective amount of ruxolitinib selected from the group consisting of 10 mg. and 20 mg. twice daily,.

32. The method of claim 31, wherein the therapeutically effective amount of ruxolitinib is 10 mg. twice daily.

33. The method of claim 31, wherein the therapeutically effective amount of ruxolitinib is 20 mg. twice daily.

34. The method of claim 31, wherein the myelofibrosis is primary myelofibrosis.

35. The method of claim 31, wherein the myelofibrosis is secondary myelofibrosis.

36. The method of claim 31, wherein the myelofibrosis is intermediate- or high-risk myelofibrosis.

37. The method of claim 5, comprising concomitant oral administration to the human subject:
    (i) 200 mg. navitoclax once daily; and
    (ii) a therapeutically effective amount of ruxolitinib selected from the group consisting of 10 mg. and 20 mg. twice daily.

38. The method of claim 37, wherein the therapeutically effective amount of ruxolitinib is 10 mg. twice daily.

39. The method of claim 37, wherein the therapeutically effective amount of ruxolitinib is 20 mg. twice daily.

40. The method of claim 37, wherein the myelofibrosis is primary myelofibrosis.

41. The method of claim 37, wherein the myelofibrosis is secondary myelofibrosis.

42. The method of claim 37, wherein the myelofibrosis is intermediate- or high-risk myelofibrosis.

* * * * *

UNITED STATES PATENT AND TRADEMARK OFFICE
CERTIFICATE OF CORRECTION

PATENT NO. : 11,285,159 B2
APPLICATION NO. : 17/089415
DATED : March 29, 2022
INVENTOR(S) : John Hayslip et al.

It is certified that error appears in the above-identified patent and that said Letters Patent is hereby corrected as shown below:

On the Title Page

On Page 3, in item (56), in Other Publications, Column 1, Line 16, delete "antitumoractivity" and insert therefor -- anti-tumor activity --.

On Page 3, in item (56), in Other Publications, Column 1, Line 59, delete "Decemeber3" and insert therefor -- December 3 --.

On Page 3, in item (56), in Other Publications, Column 1, Line 64, delete "Decembers," and insert therefor -- December 3, --.

On Page 3, in item (56), in Other Publications, Column 2, Line 3, delete "page viiil 16," and insert therefor -- page viii116, --.

On Page 3, in item (56), in Other Publications, Column 2, Line 7, delete "(9 Supp 1),AbsD5-4." and insert therefor -- (9 Supp 1), Abs D5.4. --.

On Page 3, in item (56), in Other Publications, Column 2, Line 28, delete "Novel Type li," and insert therefor -- Novel Type II, --.

On Page 3, in item (56), in Other Publications, Column 2, Line 31, delete "pp. abstract3915." and insert therefor -- abstract 3915. --.

On Page 3, in item (56), in Other Publications, Column 2, Line 50, delete "Chemother Pharmacology," and insert therefor -- Chemotherapy and Pharmacology, --.

On Page 3, in item (56), in Other Publications, Column 2, Line 62, delete "Saferand" and insert therefor -- Safer and --.

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,285,159 B2

On Page 4, in item (56), in Other Publications, Column 1, Line 39, delete "lungcancer" and insert therefor -- lung cancer --.

On Page 4, in item (56), in Other Publications, Column 1, Line 45, delete "&efficacy" and insert therefor -- & efficacy --.

On Page 4, in item (56), in Other Publications, Column 1, Lines 60-61, delete "Pharmacokineties, Safety and AntiTumor" and insert therefor -- Pharmacokinetics, Safety and Anti-Tumor --.

On Page 4, in item (56), in Other Publications, Column 2, Line 35, delete "Research , 2008," and insert therefor -- Research, 2008, --.

On Page 4, in item (56), in Other Publications, Column 2, Line 52, delete "Clinical Cancer Research :" and insert therefor -- Clinical Cancer Research: --.

On Page 5, in item (56), in Other Publications, Column 1, Line 14, delete "Onco Targets anf" and insert therefor -- OncoTargets and --.

On Page 5, in item (56), in Other Publications, Column 1, Line 22, delete "Anti-Aapoptotic" and insert therefor -- Anti-Apoptotic --.

On Page 5, in item (56), in Other Publications, Column 1, Line 48, delete "Doseescalation" and insert therefor -- Dose-escalation --.

On Page 5, in item (56), in Other Publications, Column 2, Line 23, delete "Bcl-XL , in" and insert therefor -- Bcl-XL, in --.

On Page 5, in item (56), in Other Publications, Column 2, Line 28, delete "Yokohama T., et al.," and insert therefor -- Yokoyama T., et al., --.

On Page 5, in item (56), in Other Publications, Column 2, Line 46, delete "Meeting Astracts" and insert therefor -- Meeting Abstracts --.

On Page 5, in item (56), in Other Publications, Column 2, Line 50, delete "BCL2/XL" and insert therefor -- BCL2/BCL-XL --.

In the Specification

In Column 5, Line 57, delete "subject s" and insert therefor -- subject --.

In Column 15, Line 28, delete "methyl-}-" and insert therefor -- methyl}-1 --.

In Column 15, Line 66, delete "Chemother Pharmacol" and insert therefor -- Chemotherapy and Pharmacology --.

In Column 17, Line 28, delete "upon recover" and insert therefor -- upon recovery --.

CERTIFICATE OF CORRECTION (continued)
U.S. Pat. No. 11,285,159 B2

In Column 18, Line 5, delete "C17H18N6.H3PO4;" and insert therefor -- C17H18N6·H3PO4; --.

In Column 19, Line 30, delete "TABLE 3 J" and insert therefor -- TABLE 3 --.

In Column 19, Line 31, delete "AKAFI®" and insert therefor -- JAKAFI® --.

In Column 20, Line 3, delete "JAKAFI ®" and insert therefor -- JAKAFI® --.

In Column 20, Line 10, delete "JAKAFI ®" and insert therefor -- JAKAFI® --.

In Column 22, Line 57, delete "JAKAFI ®" and insert therefor -- JAKAFI® --.

In Column 23, Line 3, delete "JAKAFI ®" and insert therefor -- JAKAFI® --.

In Column 64, Line 30, delete "(ACV)" and insert therefor -- (PCV) --.

In Column 64, Line 45, delete "(ACV)" and insert therefor -- (PCV) --.

In Column 71, Line 42, delete "last, very" and insert therefor -- last very --.

In Column 76, Line 59, delete "Chemother Pharmacol" and insert therefor -- Chemotherapy and Pharmacology --.

In Column 78, Line 57, delete "gut" and insert therefor -- gut, --.

In Column 78, Line 59, delete "constant" and insert therefor -- constant, --.

In Column 79, Line 39, delete "Chemother Pharmacol" and insert therefor -- Chemotherapy and Pharmacology --.

In Column 80, Table 16, Line 38, delete "variablity" and insert therefor -- variability --.

In the Claims

In Column 96, Claim 31, Line 35, delete "twice daily,." and insert therefor -- twice daily --.